(12) United States Patent
Denlinger et al.

(10) Patent No.: US 7,960,131 B2
(45) Date of Patent: *Jun. 14, 2011

(54) FUNCTIONAL GENOMIC PORE ASSAY FOR MIXED CELL POPULATIONS

(75) Inventors: Loren C. Denlinger, Madison, WI (US); Kirk J. Hogan, Madison, WI (US); Paul J. Bertics, Oregon, WI (US); Kathleen Schell, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/132,252

(22) Filed: Jun. 3, 2008

(65) Prior Publication Data

US 2009/0053204 A1  Feb. 26, 2009

Related U.S. Application Data

(63) Continuation-in-part of application No. 10/827,718, filed on Apr. 20, 2004, now Pat. No. 7,560,243.

(60) Provisional application No. 60/464,231, filed on Apr. 21, 2003.

(51) Int. Cl.
*G01N 33/00*  (2006.01)

(52) U.S. Cl. ....... 435/7.24; 435/6; 435/40.5; 435/287.2; 435/372; 436/517; 436/538; 436/548; 436/56; 436/63; 436/172; 436/175; 422/61; 422/73

(58) Field of Classification Search ................... 435/2, 3, 435/6, 7.2, 7.24, 40.5, 372, 383, 287.2; 422/61, 422/73; 436/517, 538, 548, 56, 63, 172, 436/175
See application file for complete search history.

(56) References Cited

U.S. PATENT DOCUMENTS

| | | | |
|---|---|---|---|
| 5,837,832 A | 11/1998 | Chee et al. | |
| 6,355,431 B1 | 3/2002 | Chee et al. | |
| 7,560,243 B2 * | 7/2009 | Denlinger et al. | ........... 435/7.24 |
| 2002/0182646 A1 | 12/2002 | Ke et al. | |

OTHER PUBLICATIONS

Fairbairn et al., J. Immunol. 2001, 167:3300-7.
Saunders et al., J. Immunol. 2003, 171:5442-6.
Bone et al., Chest 1997, 112(1):235-43.
Angus et al., Crit. Care Med. 2001, 29(7):1303-10.
Rivers et al., N. Engl. J. Med. 2001, 345(19):1368-77.
Tonetti et al., Biochem. & Biophys. Res. Communications 1995, 214(1):125-30.
Denlinger et al., J. Biol. Chem. 1996, 271(1):337-42.
Hu et al., J. Biol. Chem 1998, 273(42):27170-5.

(Continued)

*Primary Examiner* — Gailene R Gabel
(74) *Attorney, Agent, or Firm* — Quarles & Brady, LLP

(57) ABSTRACT

A method of assaying nucleotide receptor $P2X_7$ pore activity in white blood cells contained within a mixed cell sample is provided comprising labeling white blood cells with a white blood cell-specific label; depolarizing the labeled white blood cells with an isotonic depolarizing solution; contacting the labeled white blood cells with dye and a $P2X_7$ agonist in an amount sufficient to activate $P2X_7$ pore activity; contacting the labeled white blood cells with a divalent cation in an amount sufficient to deactivate $P2X_7$ pore activity; and analyzing dye uptake whereby $P2X_7$ pore activity is quantified by the amount of dye taken up in labeled white blood cells treated with the $P2X_7$ agonist relative to labeled white blood cells in the absence of said $P2X_7$ agonist, said $P2X_7$ pore activity being corrected for sample age and by subtraction of $P2X_7$ pore activity contributed by nonviable white blood cells.

23 Claims, 33 Drawing Sheets

OTHER PUBLICATIONS

MacKenzie et al., Immunity 2001, 15(5):825-35.
Di Virgilio et al., J. Leukoc Biol. 1999, 66(5):723-6.
Surprenant et al., Science 1996, 272(5262):735-8.
Gu et al., Am. J. Physiol. Cell Physiol. 2000, 279(4):C1189-97.
Gudipaty et al., Am. J. Physiol. Cell Physiol. 2001, 280(4):C943-53.
Lamping et al., J. Immunol 1996, 157(10):4648-56.
Poussin et al., J. Biol. Chem. 1998, 273(32):20285-91.
Vasselon et al., J. Exp. Med. 1999, 190(4):509-21.
Teasdale et al., Annu. Rev. Cell Dev. Biol. 1996, 12:27-54.
Khakh, Nature 2006, 442(7102):527-32.
Rassendren, J. Biol. Chem. 1997, 272(9):5482-6.
Buell, Receptors Channels 1998, 5(6):347-54.
Perregaux, J. Immunol. 2000, 165(8):4615-23.
Denlinger, J. Immunol 2005, 174(7):4424-31.
Fernando, Am. J. Resp. Critical Care Medicine 2006, 175:360-366.
Nino-Moreno, Clin. Exp Immunol 2007, 148(3):469-77.
Gordon, J. Clin. Invest 2005, 115(6):1408-18.
Rifai, Nat Biotechnol. 2006, 24(8):971-83.
Akbari, N. Engl J. Med. 2006, 354(11):1117-29.
Vijayanand, N. Engl J. Med. 2007, 356(14):1410-22.
Bayer, Cytometry B. Clin. Cytom. 2007, 72(1):8-13.

* cited by examiner

A.

B.

A.

C.

A.

B.

C.

A.

B.

C.

A.

B.

A.

B.

A.

B.

A.

B.

FUNCTIONAL GENOMIC PORE ASSAY FOR MIXED CELL POPULATIONS

CROSS-REFERENCE TO RELATED APPLICATION

This continuation-in-part application claims priority to U.S. application Ser. No. 10/827,718, filed Apr. 20, 2004 and issued as U.S. Pat. No. 7,560,243 on Jul. 14, 2009, which claimed the benefit of U.S. Provisional Application No. 60/464,231, filed Apr. 21, 2003, both of which are incorporated herein by reference in their entirety for all purposes.

STATEMENT REGARDING FEDERALLY SPONSORED RESEARCH OR DEVELOPMENT

This invention was made with United States government support awarded by the following agencies: NIH Grant No. AI50500. The United States Government has certain rights in this invention.

FIELD OF THE INVENTION

This invention relates generally to biomedical assays. In particular, this invention is directed to methods for rapidly assaying pore activity of the nucleotide receptor $P2X_7$.

BACKGROUND OF THE INVENTION

As used herein, septic shock refers to a systemic immune system dysfunction in response to an overwhelming infection leading to hypotension and organ failure (1). Over 750,000 cases of severe sepsis (the precursor to shock) occur each year in the United States with an overall mortality rate of 28%, making the number of deaths similar to that from coronary artery disease (2). Because early intervention with supportive therapies makes a difference in outcome (3), means to prospectively stratify patients on the basis of risk has become one of the central objectives in the sepsis field (1, 4). The failure of numerous clinical trials of immunomodulatory therapeutics over the past few decades, some of which actually show higher mortality, highlights the long felt need for improved prognostic indicators. These trials demonstrate that there is significant patient-to-patient diversity of immune responses during severe sepsis.

A novel signaling pathway pertinent to sepsis pathophysiology has recently been identified with global control over monocyte and macrophage inflammatory mediator production and microbial killing (5, 6). Specifically, extracellular adenine nucleotides, such as ATP, are released systemically by the adrenal gland, as well as locally by platelet degranulation and/or by cell death during the inflammatory response in sepsis. These hormones modulate monocyte and macrophage immune responses via interaction with the nucleotide receptor $P2X_7$ (5).

The $P2X_7$ receptor controls the production of inflammatory mediators during sepsis, including tumor necrosis factor-alpha (TNF-alpha), interleukin-1beta (IL-1beta), IL-6, nitric oxide (NO), tissue factor, and prostaglandins (7-12). $P2X_7$-knockout mice exhibit greatly attenuated production of IL-1beta and IL-6 in response to endotoxin (lipopolysaccharide, LPS) (11), a common pathogenic agent in severe sepsis. Additionally, $P2X_7$ stimulation promotes membrane fusion events such as phagolysosomal maturation necessary for microbial killing, microvesicle generation required for IL-1beta processing, and giant cell formation needed to make granulomas (13-15). Finally, co-administration of the ATP analogue, 2-methylthio-ATP, protects mice from endotoxic death in an animal model of severe sepsis with concomitant reductions in LPS-induced serum levels of TNF-alpha and IL-1 (7). Thus, extracellular adenine nucleotides and the nucleotide receptor $P2X_7$ have a profound influence on monocyte and macrophage immune responses relevant to sepsis pathophysiology.

The family of P2 receptors binds extracellular nucleotides with two or more phosphates and has been divided into the P2X and P2Y subfamilies according to whether the individual member acts as an ion channel or a G-protein coupled receptor, respectively (6). $P2X_7$ belongs to the P2X family due to its structural similarity with the six other members, each having two predicted membrane spanning domains (6, 16). Whereas ligand-gated, nonselective cation channel activity is a common feature of the P2X family, reversible permeability to larger molecules (<900 Da) is a feature more characteristic of $P2X_7$ under biological conditions (6).

The gene for human $P2X_7$ contains two previously-described single nucleotide polymorphisms (SNPs) associated with functionally significant amino acid substitutions. Gu et al. have shown that the human $P2X_7$ gene contains a nucleotide polymorphism (SNP, A1513C) conferring an amino acid substitution that disrupts the pore activity of this receptor. In addition, Wiley et al. report that a T1729A mutation is associated with reduced pore activity due to a trafficking defect (Wiley et al. *J. Biol. Chem.* 278:17108-17113 (2003)).

Because the $P2X_7$ pore activity has been linked to monocyte and macrophage inflammatory mediator production (particularly IL-beta (14)), and because inflammatory mediator production is a major determinant in deciding on courses of immunosuppressive and anti-inflammatory therapies, it is particularly desirable to obtain a rapid and convenient clinical assay for determining $P2X_7$ pore activity. A rapid assay of $P2X_7$ pore activity is required to make reliable prognoses and refined therapeutic interventions.

Unfortunately, presently-known $P2X_7$ pore assays do not provide rapid and robust procedures for use outside of the laboratory setting, most notably in the clinical setting. For example, Gu et al., *J. Biol. Chem.* 276, 11135-11142, describe the A1513C polymorphism and provide a $P2X_7$ pore assay based on ethidium bromide uptake in ATP-induced monocytes. A similar assay was utilized by Wiley et al. in analyzing the T1729A polymorphism. However, this assay requires extensive isolation and purification of these cells apart from other cell types before dye influx can be measured by time-resolved flow cytometry. In particular, this method requires the use of a ficoll hypaque density gradient to obtain the necessary monocytes. The preparatory step is therefore time-consuming and, due to the technical aspects related to density gradient separation, not practical in the clinical setting where complex bench and cold room facilities are not available. The time necessary to carry out this technique is estimated to be at least one full workday for one skilled in the field with multiple sample processing not easily amenable to automation. Moreover, the volume of blood needed for the previous $P2X_7$ pore assay (i.e., several hundred cc's) precludes testing in pediatric and frail subjects.

As well, Patent Application US 2002/0182646 A1, published Dec. 5, 2002 to Ke et al. describes a method for measuring $P2X_7$ receptor-mediated macromolecule uptake in macrophages. Like the method of Gu et al. discussed above, this approach also relies on complex preparatory steps to provide isolated and purified macrophages before pore activities may be reliably measured. Specifically, Ke et al. teach that macrophages are harvested from the peritoneal cavity of animals (e.g., mice) by medium injection into the cavity, followed by collection of the lavage fluid. Quite obviously, this approach does not provide a practical clinical procedure for rapid measurement of $P2X_7$ pore activity in humans.

Based upon the above-described needs and others, it is therefore desirable to obtain a rapid $P2X_7$ pore assay suitable for, but not limited to, use in the clinical setting. This assay would dispense with the time-consuming and technical complexities of previous methods. Preferably, the assay could be carried out directly on clinical specimens, such as, whole blood samples. Furthermore, the assay would provide improved sensitivity, reliability and robustness while, at the same time, being amenable to automation.

SUMMARY OF THE INVENTION

In one embodiment, the present invention provides a method of assaying nucleotide receptor $P2X_7$ pore activity in white blood cells contained within a blood sample. The method comprises labeling white blood cells contained within the mixed cell sample with a white blood cell-specific label; depolarizing the labeled white blood cells with an isotonic depolarizing solution; contacting the labeled white blood cells with a dye and a $P2X_7$ agonist in an amount sufficient to activate nucleotide receptor $P2X_7$ pore activity; contacting the labeled white blood cells with a divalent cation in an amount sufficient to deactivate nucleotide receptor $P2X_7$ pore activity; and analyzing dye uptake in the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist, said nucleotide receptor $P2X_7$ pore activity being corrected for sample age and by subtraction of nucleotide receptor $P2X_7$ pore activity contributed by nonviable white blood cells.

The white blood cell-specific label is preferably a phycoerythrin-conjugated anti-CD14 antibody and the isotonic depolarizing solution preferably comprises glutamate ion with the proviso that sodium and chloride ions and divalent cations are absent from said isotonic depolarizing solution in amounts effective to inhibit $P2X_7$ pore activity. The dye is a DNA-binding dye having a mass of less than approximately 900 Daltons such as YO-PRO-1.

The $P2X_7$ agonist is preferably selected from the group consisting of 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5' (beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof. In preferred embodiments the divalent cation is magnesium ion and dye uptake is measured by flow cytometry.

In a preferred embodiment, flow cytometry detects labeled white blood cells apart from non-labeled cells and measures intensity of the dye taken up by the labeled white blood cells whereby nucleotide receptor $P2X_7$ pore activity is quantified by the amount of dye taken up in labeled white blood cells in the absence of said $P2X_7$ agonist.

In an alternative embodiment, the invention provides a method of identifying a nucleotide receptor $P2X_7$-related molecular phenotype useful as a prognostic determinant of a clinical outcome in a patient. The method comprises labeling white blood cells contained within mixed cell samples from a patient population having known clinical outcomes to determine a plurality of receptor $P2X_7$ pore activities with a white blood cell-specific label; depolarizing the labeled white blood cells with an isotonic depolarizing solution; contacting the labeled white blood cells with a dye and a $P2X_7$ agonist in an amount sufficient to activate nucleotide receptor $P2X_7$ pore activity; contacting the labeled white blood cells with a divalent cation in an amount sufficient to deactivate nucleotide receptor $P2X_7$ pore activity; and analyzing dye uptake in the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist, said nucleotide receptor $P2X_7$ pore activity being corrected for sample age and by subtraction of nucleotide receptor $P2X_7$ pore activity contributed by nonviable white blood cells on and analyzing dye uptake in the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist; and correlating said nucleotide receptor $P2X_7$ pore activities with the known clinical outcomes to determine statistically significant correlations between respective pore activities and known clinical outcomes, thereby determining a particular nucleotide receptor $P2X_7$ molecular phenotype useful as a prognostic determinant in a patient.

In an alternate embodiment, the invention provides a method of identifying a nucleotide receptor $P2X_7$-related polymorphism useful as a prognostic determinant of a clinical outcome in a patient using mixed cell samples from a patient population having known clinical outcomes to determine a plurality of respective receptor $P2X_7$ pore activities. The method comprises labeling white blood cells contained within the mixed cell sample with a white blood cell-specific label; depolarizing the labeled white blood cells with an isotonic depolarizing solution; contacting the labeled white blood cells with a dye and a $P2X_7$ agonist in an amount sufficient to activate nucleotide receptor $P2X_7$ pore activity; contacting the labeled white blood cells with a divalent cation in an amount sufficient to deactivate nucleotide receptor $P2X_7$ pore activity; and analyzing dye uptake in the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist, said nucleotide receptor $P2X_7$ pore activity being corrected for sample age and by subtraction of nucleotide receptor $P2X_7$ pore activity contributed by nonviable white blood cells; correlating said nucleotide receptor $P2X_7$ pore activities with the known clinical outcomes to determine statistically significant correlation between respective pore activities and known clinical outcomes; and characterizing genomic material from respective patients in which statistically significant correlation was identified to identify a nucleotide receptor $P2X_7$-related polymorphism useful as a prognostic determinant.

In an alternative embodiment, the invention provides a method of providing immunomodulatory or anti-infectious therapy to a patient, A method of providing immunomodulatory or anti-infectious therapy to a patient, comprising the steps of analyzing a mixed cell sample from the patient to obtain a nucleotide receptor $P2X_7$ pore activity for said patient by labeling white blood cells contained within the mixed cell sample with a white blood cell-specific label; depolarizing the labeled white blood cells with an isotonic depolarizing solution; contacting the labeled white blood cells with a dye and a $P2X_7$ agonist in an amount sufficient to activate nucleotide receptor $P2X_7$ pore activity; contacting the labeled white blood cells with a divalent cation in an amount sufficient to deactivate nucleotide receptor P2X$_7$ pore activity; and analyzing dye uptake in the labeled white blood cells whereby nucleotide receptor P2X$_7$ pore activity is quantified by the amount of dye taken up in labeled white blood cells treated with the P2X$_7$ agonist relative to labeled white blood cells in the absence of said P2X$_7$ agonist, said nucleotide receptor P2X$_7$ pore activity being corrected for sample age and by subtraction of nucleotide receptor P2X$_7$ pore activity contributed by nonviable white blood cells; comparing said nucleotide receptor P2X$_7$ pore activity with previously-determined nucleotide receptor P2X$_7$ pore activities in a patient population that demonstrate statistically significant correlation to known clinical outcomes to arrive at a prognosis; and based upon said prognosis, providing immunomodulatory or anti-infectious therapy to either avoid or achieve a particular clinical outcome in said patient.

In an alternative embodiment, the invention provides a kit for measuring a nucleotide receptor P2X$_7$ pore activity in white blood cells contained within a mixed cell sample of a subject, the kit comprising a white blood cell-specific label for labeling white blood cells contained within the subject's sample; a dye capable of uptake by nucleotide receptor P2X$_7$ pores; a P2X$_7$ agonist in an amount sufficient to activate nucleotide receptor P2X$_7$ pore activity in the white blood cells contained within the subject's blood sample; and instructional material describing labeling white blood cells contained within the subject's sample with the white blood cell-specific label; depolarizing the labeled white blood cells; contacting the labeled white blood cells with the dye and the P2X$_7$ agonist in an amount sufficient to activate nucleotide receptor P2X$_7$ pore activity; deactivating nucleotide receptor P2X$_7$ pore activity; and analyzing dye uptake in the labeled white blood cells whereby nucleotide receptor P2X$_7$ pore activity is quantified by the amount of dye taken up in labeled white blood cells treated with the P2X$_7$ agonist relative to labeled white blood cells in the absence of said P2X$_7$ agonist, said nucleotide receptor P2X$_7$ pore activity being corrected for sample age and by subtraction of nucleotide receptor P2X$_7$ pore activity contributed by nonviable white blood cells.

The instructional material preferably describes the analysis of dye uptake by flow cytometry, wherein said flow cytometry detects labeled white blood cells apart from non-labeled cells and measures intensity of the dye taken up by the labeled white blood cells whereby nucleotide receptor P2X$_7$ pore activity is quantified by the amount of dye taken up in labeled white blood cells in the absence of said P2X$_7$ agonist. The white blood cell-specific label is preferably a phycoerythrin-conjugated anti-CD14 antibody.

In an alternative embodiment, the kit may further comprise an isotonic depolarizing solution for depolarizing the labeled white blood cells wherein the isotonic depolarizing solution comprises glutamate ion with the proviso that sodium and chloride ions and divalent cations are absent from said isotonic depolarizing solution in amounts effective to inhibit P2X$_7$ pore activity. Preferably the dye is a DNA-binding dye having a mass of less than approximately 900 Daltons such as YO-PRO-1.

The P2X$_7$ agonist is preferably selected from 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5' (beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof.

The kit may also comprise a divalent cation in an amount sufficient to deactivate nucleotide receptor P2X$_7$ pore activity in the white blood cells contained within the subject's blood sample wherein the divalent cation is magnesium ion. In alternative embodiment, the kit may further comprise a decision tree which, based on at least the nucleotide receptor P2X$_7$ pore activity measured by said kit, directs a user to a subject-specific clinical pathway of medical intervention for said subject.

Other objects, features and advantages of the present invention will become apparent after review of the specification, claims and drawings.

BRIEF DESCRIPTION OF THE DRAWINGS

FIG. 1A demonstrates the inability to discriminate monocytes by size (forward scatter) and granularity (side scatter) in the presence of an overwhelming number of RBCs and platelets. FIG. 1B shows that mononuclear cells derived after one round of RBC lysis display the characteristic scatter associated with granulocytes, monocytes and lymphocytes. The circle, or gate, denotes the approximate position assumed by monocytes. The shading in panels FIGS. 1A and 1B is reflective of increasing cell number, dark to light. FIG. 1C shows that gated cells express CD14, a monocyte marker. FIG. 1D demonstrates the setting of baseline YO-PRO-1 fluorescence associated with CD14+ monocytes as low as possible to maximize the potential fold increase in the Bz-ATP induced signal.

FIG. 2A shows data from the one individual each with the common 1513 AA and heterozygous AC genotypes, whereas FIG. 2B contains data from one subject with the uncommon CC genotype. Inset panels in FIGS. 2A and 2B are the corresponding data from the PCR product restriction fragment length polymorphism analysis with the endonuclease BseR I.

In FIG. 8A, calibrated flow cytometer settings (see Methods) were each used to acquire 10000 CD14-PE+/PI-events from the same sample and PI vs. CD14-PE dot plot analyses were conducted. Gates indicate viable (CD14-PE+/PI) monocytes. Data represent <12 independent experiments. In FIG. 8B. fixed/predefined flow cytometer settings (see Methods) were each used to acquire 10000 CD14-PE+/PI-events from the same sample and PI vs. CD14-PE dot plot analyses were conducted. Gates indicate viable (CD14-PE+/PI) monocytes. Data represent <12 independent experiments.

FIG. 9A shows the gating strategy for restricting analysis to live (CD14-PE$_{pos}$/PI$_{neg}$) events in assays performed using PBMC . FIG. 9B shows the gating strategy for restricting analysis to live (CD14-PE$_{pos}$/PI$_{neg}$) events in assays performed using whole blood. FIGS. 9C and 9D show the effects of bead-determined compensation on PE versus YO-PRO-1 analysis when restricted to live events. FIG. 9C shows YO-PRO-1 fluorescence measurements using PBMC. FIG. 9D shows YO-PRO-1 fluorescence measurements using whole blood. In FIGS. 9C and 9D, unstimulated YO-PRO-1 labeled monocytes (black) are overlayed with stimulated monocytes (gray) in either ficolled blood if FIG. 9C) or in whole blood (FIG. 9D).

FIG. 13A indicates the effect of peripheral blood age on % viable monocytes (CD14-PEpos/PIneg vs total CD14-PEpos;mean ±SEM; n=8). FIG. 13B shows P2X$_7$ pore activity expressed as the BzATP-induced fold-stimulation of YO-PRO-1 uptake fluorescence with each line representing the time course for a single subject (n=8). FIG. 13C indicates the effect of peripheral blood age on % change in fold stimulation of BzATP-induced YO-PRO-1uptake by live monocytes (CD14-PEpos/PIneg) normalized to the day 0 baseline value for each subject (mean ±SEM; n=8).

FIG. 15A is the fluorescence histogram for YO-PRO-1 PMT. FIG. 15B is the fluorescence histogram for PE PMT. FIG. 15C is the fluorescence histogram for PI PMT.

FIG. 16A shows the calculated fluorescence contribution of YO-PRO-1 to the PE detector signal. FIG. 16B shows the calculated fluorescence contribution of PE to the YO-PRO-1 detector signal. FIG. 16C shows the calculated fluorescence contribution of PE to the PI detector signal. Mean intensities of unlabelled beads in YO-PRO-1 PMT, PE PMT and PI PMT were 1.01 for all PMTs. The spectral overlap of the FITC beads into the PE PMT was compensated to yield a matching intensity of the FITC beads to the unstained beads in that channel. The spectral overlap of the PE beads into the YO-PRO-1 PMT and into the PI PMT was also removed from these detectors until the mean intensities matched the unstained beads in those channels.

FIG. 17A shows the correlation of changes in peak flow to changes in cold symptoms. Cold symptoms were recorded by diary four times a day during the course of the study using the modified Jackson instrument. The average scores at the baseline visits are subtracted from peak values during the acute cold visits. FIG. 17B shows the correlation of changes in peak flow to changes in asthma symptoms. Similarly, asthma symptoms and peak flow were recorded by diary twice a day. For both FIG. 17A and 17B, worst a.m. PEF or symptoms during the acute visits and the average a.m. values at the baseline visits were used. Spearman correlation coefficients are shown.

In FIG. 18A, the change in cold symptoms is plotted against the change in neutrophil counts in nasal lavage fluid. In FIG. 18B, the change in cold symptoms is plotted against the change in neutrophil counts in induced sputum. In FIG. 18C, the change in asthma symptoms is plotted against the change in neutrophil counts in nasal lavage fluid. In FIG. 18D, the change in asthma symptoms is plotted against the change in neutrophil counts in induced sputum. In FIG. 18E, the change in peak flow during the course of a cold is plotted against the change in neutrophil counts in nasal lavage fluid. In FIG. 18F, the change in peak flow during the course of a cold is plotted against the change in neutrophil counts in induced sputum. For all of FIGS. 18A-18F, Spearman correlation coefficients are shown.

DETAILED DESCRIPTION OF THE INVENTION

I. In General

Figure 1:
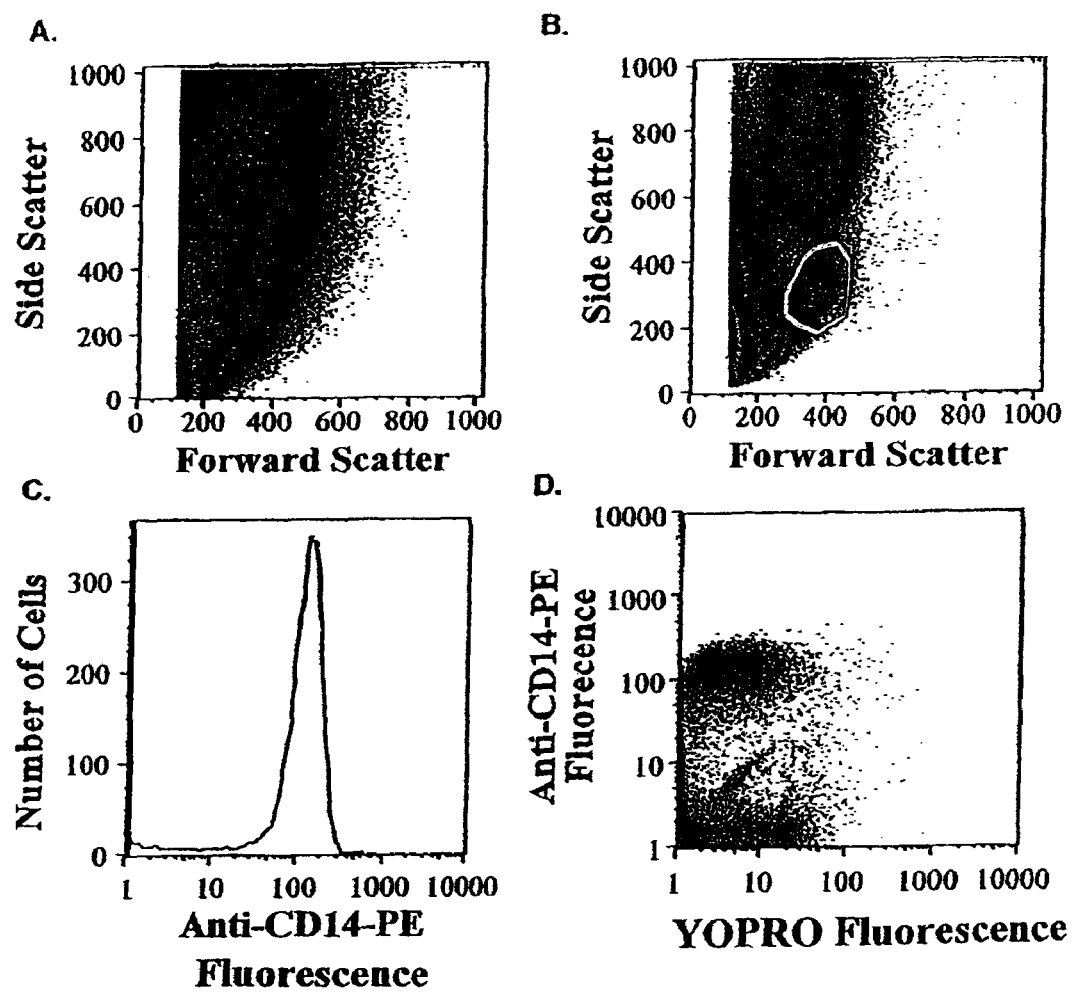
FIGS. 1A-1D display data related to derivation of instrument settings for the washed whole blood pore assay.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention that will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986).

Terms and abbreviations used throughout include:

"2-MeS-ATP" refers to 2-methylthio-adenosine triphosphate.

"Allele" refers to different copies of the same gene within a population that contain small differences in DNA sequence, usually resulting in functional variability.

"Anti-inflammatory cytokine" refers to an immune cell-derived protein that down regulates the effects of inflammatory cytokines, promotes immune cell differentiation, and assists in antibody generation. Examples include interleukin-4, IL-6, and IL-10.

"Bacteremia" refers to a bacterial infection of the blood.

"Bz-ATP" refers to 2',3'-O-(4-benzoyl)benzoyl-adenosine triphosphate.

"CD14" refers to a glycosylphosphatidyl inositol-linked cell surface protein expressed on monocytes and macrophages that acts as a high affinity receptor for LPS.

"Clinical outcome" refers to an observed result or consequence of medical treatment provided to a patient.

"Genotype" refers to the genetic sum of all alleles of a particular gene contained on all chromosomes leading to homozygous of heterozygous states. For example, if there is one copy of a gene per chromosome and two alleles in a population, there can be three genotypes A/A, A/B, and B/B.

"Hardy Weinberg equilibrium" refers to a genetic principle that allows for the prediction of the frequencies of genotypes within a population given the allele frequency. For example the genotypic frequencies of a monogenic trait with two alleles can be predicted by using the formula $f=a^2+2ab+b^2$, where a and b are the allele frequencies. These calculations allow for a determination of recruitment bias within a sample of a population.

"Inflammatory cytokine" refers to an immune cell-derived protein that promotes local and systemic responses to infection including the recruitment of inflammatory cells and/or direct microbicidal activity. Overabundance of these cytokines is associated with vascular damage resulting in the capillary leakage leading to septic shock. Examples include tumor necrosis factor-alpha (TNF-alpha), interleukin-1beta (IL-1beta), IL-12, and interferons.

"LPS" refers to lipopolysaccharide, the major glycolipid constituent of the outer leaflet of the outer membrane of Gram-negative bacteria.

"Locus" refers to a region of DNA containing multiple genes that is co-inherited.

"Monocyte" refers to a peripheral blood mononuclear cell that produces inflammatory and anti-inflammatory cytokines in response to LPS.

"Macrophage" refers to phagocytic cells derived from monocytes that are found in tissue compartments, also a major source of cytokine production.

"$P2X_7$" refers to the seventh member of the P2X family of nucleotide receptors, a multimeric nonselective cation channel that can also form a large pore allowing passage of molecules smaller than 900 Da.

"Phenotype" refers to observed variation in characteristics that result from the interactions of an organism's genotype and its environment.

"Prognosis" refers to a prediction of a probable course and outcome of a disease.

"Septic shock" refers to hypotension and organ failure as a result of immune system dysfunction in the presence of an overwhelming infection, usually accompanied by fever, tachycardia, tachypnea, and leukocytosis. Severe sepsis is thought to be a precursor to septic shock consisting of the above manifestations with hypotension or organ failure (not both).

"Single nucleotide polymorphism" or "SNP" refer to an allelic difference that occurs as the result of a change in a single base pair within the gene in question.

As used herein, "subject" or "patient" shall refer to a mammal, preferably but not limited to a human.

"TLR4" refers to the Toll-like Receptor 4, the major transmembrane signaling component of the CD14-dependent LPS receptor system.

II. The Invention

The present inventors have focused on disorders that arise from aberrant tissue responses to inflammation that may be traced to polymorphisms within genes encoding and regulating cytokine mediators. The inventors' overall aim is to identify alleles in distinct constituents of the host immune response that, as deleterious markers of the risk and severity of sepsis, may be of value in guiding immunosuppressive and anti-infectious therapy based on genetic idiosyncrasy. Accordingly, the inventors have analyzed polymorphisms in the monocyte purinergic receptor $P2X_7$ with a newly devised functional pore assay disclosed and claimed herein.

Availability of an improved pore assay according to the present invention has several immediate impacts from the genomic perspective. First, it enables genomic data from distinct ethnic groups to be compared in international laboratories lacking access to the more challenging and costly method which has been previously described (Gu et al., 2001). This type of phenotypic data is critical to accurate interpretation of a given mutation within diverse genetic backgrounds. Second, the improved pore assay serves as a compass pointing to the identification of, for example, polymorphisms valuable as prognostic determinants in potential patient populations. In this regard, examples set forth below describe volunteer human subjects who exhibit reduced $P2X_7$ pore activity despite homozygous or heterozygous absence of two known mutations, suggesting that additional functionally important $P2X_7$ mutations remain to be discovered. Indeed, description of such additional mutations whose identification was made possible by the present invention is provided below. Third, the improved pore assay serves as an essential tool bridging the gap between the laboratory bench and the bedside. Because of its capacity to integrate the influence of environmental factors and polymorphisms at other loci, a molecular phenotype improves the predictive value of personal genomic data within a host-specific context (i.e., a prognostic determinant).

The clinical validity of any proposed genomic test rests on how well the polymorphism predicts the trait of interest. Oftentimes the gene is expressed in an inaccessible tissue (i.e. the nervous system or heart muscle) and only proxy phenotypic data is available to researchers and clinicians. To the contrary, in the present circumstance the $P2X_7$ receptor is expressed within circulating elements of the blood readily available from all patients. Therefore, the invention provides the capacity to correlate raw clinical data with genomic and pore assay results to sharply refine corollary diagnostic and management pathways of optimal benefit to individual patients.

Therefore, the present invention in one embodiment provides a rapid method of assaying nucleotide receptor $P2X_7$ pore activity in white blood cells. The method is particularly suited for practice in the clinical setting and includes the steps of: (a) labeling white blood cells with a white blood cell-specific label; (b) depolarizing the labeled white blood cells in an isotonic depolarizing solution; (c) contacting the labeled white blood cells with a dye and a $P2X_7$ agonist in an amount sufficient to activate nucleotide receptor $P2X_7$ pore activity; (d) contacting the labeled white blood cells of step (c) with a divalent cation in an amount sufficient to deactivate nucleotide receptor $P2X_7$ pore activity; and (e) analyzing dye uptake in labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of the $P2X_7$ agonist.

In a preferred embodiment, the white blood cell label is an antibody directed against surface antigen CD14. Because $P2X_7$ is expressed on all white blood cells, it is conceivable that any leukocyte cell surface protein could be labeled with an antibody or equivalent white blood cell-specific reagent. For detection purposes to be described below, a fluorescent conjugate to the antibody is utilized. A preferred fluorescent conjugate is phycoerythrin. An essential feature of the invention is that the conjugate must be bright enough such that the labeled cells can be resolved against the background contributed by the unlabeled cells. Without this separation, the signal from the labeled cells becomes lost in the noise contributed from the overwhelming number of red blood cells and platelets, which are in excess by a factor of 1,000 to 100,000 in whole blood samples.

The compound 2'-3'-O-(4-benzoylbenzoyl)-adenosine 5'-triphosphate, called Bz-ATP, is a preferred $P2X_7$ agonist because it is the most potent and efficacious $P2X_7$ agonist known. Others include, but are not limited to, adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5'(beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof. Because pore activity is a relatively unique property of $P2X_7$ function, other agonists could be used, not named herein, provided that they are able to facilitate pore formation.

$P2X_7$ is a nonselective cation channel that allows agonist-dependent passage of sodium, potassium and calcium. After brief stimulations (i.e., greater than or equal to one second), removal of the agonist is associated with cessation of these nonselective currents with minimal desensitization, such that repetitive, brief agonist applications do not attenuate the maximum achievable current amplitude. Longer applications of agonist allow passage of cations with progressively larger diameters. The pattern of time constants associated with the passage of increasingly large cations is not consistent with a model of simple diffusion, suggesting that the channel diameter dilates with chronic administration of agonist. "Pore activity" is defined as the passage of larger molecules, including fluorescent dyes, with an upper mass limit of approximately 900 daltons. The process associated with pore dilation requires at least a few seconds of agonist administration, is reversible upon agonist removal, and is modulated by temperature, as well as the concentrations of sodium, chloride and divalent cations in the extracellular solution.

To maximize the signal obtained from the white blood cells of an individual with two normal copies of the $P2X_7$ gene, the pore assay includes a unique and previously undescribed step in which an isotonic depolarizing solution is contacted with the labeled white blood cells. The isotonic depolarizing solution utilized herein is a solution lacking sodium and chloride ions and divalent cations in amounts effective to inhibit $P2X_7$ pore activity. This reagent is preferably a solution comprising glutamate ion (e.g., a potassium glutamate buffer). This novel step provides a greater separation of the signal obtained from wild type individuals compared to those with mutations. The unique feature here is the absence of extracellular sodium, and to a lesser extent, chloride, because these ions inhibit pore activity. Facilitation of pore activity is further done in the absence of divalent cations that also inhibit pore activity.

Because dilation of the pore allows for passage of large molecules with masses of greater than 900 daltons, fluorescent dyes of several varieties and specificities may be used in the method of the present invention provided that they can fit through the pore. YO-PRO-1 is a preferred macromolecule DNA-binding dye because when activated it has a very intense signal. The key feature here is that the dye must provide a signal brighter than the background contributed by the antibody-labeled white cells in the presence of the dye, but the absence of the $P2X_7$ agonist. The dye preferably provides a signal at least ten times brighter than the background contributed by the antibody-labeled white cells in the presence of the dye but the absence of the $P2X_7$ agonist.

In a preferred embodiment, magnesium ion, preferably provided as a $MgCl_2$ solution, is added at a defined time in an assay according to the invention to close the pore, and add precision and the ability to automate the assay. This step is not contemplated by previous methods of assaying $P2X_7$ pore activity but provides a significant technical advantage to the present method. Other divalent cations may also be used, provided that they do not induce clotting of the solutions containing whole blood.

In a preferred embodiment, dye uptake in step (e) is measured by flow cytometry. Flow cytometry detects labeled white blood cells apart from non-labeled cells and measures intensity of the dye taken up by the labeled white blood cells whereby nucleotide receptor $P2X_7$ pore activity is quantified by the amount of dye taken up in labeled white blood cells treated with the $P2X_7$ agonist relative to labeled white blood cells in the absence of said $P2X_7$ agonist.

The preferred flow cytometry parameters will now be described. Cells from whole blood (i.e., red/white blood cells and platelets) are analyzed on a flow cytometer (available from Becton Dickinson, San Jose, Calif., under the trade name FACSca) calibrated daily using standard fluorimetric beads. The instrument settings were derived using purified blood monocytes that had been separated from the red cells and stained with a phycoerythin-conjugated anti-CD14 antibody in the presence and absence of YO-PRO. The intensity of the YO-PRO signal creates a significant amount of spectral overlap into the phycoerythrin detector. This overlap is electronically subtracted so that phycoerythrin negative events that incorporate YO-PRO can be conveniently distinguished from positively labeled white blood cells. The phycoerythrin signal is collected with a 585 nm filter with a 42 nm band pass, whereas the YO-PRO signal is collected with a 530 nm filter and a 30 nm band pass. Using the results from the purified monocytes, the instrument is then adjusted to trigger on the phycoerythrin signal by setting the threshold above the background associated from unlabeled cells. Thus, data from all non-phycoerythrin labeled cells are omitted. Because the YO-PRO signal is intense, channel compensation is used to eliminate the YO-PRO signal in the phycoerythrin channel.

For each experiment with whole blood, the standard instrument settings are called up from a stored file and used without adjustment. To correct for any slight variation in the flow cytometer's performance, fluorescent standard beads may be analyzed as is standard technique in the field. To reduce viscosity, the whole blood is diluted 1:4 in a standard saline solution. Ten thousand phycoerythrin-labeled events are acquired using CellQuest acquisition and analysis software (Becton Dickinson) and the amount of YO-PRO taken up by these cells is measured in the presence or absence of prior stimulation with the $P2X_7$ agonist, Bz-ATP.

The present invention is also a method of assaying nucleotide receptor $P2X_7$ pore activity in a blood sample including white blood cells, comprising the steps of: (a) labeling white blood cells included within the blood sample with a white blood cell-specific label; (b) depolarizing the labeled white blood cells in an isotonic depolarizing solution; (c) contacting the labeled white blood cells with a $P2X_7$ agonist in an amount sufficient to activate nucleotide receptor $P2X_7$ pore activity and a dye; (d) contacting the labeled white blood cells of step (c) with a divalent cation in an amount sufficient to deactivate nucleotide receptor $P2X_7$ pore activity; and (e) analyzing dye uptake in labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of said $P2X_7$ agonist.

Figure 6:
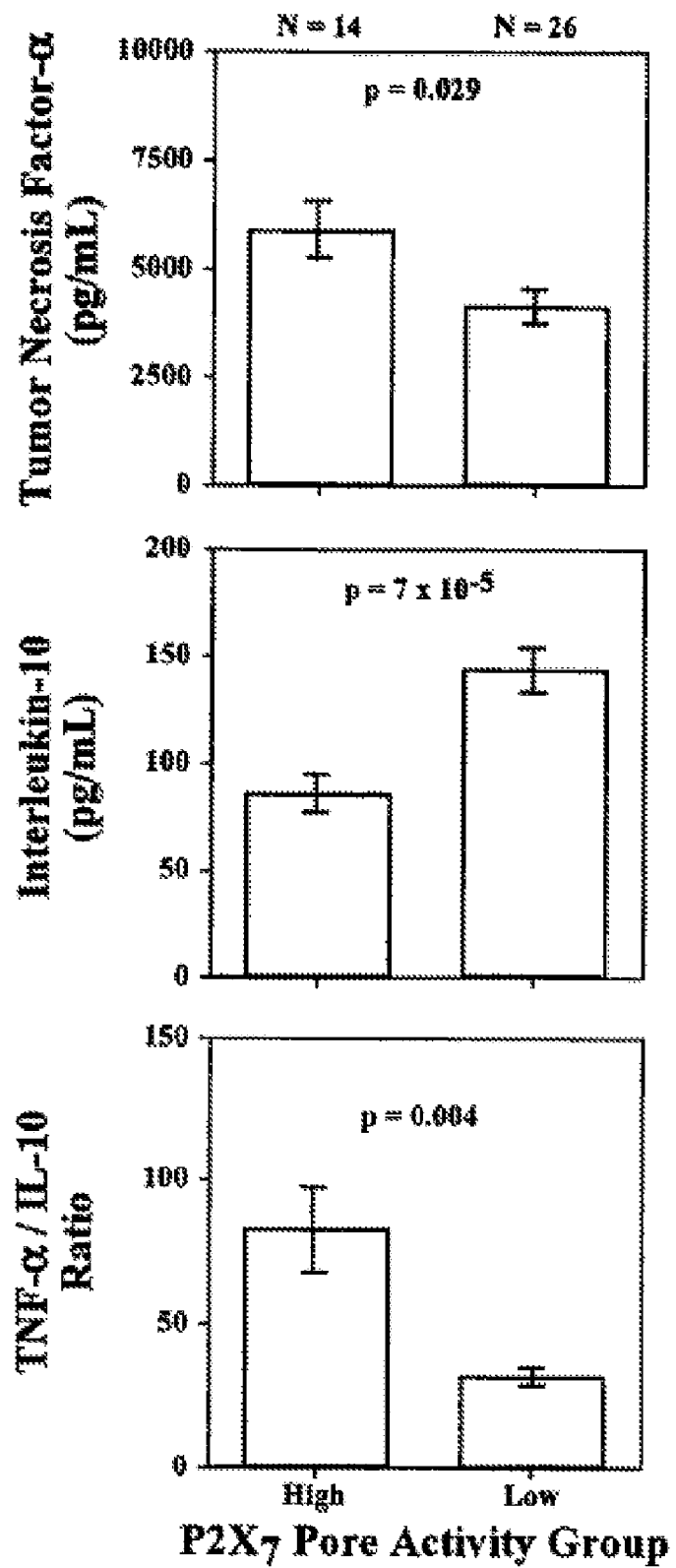
FIG. 6 shows LPS-stimulated whole blood production of tumor necrosis factor-α and interleukin-10. Whole blood samples from Phase II subjects were stimulated for 6 hr at 37° C. with 0 or 100 ng/mL of *Salmonella typhimurium* LPS followed by centrifugation to harvest plasma. The control samples contained undetectable levels of these cytokines. Data shown are the group means and standard errors from fourteen and twenty-six subjects per group (high vs. low pore activity). The results are representative of two experiments seen using a sandwich ELISA and a cytokine array from Pierce Biotechnology, Inc. under the trademark SEARCHLIGHT. The TNF-α to IL-10 ratio was calculated on an individual subject basis prior to deriving group means and standard errors. Results from unpaired Student's t-tests with adjustment for unequal variance are also shown.

Because of the well-known links between monocyte $P2X_7$ pore activity and IL-1 beta processing, the identification of deficient pore activity will correlate with lowered plasma levels of IL-1 beta. This has recently been demonstrated at early time points (Sluyter et al. J. Immunol. 172:3399-3405 (2004). Additionally, the present inventors have recently shown that subjects with low $P2X_7$ pore activity relative to wild type controls have a reduced TNF-alpha to interleukin-10 ratio in response to LPS-treatment of whole blood (FIG. 6). The capacity to quickly ascertain this information, particularly in the clinical setting, allows medical practitioners to predict a particular subject's susceptibility to, for example, sepsis or septic shock and response to varied courses of treatment. Prior $P2X_7$ pore assay techniques did not allow this abbreviated turn around time from sample collection to results, so crucial to patient care in the fast-paced clinical setting. It should be noted that sepsis is only one particular area where molecular phenotype data regarding the $P2X_7$ pore activity is useful as a prognostic determinant, as will be further explored below.

Therefore, in yet another embodiment, the invention provides a method of identifying a nucleotide receptor $P2X_7$-related molecular phenotype useful as a prognostic determinant of a clinical outcome in a patient, comprising the steps of: (a) carrying out a pore assay according to the invention on white blood cell samples from a patient population having known clinical outcomes to determine a plurality of receptor $P2X_7$ pore activities; and (b) correlating the nucleotide receptor $P2X_7$ pore activities with the known clinical outcomes to determine statistically significant correlations between respective pore activities and known clinical outcomes thereby determining a particular nucleotide receptor $P2X_7$ molecular phenotype useful as a prognostic determinant in a patient.

A wide variety of clinical studies are made possible by rapid pore assays according to the present invention. For example, patients who develop septic shock may be examined using the present invention to determine if they have a different $P2X_7$ A1513C allele distribution than intensive care unit (ICU) control patients, and consequently whether this is a major predictor of variance in endogenous cytokine profiles. This will identify $P2X_7$ genotype frequencies in patients with septic shock relative to ICU control patients and correlate these frequencies with the cytokine profile detected from unstimulated (ex vivo) whole blood by techniques known in the art. With these endpoints and estimated frequencies from the current data set in healthy subjects, a sample size of one hundred and fifty patients in each group will provide sufficient statistical power to detect significant differences. Other variables to be included in the regression models would be confounding SNPs at other loci (e.g. the LPS receptor system, CD14/TLR4) and clinical parameters (comorbid conditions, source of infection, class of organism, etc). Adjustments for multiple comparisons would be taken into account up front to help limit the number of parameters entered into the regression models. An expanded version of this trial could be coupled with a multi-center trial of an intervention protocol vs. standard of care, enrolling five hundred or more septic patients. The hypothesis in this case is that patients with low $P2X_7$ pore activity conferred by the $P2X_7$ 1513 C/C genotype or other genotypes who develop septic shock have a worse prognosis with respect to length of stay in the ICU and/or mortality. Similar considerations for regression modeling as discussed above would also pertain to this trial.

It should also be noted that the $P2X_7$ receptor is a key player in the processing and release of interleukin (IL-1), and that a loss of the function allele (1513-C) has recently been associated with enhanced survival is sepsis occurring in bone-marrow transplant patients (Lee et al., Haematologica, 92:651-657 (2007). Further, given that $P2X_7$ not only regulates the immune response to Gram negative bacteria and *Mycobacteria*, but also regulates the immune response to Gram positive bacteria, respiratory viruses, and trypanosomes, in an alternative embodiment of the invention, the $P2X_7$ receptor provides a global immune response regulator (Denlinger et al. Am. J. Respiratory & Critical Care Medicine, in press (2008), Kahlenberg et al., J. Immunology, 175: 7611-7622 (2005), Mariathasan et al., Nature 440:228-232 (2006), Mantuano-Barrada et al., Microb. Infection, 5:1363-1371 (2003).

Finally, because the surface expression and pore activity of $P2X_7$ in monocytes may depend upon the C-terminal lipid interaction motif that binds LPS, the whole blood pore assay may be an early predictor of bacteremia in patients with an infection, and subsequent progression to septic shock, and thereby serve as a prognostic determinant. Developing this concept directly utilizes information obtained from the $P2X_7$ structure/function analysis. As an example, the current protocol for the pore assay described above with results depicted in, for example, FIG. 4, is intentionally designed to be highly sensitive in the detection of C/C mutants, at the expense of being less specific for subjects with the A/C or A/A genotypes. Using different agonist and buffer systems, the capacity to open the pore in monocytes can be dampened significantly, such that a normal response even with the A/A genotype is quite diminished. These conditions make it possible to detect monocytes from bacteremic patients that have greater surface localization of $P2X_7$ and hence supranormal levels of pore activity. The two sets of assay conditions could be used in parallel such that there is discrimination between current patient physiology and total capacity for monocyte pore formation. The targeted potential patient population for study in this case would be noncritical hospital patients with infections, as a way to identify those with increase risk of becoming septic. As early diagnosis and implementation of supportive therapy for patients with septic shock has been shown to improve patient outcomes (3), this type of rapid diagnostic test can serve as the ultimate translation of bench research.

Rapid assays according to the present invention will thusly be used to, for example, identify more specific ways to prospectively stratify patients with severe sepsis and septic shock by understanding the genetic and molecular contributions of the nucleotide receptor $P2X_7$ on monocyte and macrophage functionality (i.e., the identification of prognostic determinants). In addition to sepsis-related studies, the present invention will be useful in the ex vivo analysis of $P2X_7$ pore activity in regard to other problematic infections including those infections caused by or related to, for example, *Staphylococcus aureus, Pseudomonas aeruginosa* and *Blastomyces* (i.e. the effect of organisms lacking endotoxin on pore activity and cytokine profiles).

The use of the present invention for screening the variability in $P2X_7$ function is also envisioned to allow the rapid and convenient collection of preliminary data for potential patient populations such as those suffering from tuberculosis, asthma, pneumonia, urosepsis, rheumatoid arthritis, lupus, Crohn's Disease, ulcerous colitis, parasitic infections (e.g., leishmaniasis), transplant rejection or chronic lymphocytic leukemia (CLL), acute or chronic forms of axonal injury and neurodegenerative disorders. Regarding CLL, Wiley et al. (*Lancet* 359, 1114-1119 (2001) reported that the frequency of the non-functional 1513C allele was greater in a series of patients with indolent CLL than in normal individuals. They also studied the occurrence of the 1513A to C polymorphism in two pedigrees with familial CLL, and found affected members of these families to be either heterozygous or homozygous for the 1513C allele. Wiley et al suggested that loss of $P2X_7$ function produced an antiapoptotic effect and contributed, along with the overexpression of the BCL2 gene, to the accumulation of leukemic B cells in the circulation. They also suggested that genetic haploinsufficiency of $P2X_7$ might contribute to the well-recognized familial incidence of CLL. As can be appreciated by one of skill in the art, a rapid pore assay would provide an additional clinical tool in diagnosing patients suffering from CLL or with a predisposition to CLL.

With respect to an infectious process, Lammas and colleagues found that the C allele of a $P2X_7$-762 promoter polymorphism was associated with a lower incidence of smear-positive pulmonary tuberculosis in a Gambian population (Li et al., (2002) J. Infect. Dis. 186:1458-62). Although neither this nor four other promoter polymorphisms appear to affect surface $P2X_7$ expression (Li et al., (2002) FEBS Lett 531: 127-31) this receptor has been shown to have a large intracellular pool that promotes phagolysosomal maturation needed to facilitate killing of *Mycobacteria tuberculosis* (Fairbairn et al., (2001). J. Immunol. 167:3300-7, and Lammas et al., (1997) Immunity 7:433-44). Thus, if the −762 C allele is associated with enhanced mRNA and/or protein trafficking, these individuals may be better able to clear the initial infection such that they do not progress to active disease. In addition, individuals with the $P2X_7$ 1513 CC genotype have monocytes that are less able to kill the BCG strain of *M tuberculosis* (Saunders et al., (2003) J. Immunol. 171:5442-6). Thus, individuals with loss-of-function $P2X_7$ alleles may also be at risk for a worse outcome in the setting of certain types of infection, such as those from intracellular pathogens.

In light of the above, the pore assay provided herein is integral in the identification and correlation of $P2X_7$ pore activities and underlying-alleles with clinical outcomes so that reliable prognostic determinants may be identified. Such prognostic determinants will provide the knowledge to allow refining of immunomodulatory or immunosuppressive as well as anti-infectious therapy on a patient-by-patient basis. Thus, a further embodiment of the invention is directed to a method of identifying a nucleotide receptor $P2X_7$-related polymorphism useful as a prognostic determinant of a clinical outcome in a patient, comprising the steps of: (a) carrying out a pore assay according to the invention on white blood cell samples from a patient population having known clinical outcomes to determine a plurality of respective receptor $P2X_7$ pore activities; (b) correlating the nucleotide receptor $P2X_7$ pore activities with the known clinical outcomes to determine statistically significant correlations between respective pore activities and known clinical outcomes; and (c) characterizing genomic material from respective patients in which statistically significant correlations were identified in step (b) to identify a nucleotide receptor $P2X_7$-related polymorphism useful as a prognostic determinant.

It is envisioned that $P2X_7$ gene polymorphisms, identified through application of the present invention, may be collected to create a database upon which future medical detection techniques will be based. For example, $P2X_7$ gene polymorphisms in an individual patient may be rapidly assayed in the future by the preparation and use of DNA microarray assays. In general, such assays utilize a series of oligonucleotide or cDNA probes affixed to a solid support. The probes are designed to be unique to a given SNP or mutation. The DNA template of interest is then contacted with the DNA microarray and $P2X_7$ hybridization is detected. In one embodiment, such assays will utilize gene "chip" substrates having affixed probe nucleic acids (e.g., oligonucleotides or cDNAs) representing $P2X_7$ gene polymorphisms from an above-described database. A nucleic acid sample from the patient may be incubated with the gene chip substrate under conditions favorable for the specific hybridization of the sample nucleic acids with their complementary probe sequences affixed to the gene chip substrate. After incubation, all non-hybridized sample nucleic acids are removed from the sample nucleic acid:probe hybrid.

The presence of nucleic acids which have hybridized, if any such molecules exist, is then detected using standard techniques well-known to those in the art. The probe gene sequence(s) to which the sample nucleic acids have hybridized can be compared to the hybridization pattern expected from a wild type $P2X_7$ gene sequence in order to determine whether a $P2X_7$ gene polymorphism is present. Based upon known correlations between $P2X_7$ gene polymorphisms and clinical outcome, medical practitioners may then be directed to a patient-specific clinical pathway. Microarray technologies amendable for accessing $P2X_7$ gene polymorphisms include, but are not limited to, the inventions disclosed in: U.S. Pat. No. 5,837,832 to Chee et al.; U.S. Pat. No. 5,837,832 to Nerenberg et al., assigned to Nanogen, Inc.; and U.S. Pat. No. 6,355,431 to Chee et al. Other technologies understood in the art to facilitate polymorphism detection are also amendable for use in such approaches and include, for example, the proprietary platform available from Third Wave Technologies, Inc., under the federally-registered trademark INVADER.

The invention also encompasses a method of providing immunosuppressive and anti-infectious therapy to a patient, comprising the steps of: (a) analyzing a white blood sample from the patient by a pore assay as described herein to obtain a nucleotide receptor $P2X_7$ pore activity for the patient; and (b) comparing the nucleotide receptor $P2X_7$ pore activity with previously-determined nucleotide receptor $P2X_7$ pore activities that demonstrate statistically significant correlation to clinical outcomes; and (c) based upon the result of step (b), providing therapy to either avoid or achieve a particular clinical outcome in the respective patient.

In still another embodiment, this invention provides kits for practice of the methods described herein. The kits will include instructions and, optionally, any reagents and/or apparatus to facilitate practice of the methods. For example, a kit may include buffer solutions, positive and/or negative controls, or calibration standards. In one preferred embodiment, the kits comprise operational instructions and one or more containers containing the necessary stock or working solutions to carry out the present invention. Kits may be directed to determining a molecular phenotype (i.e., pore activity) or a genotype (e.g., a known or unknown SNP).

The kits include instructional materials containing directions (i.e., protocols) for the functional use of the kit, and, optionally, for interpretation of test results. Preferred instructional materials provide protocols utilizing the kit contents for measuring $P2X_7$ pore activity in a blood sample. Any medium capable of storing instructional materials and communicating them to an end user is contemplated by this invention. Such media include, but are not limited to printed media, electronic storage media (e.g., magnetic discs, tapes, cartridges, chips), optical media (e.g., CD ROM), and the like. Such media may include addresses to internet sites that provide such instructional materials. In addition, certain kit embodiments may contain algorithms or decision trees pointing to subject-specific clinical pathways (i.e., best practices) based on kit-facilitated test results. For example, if in a subject with clinical presentation X, and genotype Y, pore assay result Z is observed, then clinical pathway I is recommended. Conversely, if in a subject with clinical presentation A, and genotype B, pore assay result C is observed, then clinical pathway II is recommended. These examples set forth the manner in which instructions provided in a kit according to the invention may guide the construction of patient specific algorithms that cannot be traversed in advance of obtaining a pore assay result.

As described herein, the steps of preparing a plurality of pore assays according to the invention include an appreciable number of iterative steps where large sample numbers are to be processed, as would be anticipated in the clinical setting. The invention's lack of complex purification steps and unique manipulation of pore activity by specific reagents (e.g., divalent cation added to halt pore activity) make the present methods especially well suited to automation of one or more of each of its steps. It is therefore envisioned that the invention may be performed by any automated means including those containing a computer-readable medium carrying a sequence of instructions, where executing the sequence by a processor causes the processor to direct the steps of the method. An example of an automated means suitable for automating one or more of the present invention's steps is disclosed in U.S. Pat. No. 6,326,147 to Oldham et al.

It is further envisioned that the present invention may be carried out in a micro-titer plate format. In an embodiment based thereon, wells within a micro-titer plate would be coated with, for example, anti-CD14 antibodies. In a single well, whole blood, an isotonic depolarizing buffer, dye and +/− agonist would be mixed followed after a time period by addition of a divalent cation. Following a washing step which would eliminate cell types not bound by the anti-CD14 antibodies (e.g., red blood cells and platelets), dye uptake would be quantified by a fluorimetric plate reader to determine a $P2X_7$ pore activity.

The inventors estimate a pore assay according to the invention (e.g., as described in Example 1 below) may be manually carried out in as little as two hours from blood collection to data analysis, drastically less than the analysis intervals required by previous techniques, and automation may further minimize the necessary time involved.

As well, one of skill in the art, after consideration of the invention described herein, will be able to adapt through minimal routine experimentation the present invention for assay of pore activity in a wide variety of channel proteins. Such channels include both $P2X_7$-related channels (i.e., channels in the purinoreceptor family, particularly the P2X subgroup) and channels unrelated in homology to the P2X channels but characterized by similar ionotropic behavior. In addition, the methodology described herein is also amendable for assaying pore activity in cell types other than white blood cells by no more than routine selection of cell-specific label, agonist/antagonist, dye and optimization of flow cytometry parameters based upon the present disclosure.

In another embodiment, the inventors provide a standardized method of cytometric analysis which accounts for variable sample age and instrumentation differences. Flow cytometric analysis of human $P2X_7$ pore activity segregates variant from common $P2RX_7$ genotypes and serves as a biomarker for cancer, pain, inflammation and immune responses to infection. $P2X_7$, a purinergic nucleotide receptor, is increasingly associated with diverse pathological conditions including cancer, pain, inflammation and aberrant responses to infection. This ligand-gated cation channel is encoded by P2RX7, a 55 kB gene with thirteen exons on human chromosome 12q24, and is expressed by all classes of leukocytes studied to date, epithelial cells and select neuronal populations. Current bioinformatics data suggest there is a recombination hotspot in the middle of intron 5, associated with over three hundred and eighty single nucleotide polymorphisms in the region (www.hapmap.org, build 35, accessed May 23, 2007). Consistent with its role in amplification of innate immune responses, genetic association studies link variants of this receptor to the control of *Mycobacterium tuberculosis* in different populations on three continents. To facilitate additional association studies, the inventors developed a genomically validated functional assay to rapidly identify and bridge disparate P2RX7 genetic, phenotypic and clinical results, while also increasing statistical power in the face of sample size constraints.

The assay described herein segregates variants from common $P2X_7$ receptor genotypes/phenotypes by taking advantage of a unique feature of the $P2X_7$ receptor. This feature is the reversible expansion of its selectivity filter following continuous cellular exposure to extracellular nucleotides that results in increased cation ($Ca_{2+}$, $K_+$, and $Na_+$) permeability and the passage of larger molecules (greater than 900 Da), a phenomenon referred to as pore activity.

Using a kinetic functional assay with features expressly designed to segregate samples containing loss-of-function alleles, the inventors identified a threshold of pore activity below which these genotypes are greatly enriched. Specifically, logistic regression analysis with the full range of pore activity data as a continuous variable and a combined binomial variable derived from three well validated loss of function genotypes had a receiver-operator area under the curve of 0.927 (p<0.001). Selecting viable (CD14-PEpos/PIneg) monocytes for the analysis of $P2X_7$ pore activity requires appropriate fluorescence compensation to minimize fluorescence spectral overlap and measure the true emission of each fluorochrome. The optimal threshold of low pore activity was thereby established as 22-fold of BzATP-induced YOPRO-1 uptake over that stimulated by the saline control, where the fold-uptake was defined as the ratio of fluorescence measurements in BzATP- and buffer-treated samples.

The performance characteristics at this threshold for identifying samples with 1513 CC, 1729 TA or 946 GA genotypes were as follows: sensitivity 85%, specificity 91%, positive predictive value 59% and negative predictive value of 98%. For example, a blood sample with normal pore activity (i.e., greater than 22-fold of BzATP stimulated YO-PRO-1 uptake) has a 98% chance of not harboring the three aforementioned loss-of-function genotypes.

Figure 7:
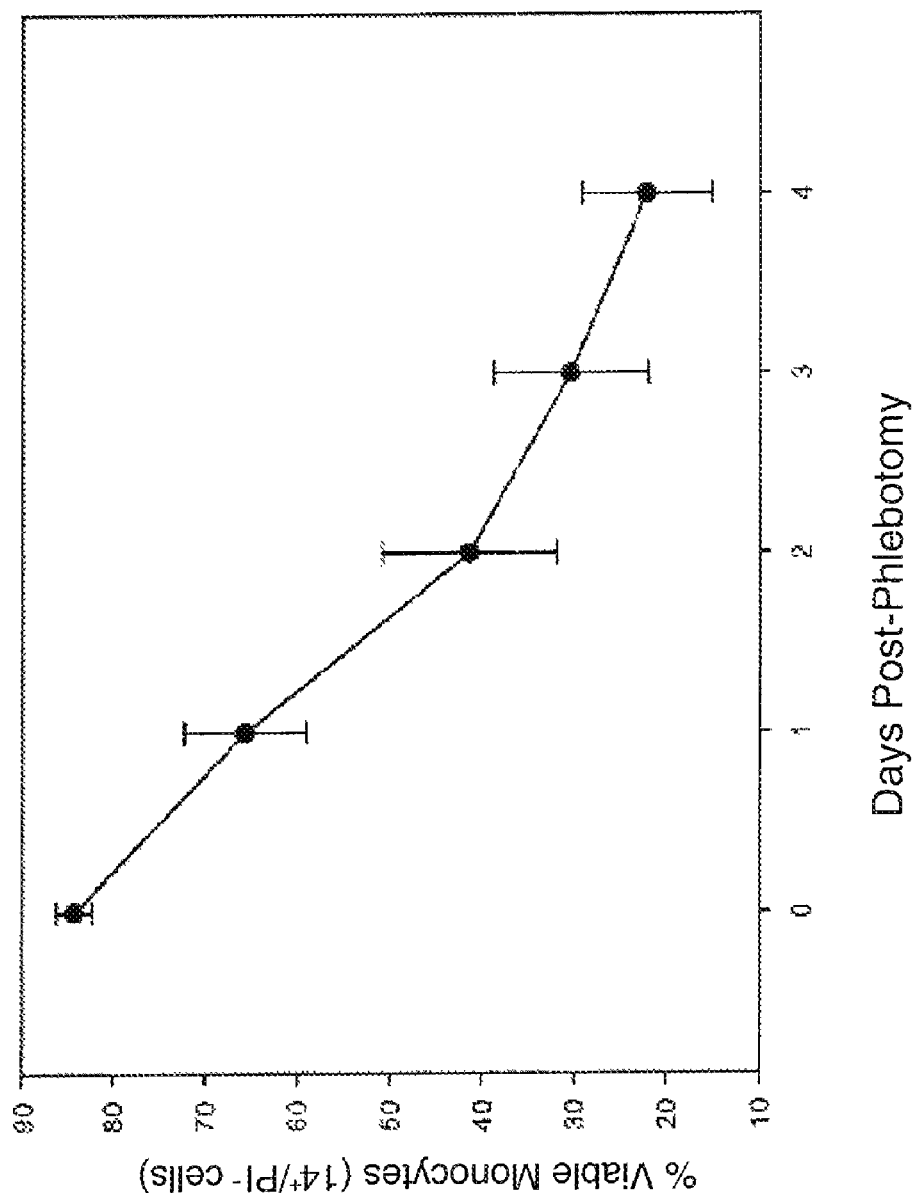
FIGS. 7A and 7B show the effect of monocyte viability on BzATP-stimulated P2X7 pore function. For FIG. 7A, peripheral blood was obtained from eight laboratory volunteers and processed immediately or stored at room temperature for up four days to simulate the conditions of shipping blood from centers around the country. On the day of processing, aliquots of the blood samples were stained and data was acquired using bead-adjusted settings on a FACSCalibur flow cytometer. Data is expressed as % CD14$_{pos}$/PI$_{neg}$ events in the sample (mean+SEM; n=8). For FIG. 7B, anti-CD14-PE labeled human peripheral blood from a representative subject was stimulated with control vehicle or 250 mM BzATP for 20 minutes in the presence of 1 mM YOPRO-1 dye as described in Materials and Methods and beads were used to set the cytometer. Histogram analysis of YO-PRO-1 fluorescence detected in live (dashed or solid outline) and total (light or dark shading) monocyte populations with or without stimulation with BzATP. Arrow indicates the response of dead (CD14-PE$_{pos}$/PI$_{pos}$) monocytes to BzATP.
Figure 7:
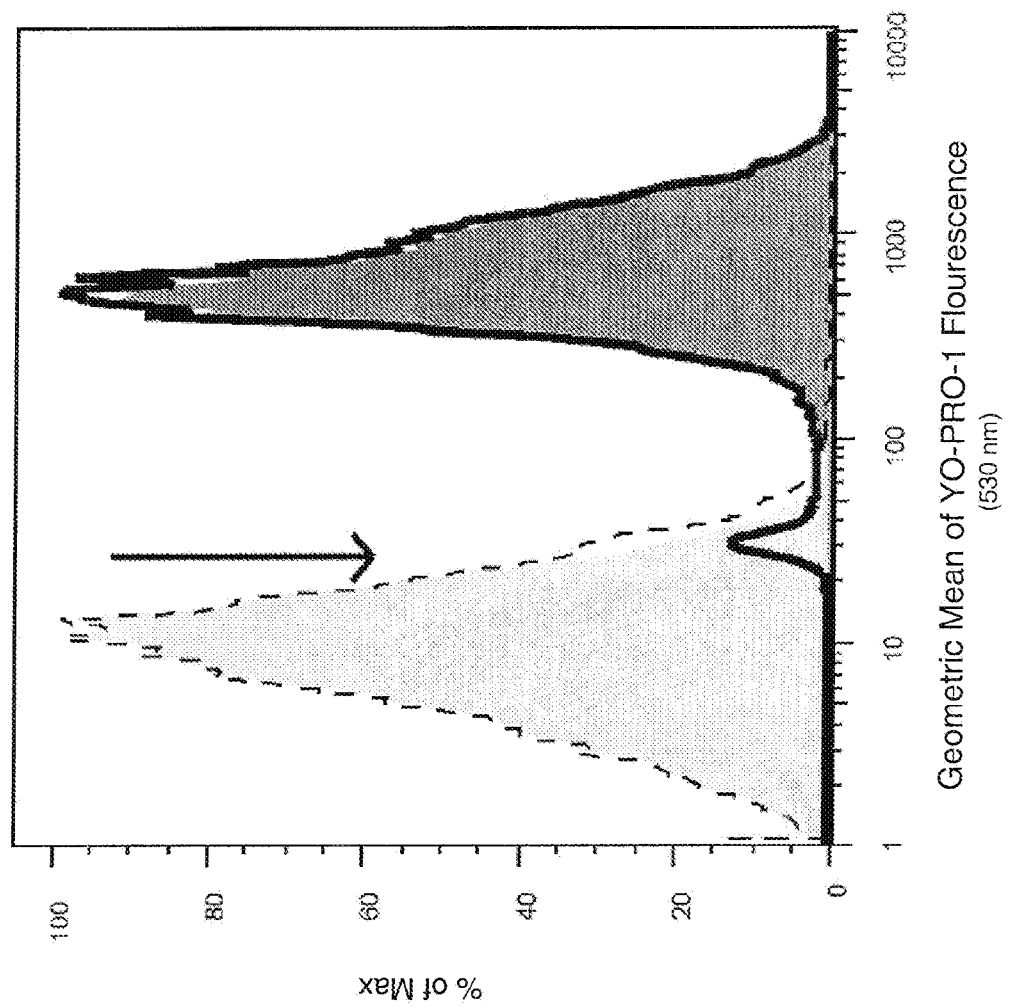

Nucleotide and/or nucleotide analog (e.g. BzATP) interaction with the $P2X_7$ receptor on the cell surface regulates $P2X_7$ pore activity. However, nonviable cells within the total monocyte population likely modulate the measurement of true $P2X_7$ pore function as a result of unregulated YO-PRO-1 uptake due to loss of plasma membrane integrity influencing the basal rate as well as attenuated responsiveness to BzATP stimulation. Accordingly, the present inventors conducted a comparative analysis of BzATP-induced $P2X_7$ pore activity in viable (CD14-PEpos/PIneg cells) versus total (CD14-PEpos) monocyte populations. These results demonstrate that measured $P2X_7$ pore function in total monocytes is significantly attenuated compared to measured $P2X_7$ pore activity in viable monocytes (FIG. 7). Therefore, exclusion of nonviable cells in the analysis of $P2X_7$ pore activity in monocytes is warranted to measure true $P2X_7$ pore function.

Referring to the techniques and results described herein, particularly in Example 4, fluorescent particles were used to standardize instrument settings. The inventors' standardization method described herein was compared to the use of fixed instrument settings. Experiments were performed to evaluate components of systematic variability and to facilitate correction for the effects of sample age. The inventors' assay segregates variant from common $P2X_7$ receptor genotypes/phenotypes by taking advantage of a unique feature of the $P2X_7$ receptor.

Selecting viable (CD14-PEpos/PIneg) monocytes for the analysis of $P2X_7$ pore activity requires appropriate fluorescence compensation to minimize fluorescence spectral overlap and measure the true emission of each fluorochrome. The inventors standardized method uses custom acquisition templates to analyze $P2X_7$ pore activity in viable monocytes through calibration of PMT sensitivities and fluorescence compensation using fluorescent particle standards. The instrument settings are calibrated to evaluate $P2X_7$ pore function by monocytes in human whole blood. As expected, by standardizing instrument settings, data collected on different cytometers (FACScan, FACSCalibur, and LSR II) was consistent and more reproducible than data acquired on cytometers with fixed instrument settings.

Figure 8:
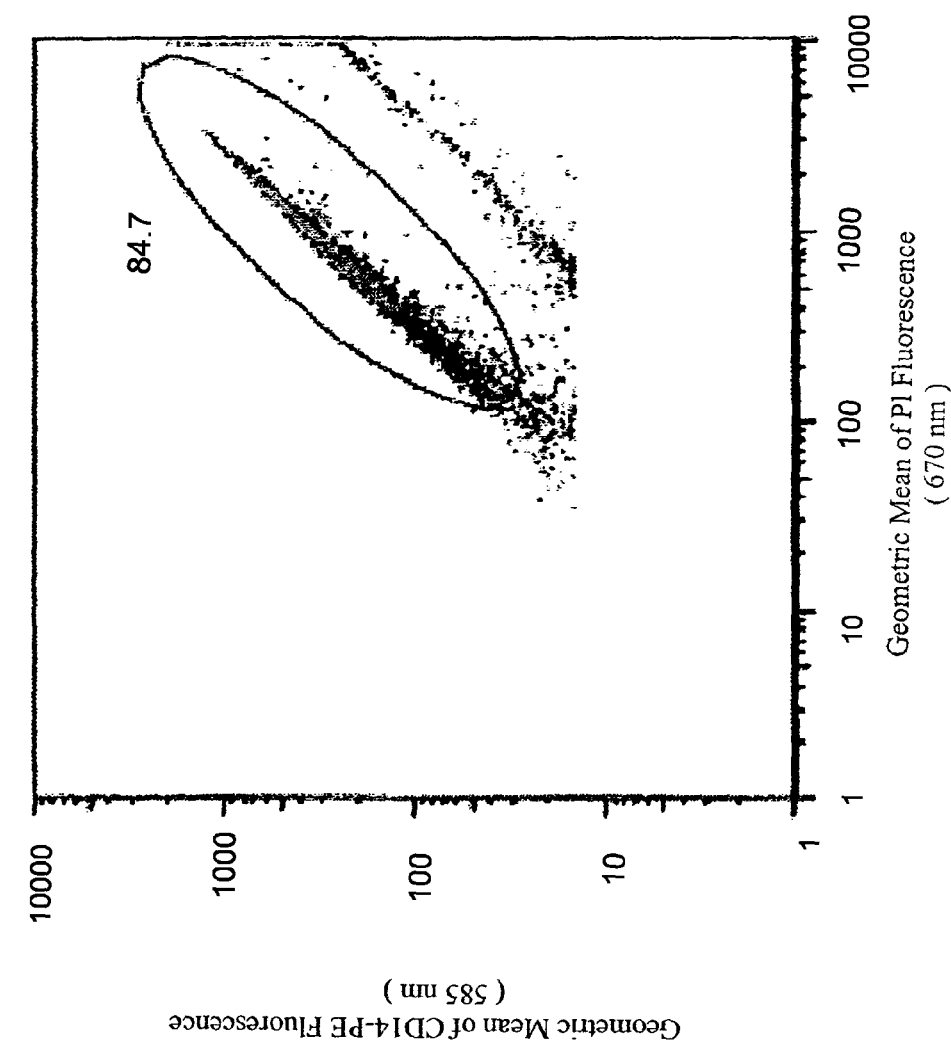
FIG. 8A and 8B show the effect of calibrated vs. predefined flow cytometer settings on acquisition and analysis of viable (CD14-PE+/PI-)monocytes. For both FIGS. 8A and 8B, anti -CD14-PE-labeled human peripheral blood was stimulated with 250 μMBzATP for 20 min in the presence of 1 μMYO-PRO-1 dye and absence of sodium chloride at room temperature, followed by pore closure with 10 μMMgC12 and PI staining for 15 min.
Figure 8:
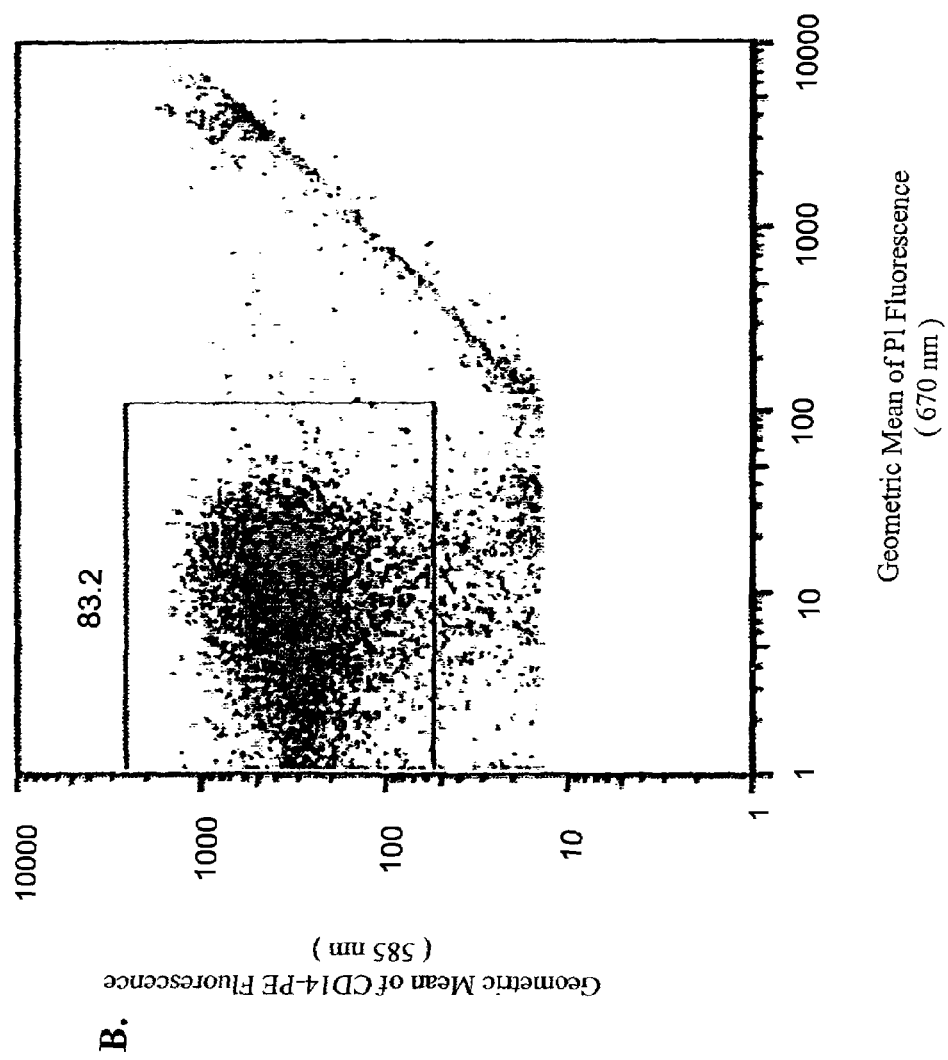

The results indicate that standardized calibration of flow cytometer instrument settings permits optimal selection of viable monocytes for subsequent examination of $P2X_7$ receptor phenotypes (FIG. 8). Moreover, $P2X_7$ pore function results acquired by FACScan using fixed instrument settings trended to be attenuated compared to results acquired by FACScan using standardized instrument settings (data not shown; n=6). These results are likely a consequence of better selection of viable monocytes using the standardized instrument settings compared to the use of fixed instrument settings (FIG. 8), because the inclusion of nonviable cells in the analysis causes attenuation in the measured $P2X_7$ pore function (FIG. 7). Additionally, these data demonstrate that standardized calibration of instrument settings on different instruments provide comparable results with respect to the fold stimulation in BzATP-induced YO-PRO-1 uptake by viable monocytes.

Because the samples are obtained under different conditions and are received at different times after phlebotomy, the inventors' examined the effect of day to day variation in patient samples as well as the effect of sample age on pore activity. The data indicates that day-to-day phlebotomy had no significant effect on $P2X_7$ pore function exhibited by monocytes. Therefore, measurements of $P2X_7$ pore activity by viable monocytes in blood obtained on different days is reliable and any significant variation in $P2X_7$ pore function acquired from an individual on different days may be attributed to a secondary effect. Accordingly, the method of the present invention provides a standardized method with acquisition templates for quantitative detection of $P2X_7$ pore function by monocytes in human whole blood analyzed within four days post-phlebotomy that minimizes inter- and intra-laboratory variation in sample acquisition Interestingly, sample age caused augmentation of $P2X_7$ pore function in monocytes compared to day zero baseline even though a rapid decline in monocyte viability was exhibited throughout the five-day period. The sequential measurement of changes in pore activity with sample age allowed for the derivation of correction factors for samples analyzed at different times. Accordingly, the inventors derived correction factors for sample age on BzATP-induced $P2X_7$ pore function by monocytes and used these values to correct the $P2X_7$ pore function results. Descriptive data from the clinical samples demonstrate that the group median for fold stimulation in BzATP-induced $P2X_7$ pore function by monocytes is increased using and the inventors current standardized calibration method, even after correction for sample age.

Therefore, it is likely that the increase in the group median for fold stimulation in $P2X_7$ pore function by monocytes using the current standardized calibration method is a result, at least in part, of excluding nonviable cells in the present analyses. Whether senescence, hypoxia, or nutritional deprivation are stimuli for enhanced $P2X_7$ protein expression is presently unclear but would be consistent with the ability of this receptor to regulate apoptosis.

The presently described correction for sample age and the exclusion of nonviable cells requires refinement of the receiver-operator curve analysis using results obtained by the present method to accurately segregate variant from common $P2X_7$ receptor genotypes/phenotypes in future studies. Exclusion of nonviable cells increased measurements of $P2X_7$ pore function as assessed by the agonist-induced fold stimulation of YO-PRO-1 uptake. Comparison of three instrument platforms did not show an appreciable effect on variability (ANOVA p=0.78). The coefficient of variance for $P2X_7$ pore activity associated with repeated assessments of the same subject on different days was 0.12±0.02. Standardization of the assay resulted in comparable data despite sample age.

Utilizing this cellular assay, the inventors demonstrated that 19% of individuals residing in the upper Midwest of North America have attenuated monocyte $P2X_7$-regulated pore function. Moreover, the inventors demonstrated an association between loss-of-function $P2X_7$ receptor genotypes to attenuated nucleotide-stimulated $P2X_7$ pore function and an anti-inflammatory cytokine profile by monocytes following in vitro challenge with LPS and nucleotides. Thus, variation in $P2X_7$ receptor pore function is a biomarker for infectious/inflammatory diseases and disorders. Further, although $P2RX_7$ has not previously been referred to as an asthma gene, its chromosomal location is thought to contain numerous such candidates based on linkage in multiple populations to measurements of lung function. Additionally, $P2RX_7$ is thought to control the immune response to infection with *Chlamydia* species, an intracellular pathogen thought to contribute to asthma pathogenesis which is also one of the therapeutic targets for the ACRN-MIA clinical trial, making the assay described herein useful in a wide variety of clinical and therapeutical applications. Nucleotide and/or nucleotide analog (e.g., BzATP) interaction with the $P2X_7$ receptor on the cell surface regulates $P2X_7$ pore activity.

As can be appreciated, the present invention provides in one embodiment, a standardized method for quantitative detection of $P2X_7$ pore function by monocytes in human whole blood examined within four days post-phlebotomy that minimizes intra- and inter-laboratory variation in sample acquisition. Because individuals with reduced capacity for $P2X_7$ pore formation are suggested to be predisposed to an anti-inflammatory cytokine profile in the setting of immune system perturbation, utilization of the novel standardized calibration method described herein facilitates the segregation of variant from common $P2X_7$ receptor genotypes/phenotypes and potentially identifies variation in $P2X_7$ receptor pore function as a biomarker for infectious/inflammatory diseases and disorders. The data also demonstrates that the bead-adjusted setup method of the present invention produces less intra-laboratory variability with recalled settings, particularly when the raw median YO-PRO-1 fluorescence data are presented from BzATP-treated samples. Moreover, the bead-adjusted setup of the present method accommodates processing of samples with varying age by excluding nonviable cells, and produces comparable results when transferred between instruments, suggesting that it may also reduce inter-laboratory differences.

Referring to the techniques and results described in Example 5, the inventors show that the uptake of fluorescent dyes serves as a measure of pore function. Approximately half of adult asthma exacerbations are attributed to respiratory viruses, and this statistic is up to 85% in children. Although most viruses that infect the upper airway can cause exacerbations, rhinoviral exacerbations are felt to be the most frequent and can be among the most severe. The rhinovirus infects epithelial cells of both the upper and lower airway leading to the production of a variety of inflammatory mediators, including IL-1α, IL-1β, IL-6, IL-11, IL-16, TNF-α, GM-CSF, IL-8, GRO-α, ENA-78, RANTES, eotaxin, and MIP-3α, resulting in a predominantly neutrophilic inflammation of the airway.

Rhinoviral infection and/or the subsequent neutrophilic inflammation lead to a variety of pathophysiological consequences important to asthma exacerbations. For example, neutrophils can amplify or alter the inflammatory response through generation of inflammatory cytokines (TNF-α, IL-1α, IL-1β IL-6, IL-12, IFN-α), immunoregulatory cytokines (IL-1Ra, TGF-β), chemokines (IL-8, GROα, GROβ), and angiogenic/fibrogenic growth factors (VEGF, bFGF, HGF, TGF-β). This inflammation results in epithelial injury, which causes edema and exposes neural elements associated with increase cholinergic reflex bronchoconstriction during viral infections. Other changes include an increase in mucus production due to rhinoviral infection of hyperplastic goblet cells and the secretagogue action of neutrophil elastase. Finally, rhinoviral infected neutrophils may be less susceptible to β-adrenergic-dependent inhibition of adherence and chemotaxis. In sum, rhinovirus can infect the upper and lower airway leading to a multitude of effects that are associated with asthma exacerbations.

The severity of this inflammatory response in the lower airway and attributable symptoms is highly variable. Certainly, there is substantial strain variation between the major and minor groups of rhinovirus that lead to differences in the intensity of the infection and inflammatory response. Host factors are also thought to contribute. Data using an experimental infection with RV16 show that differences in the amount of IFN-γ produced inversely correlates with the severity of cold symptoms. Additionally, single nucleotide polymorphisms in the genes encoding CCR-5, surfactant protein D, IL-8, and IL-10 have been shown to be associated for increased risk for exacerbations during viral infection. Moreover, the immune responses due to chronic aeroallergen exposure and/or chronic respiratory tract infection may modulate the response during an acute viral infection. In this light, the inventors demonstrate that half of subjects with a rhinoviral cold do not develop an exacerbation, which has led to an intense search for the risk factors that may synergize with this virus in susceptible individuals.

Numerous lines of evidence support the notion that the human gene P2RX7 modulates the asthma phenotype, particularly in response to airway infection. This gene localizes to a 55 kB locus of chromosome 12q24, a region known to contain multiple asthma genes linked in multiple populations to phenotypes including airway hyper responsiveness to methacholine challenge. It is expressed on respiratory epithelium and by most classes of leukocytes. Bronchial challenge with allergens leads to a luminal release of the ligand for this receptor, extracellular ATP, and there is indirect evidence that this also occurs during naturally occurring viral infections of the lower airway. Stimulation of lung dendritic cells by ATP leads to the production of numerous chemokines and subsequent influx of eosinophils and lyphocytes.

In an additional embodiment, pore function is shown herein as linked to asthma symptoms during a naturally acquired upper respiratory tract infection, thereby promoting the pore assay of the present invention as a biomarker to identify subjects at greatest risk for developing an asthma exacerbation.

Additionally, activation of $P2X_7$ receptors leads to mast cell up-regulation of IL-13 production. Moreover, in the presence of Toll Like Receptor co-stimulation, $P2X_7$-dependent signaling events trigger monocyte and macrophage production of Th1 inflammatory mediators including tumor necrosis factor-α (TNF-α), interleukin-1β (IL-1β), IL-18, and nitric oxide. Through this mechanism in combination with a phospholipase D-dependent phagolysosomal maturation pathway, human and murine data implicate $P2X_7$ as common a response pathway needed for host cell clearance of intracellular pathogens, specifically the BCG and clinical strains of *Mycobacteria tuberculosis* as well as two species of *Chlamydia*. Finally, the loss-of-function $P2RX_7$ genotype 1513 CC has recently been shown to confer increase risk of premature death after bone marrow transplantation with an elevated rate of associated bacteremia. In this way, P2RX$_7$ genetic variability may contribute to both the asthma phenotype as well as subject-specific differences in the strength of innate immune responses to airway pathogens.

The inventors have previously described a rapid, high-throughput, genomically-validated, functional screening assay in whole blood that has the precision to be used as an epidemiological tool. The protein encoded by P2RX7 assembles and functions as a homotrimeric, ligand-gated cation channel with a selectivity filter that can reversibly dilate to a size restriction of approximately 900 Da., a phenomenon referred to as known as "pore activity". The uptake of fluorescent dyes serves as a measure of pore function that varies by over two logs in healthy subjects. In this regard, pore function can be treated as a continuous variable to enhance sample size power calculations. Therefore, P2X$_7$ pore function correlates with the neutrophilic airway response to an upper respiratory tract infection and can modify the subsequent risk of loss of asthma control.

The following Examples are offered by way of illustration and not by way of limitation. Indeed, various modifications of the invention in addition to those shown and described herein will become apparent to those skilled in the art from the foregoing description and the following examples and fall within the scope of the appended claims.

III. EXAMPLES

Example 1

Rapid Measurement of Monocyte P2X$_7$ Pore Activity

This example sets forth a preferred method for the rapid measurement of monocyte P2X$_7$ pore activity by flow cytometry of washed whole blood.

Aliquots of citrated whole blood (500 μL/aliquot) were washed twice in HEPES-buffered saline (HBS; 130 mM NaCl, 5 mM KCl, 20 mM HEPES pH 7.4, 0.1% bovine serum albumin, 10 mM glucose; components purchased at Sigma, St. Louis, Mo.) and then labeled at room temperature with 125 ng of an anti-human CD14 antibody conjugated to phycoerythrin (BD Biosciences, San Diego, Calif.). After twenty minutes, the cells were washed twice in a potassium glutamate buffer (130 mM potassium glutamate, 5 mM KCl, 20 mM HEPES pH 7.4, 0.1% bovine serum albumin, 10 mM glucose; components from Sigma) to maximize the differences between high and low pore activities (18). In the absence of NaCl, cells were stimulated for twenty minutes with 0 or 250 μM 2'-3'-O-(4-Benzoylbenzoyl)adenosine 5'-triphosphate (Bz-ATP; Sigma) in the presence of 1 μM YO-PRO-1 (Molecular Probes, Eugene, Oreg.). Samples were then adjusted to 10 mM magnesium chloride, washed in HEPES-buffered saline and diluted to a volume of 2.5 mL in HBS.

Flow cytometry was performed on a flow cytometer (Becton Dickinson, San Jose, Calif., under the trade name FAC-Sca) that is calibrated daily using standard fluorimetric beads. The instrument settings were derived prior to enrolling study subjects using purified blood monocytes that had been separated from the red cells with Ficoll-Hypaque (Sigma), and stained with a phycoerythrin-conjugated anti-CD14 antibody in the presence and absence of YO-PRO-1. The phycoerythrin signal was collected with a 585 nm filter with a 42 nm band pass, whereas the YO-PRO-1 signal was collected with a 530 nm filter and a 30 nm band pass. Using the results from the purified monocytes, the instrument was then set to trigger on the phycoerythrin signal by setting the threshold above the background associated from unlabeled cells. Thus, data from all non-phycoerythrin labeled cells were not acquired. Because the YO-PRO-1 signal is so intense, channel compensation (approximately 30%) was used to eliminate the YO-PRO-1 signal in the phycoerythrin channel.

For each experiment with washed whole blood from the study subjects, the standard instrument settings were called up from a stored file and used without adjustment. Ten thousand phycoerthrin-labeled events were acquired using CellQuest and CellQuestPro acquisition and analysis software (v. 3.3 and 4.0; Becton Dickinson) and the amount of YO-PRO-1 taken up by these cells was measured in the presence or absence of prior stimulation with the P2X$_7$ agonist, Bz-ATP. Data analysis was done as a batch using FlowJo software (v. 4.3; Tree Star, Inc., Palo Alto, Calif.) in order to apply the same CD14+ gates to the entire study. The fold stimulation of P2X$_7$ pore activity was calculated using the ratio of the geometric mean of YO-PRO-1 fluorescence associated with the Bz-ATP-treated sample relative to that derived from the control.

Previous methods used to study the P2X$_7$ pore activity in primary cells include the lysis of erythrocytes, the isolation of whole blood leukocytes by gradient centrifugation or the purification of lymph node T cells (19,27). Because the inventors were interested in identifying individuals with novel P2X$_7$ genetic polymorphisms, they developed an assay that is more amenable to larger screens, potentially with greater sensitivity for detecting alleles with subtle influence on leukocyte P2X$_7$ pore activity. As shown in FIGS. 1A and 1B, the ability to detect specific populations of leukocytes according to their size and granularity was lost in the context of whole blood due to noise created by an overwhelming number of erythrocytes and platelets. However, labeling these cells with a CD14 specific antibody allowed for the use of a threshold technique to rapidly identify monocytes in whole blood samples (FIGS. 1C and 1D).

Figure 2:
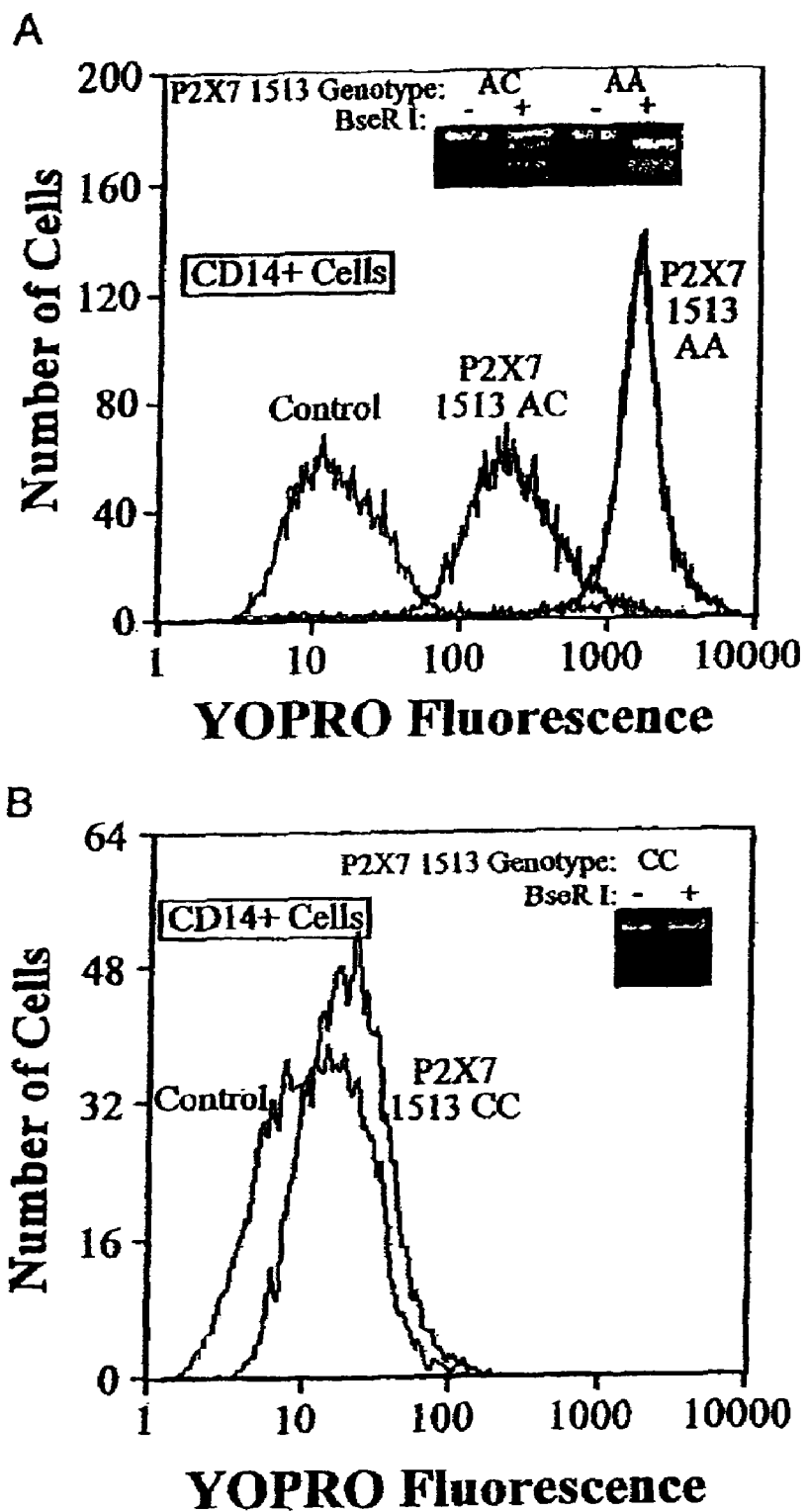
FIGS. 2A and 2B displays representative pore assay data from three subjects with different P2X$_7$ A1513C genotypes. Histogram representations are shown separated horizontally according to the amount of YO-PRO-1 taken up by CD14+ cells stimulated with 250 µM Bz-ATP or the saline control.
Figure 3:
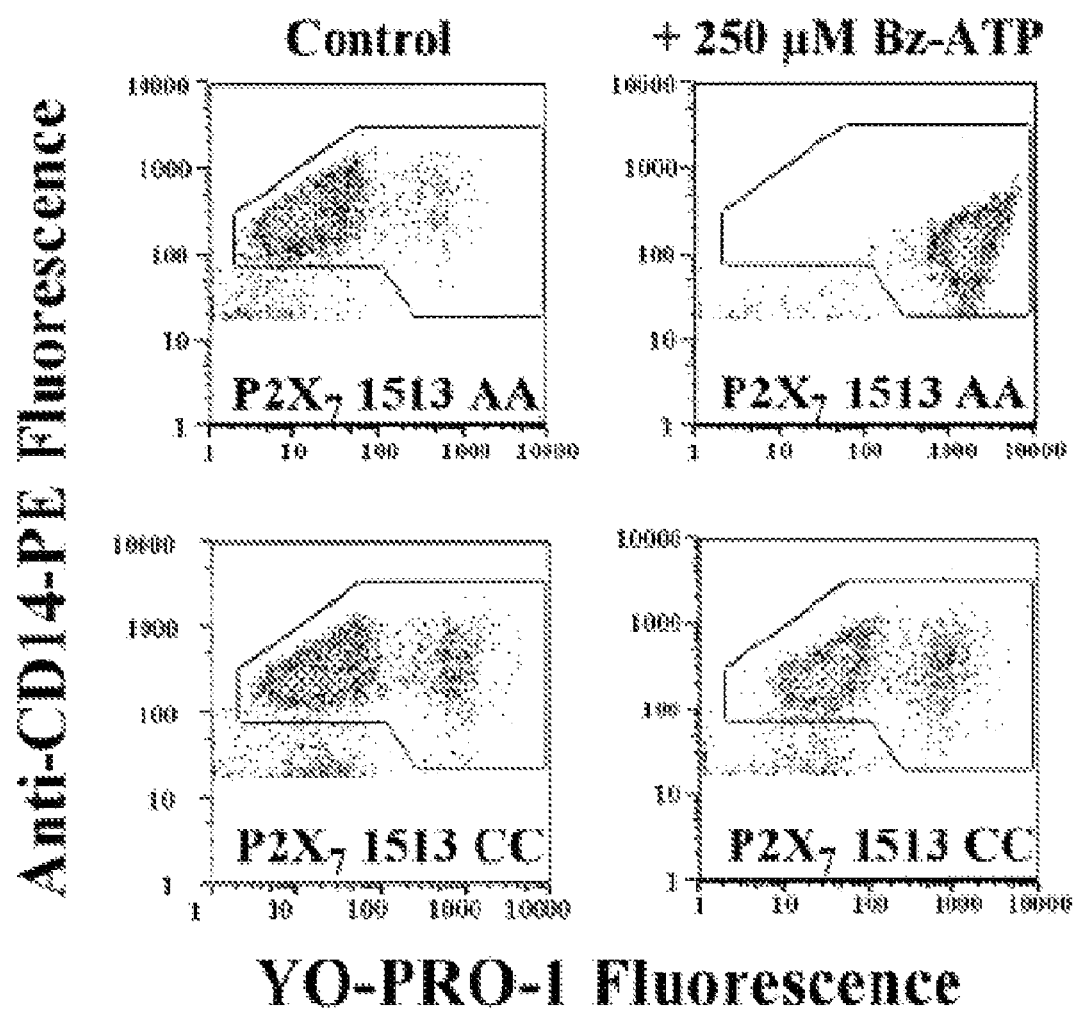
FIG. 3 depicts monocyte P2X$_7$ pore activity as measured by Bz-ATP-stimulated uptake of YO-PRO-1 in whole blood. Anti-CD14 antibody-labeled whole blood is treated with zero or 250 µM Bz-ATP for 20 minutes in the absence of sodium chloride at room temperature, followed by pore closure with 10 mM MgCl$_2$. Uniform flow cytometer settings and gates were used throughout the study. Data from CD14-negative cells are not acquired, allowing for the collection of 10,000 CD14$^+$ events. The figure shows data from one subject each with the P2X$_7$ 1513 common AA and variant CC genotypes.

By choosing conditions that amplify pore activity, this whole blood assay produced large differences between the monocyte pore activity in samples from individuals with the P2X$_7$ 1513 CC genotype relative to those from subjects with the AC or AA genotypes (FIG. 2). Specifically, treatment of washed whole blood for twenty min with the potent P2X$_7$ agonist Bz-ATP in an isotonic buffer solution lacking sodium chloride allowed for the passage of the fluorescent dye YO-PRO-1 (FIG. 2). This assay produced a stable phenotype in that the range of day-to-day variability from forty-one subjects averaged at 31±22% of the individual subject's mean.

Further referring to the data shown in FIG. 2, genomic DNA was prepared from frozen whole blood samples using the Puregene DNA Isolation kit (Gentra Systems, Minneapolis, Minn.). Genotypes were determined by PCR-based restriction fragment length polymorphism analysis and sequencing, as described in the following Example 2. In the inset panels, products from the polymerase chain reaction using P2X$_7$-specific primers and genomic DNA were treated with and without the restriction endonuclease BseR I and then separated by agarose gel electrophoresis and visualized by staining with ethidium bromide using standard techniques known in the art. The main panels illustrates data provided by the present invention and show Bz-ATP-induced uptake of the fluorescent dye YOPRO by cells in whole blood stained with an antibody to the cell surface maker CD14, as detected by flow cytometry. Control CD14 labeled cells in the absence of P2X$_7$ agonist display a dye uptake shifted left on the x-axis (i.e., lower dye intensity indicated less dye uptake thus lower P2X$_7$ pore activity in the assayed cells). The C/C, A/C and A/A genotypes can be easily distinguished from each other. Note that in FIG. 2A, the A/C genotype having a dye uptake intermediate between control cells and A/A cells treated with agonist. Thus, the assay described and claimed herein has the capacity to distinguish between P2X$_7$ genotypes, namely, 1513 C/C homozygous individuals, 1513 A/C heterozygous individuals and 1513 A/A homozygous individuals.

Studies described in this example relating to humans were performed in accordance with the principles of the Declaration of Helsinki, and was prospectively approved by the University of Wisconsin Institutional Review Board. Furthermore, all participating subjects verified their informed consent in writing.

Example 2

Detection of Human P2X$_7$ Nucleotide Receptor Polymorphisms

This example describes how the detection of human P2X$_7$ nucleotide receptor polymorphisms by a pore assay according to the invention is predictive of alterations in LPS-induced cytokine production.

As described in previous sections, the nucleotide receptor P2X$_7$ is expressed by most classes of leukocytes and initiates signaling events that act as an amplification loop for numerous LPS responses. The inventors tested the hypothesis that loss-of-function polymorphisms in the human P2X$_7$ gene predispose to the production of an anti-inflammatory mediator balance. Accordingly, the inventors developed a novel P2X$_7$ pore assay in whole blood that magnifies the activity from wild type alleles and preserves the gene dosage effect for the 1513 C polymorphism (AA, 69±4; AC, 42±4; and CC, 6±1-fold stimulation). Thirty of two hundred healthy individuals were identified as having low P2X$_7$ pore activity. Because platelets are a large source of extracellular ATP during inflammation, whole blood was treated ex vivo with *Salmonella typhimurium* LPS in the absence of exogenous nucleotides. Individuals from the low pore activity group generated reduced plasma levels of tumor necrosis factor-α ($p=0.029$) and higher amounts of interleukin-10 ($p=7\times10^{-5}$). The ability of P2X$_7$ polymorphisms to regulate the LPS-induced TNF-α to IL-10 ratio suggests that 15% of healthy adults may exhibit anti-inflammatory mediator responses during major infectious perturbations of the immune system, which can be predicted by P2X$_7$ pore activity.

Materials and Methods

Human subject participation. Investigations were carried out with approval of the University of Wisconsin Institutional Review Board, and written informed consent was obtained from all the participants. Two hundred healthy (paid) volunteers between the ages of 18 and 50 were enrolled for the first phase of the study on thirty-five days over the course of a year with one to nine subjects enrolled per study-day. None had been hospitalized in the last year or used medicines on a daily basis. Ten mL of whole blood were obtained by routine phlebotomy from each participant, assigned an anonymized code number, and anticoagulated with EDTA or citrate respectively for genetic and flow cytometric experiments.

Forty of these initial two hundred subjects were recruited for a second, cytokine phase of the study. In this phase, all seven subjects with the P2X$_7$ 1513 CC genotype and low monocyte pore activity were enrolled, together with fourteen randomly selected subjects from both the 1513 AA and AC groups (7 per group) with high (i.e. normal) pore activity. As discussed below in the Results section, twenty-three phase I subjects exhibited low pore activity despite P2X$_7$ 1513 common AA or heterozygote AC genotypes. Of this latter group, nineteen subjects were enrolled with four lost to follow up. Enrollment for the forty subjects in the second phase was done on seven different days with three to seven subjects per day, and the investigators were blind to the scheduling details of any individual subject. Fifteen mL of whole blood were obtained from each participant at the return visit in either EDTA or citrate tubes for genetic, flow cytometric, and cytokine experiments. A second anonymized code was assigned to these samples such that the investigators performing the cytokine experiments were blind to the genetic and flow cytometry results.

Determination of the P2X$_7$ A1513C and T1729A genotypes. Genomic DNA was prepared from frozen whole blood samples using the Puregene DNA Isolation kit (Gentra Systems, Minneapolis, Minn.). Polymerase chain reaction (PCR) primers for exon 13 of the human P2X$_7$ gene were identical to those described by Gu et al (19) (which amplifies a 356 bp product sufficient to incorporate both the 1513 and 1729 loci), and were synthesized by Integrated DNA Technologies (Coralville, Iowa). The final concentration of magnesium chloride was 1.5 mM and the annealing temperature was 58° C. The PCR product was digested with two units of the restriction endonuclease BseR I overnight at 37° C. The fragments were separated by gel electrophoresis in 1.5% agarose and observed by ethidium bromide staining. The P2X$_7$ 1513 C allele disrupts the BseR I palindromic sequence, thus the corresponding PCR fragment is not digested producing three bands for the 1513 AC genotype (356, 256, and 100 bp) and one band for the CC individuals (356 bp). Because the latter result cannot be discerned from the uncut fragment, PCR products from subjects with the 1513 CC genotype were sequenced bi-directionally (UW Biotech Center). Additionally, the PCR product from P2X$_7$ exon 13 was sequenced for all subjects enrolled in the cytokine phase of the protocol to determine the T1729A genotype.

Monocyte P2X$_7$ pore activity measured by flow cytometry of washed whole blood. Monocytes were selected as the cell population to screen because of the greater variability in pore function noted between individuals participating in a small study with forty-five healthy subjects (19). Aliquots of citrated whole blood (500 µL/aliquot) were washed twice in HEPES-buffered saline (HBS; 130 mM NaCl, 5 mM KCl, 20 mM HEPES pH 7.4, 0.1% bovine serum albumin, 10 mM glucose; components purchased at Sigma, St. Louis, Mo.) and labeled at room temperature with 125 ng of an anti-human CD14 antibody conjugated to phycoerythrin (BD Biosciences, San Diego, Calif.). After twenty minutes, the cells were washed twice in a potassium glutamate buffer (130 mM potassium glutamate, 5 mM KCl, 20 mM HEPES pH 7.4, 0.1% bovine serum albumin, 10 mM glucose; components from Sigma) to maximize the differences between high and low pore activities (18). In the absence of NaCl, cells were stimulated for twenty minutes with 0 or 250 µM 2'-3'-O-(4-Benzoylbenzoyl)adenosine 5'-triphosphate (Bz-ATP; Sigma) in the presence of 1 µM YO-PRO-1 (Molecular Probes, Eugene, Oreg.). Samples were then adjusted to 10 mM magnesium chloride, washed in HEPES-buffered saline and diluted to a volume of 2.5 mL in HBS.

Flow cytometry was performed on a FACScan flow cytometer (Becton Dickinson, San Jose, Calif.) calibrated daily using standard fluorimetric beads in conjunction with the CellQuest and CellQuestPro acquisition and analysis software (v. 3.3 and 4.0; Becton Dickinson). Instrument settings (forward scatter, E00 mV; side scatter, 458 mV; FL-1, 410 mV; FL-2, 412 mV; acquisition threshold for FL-2, 324 mV;

compensation, FL-2-32.6% FL-1) were derived prior to enrolling study subjects using purified blood monocytes that had been separated from the red cells with Ficoll-Hypaque (Sigma), and stained with a phycoerythin-conjugated anti-CD14 antibody in the presence and absence of YO-PRO-1. The phycoerythrin signal is collected with a 585 nm filter with a 42 nm band pass (FL-2), whereas the YO-PRO-1 signal is collected with a 530 nm filter and a 30 nm band pass (FL-1). Using the results from the purified monocytes, the instrument is then set to trigger on the phycoerythrin signal by adjusting the acquisition threshold above the background associated from unlabeled cells. Thus, data from all non-phycoerythrin labeled cells are not acquired, and pilot experiments with the isotype control antibody documented that this threshold was specific for $CD14^+$ cells with forward and side scatter characteristics consistent with monocytes (unpublished data). Because the YO-PRO-1 signal is so intense, compensation was used to eliminate the YO-PRO-1 signal in the phycoerythrin channel. These standard settings were then used without adjustment for the remainder of the investigation. Whereas this enhances reproducibility of the inventors' study, it also contributes to day-to-day assay variability. The inventors therefore chose the Bz-ATP-induced fold-stimulation of YO-PRO-1 uptake as a measurement of $P2X_7$ pore activity in attempt to account for these systematic factors, as well as minimize the potential variability from $P2X_7$-independent sources of YO-PRO-1 uptake such as pinocytosis.

Quantification of plasma cytokine levels after ex vivo stimulation of whole blood with lipopolysaccharide. Aliquots of citrated whole blood (1 mL/aliquot) were stimulated with Hank's standard phosphate buffered saline (PBS) without calcium or magnesium in the presence and absence of *Salmonella typhimurium* lipopolysaccharide (LPS; 0.1 μg/mL; ATCC strain 14028, List Biologicals Inc., www.listlabs.com) for 6 hr at 37° C. with 5% $CO_2$. Plasma samples were collected after centrifugation, aliquoted, and stored at −80° C. Sandwich ELISA quantification of TNF-α, IL-1β, and IL-10 levels in diluted plasma was done with the OptEIA reagents for 20 plates (BD Biosciences) according to standard methods. Data from a custom Search Light cytokine array (Pierce Biotechnology, Rockford, Ill.) and the ArrayVision analysis software (v. 8.0, Imaging Research Inc., St. Catharines, Ontario, Canada) for these cytokines were also compared. Standard curves were generated with the provided recombinant cytokines mixed with assay diluent and an identical dilution of unstimulated citrated plasma. Each plate contained one or more sets of plasma samples with known cytokine concentrations. All subject samples were run in duplicate on the same plate.

Statistical analysis. A Chi-squared goodness of fit test (28) was used to determine whether the 1513 C allele frequency was in accordance with the principles of the Hardy Weinberg equilibrium (29). For flow cytometric experiments, data analysis was done as a batch using FlowJo software (v. 4.3; Tree Star, Inc., Palo Alto, Calif.) in order to apply the same $CD14^+$ analysis gates to the entire study. Monocytes take up fluorescent dyes by macropinocytotic mechanisms (evidenced by comparing the fluorescence associated with unstimulated monocytes in the presence and absence of YO-PRO-1, data not shown), and this process likely has variability within a large sample independent from $P2X_7$ (30). Thus, to make the measurements of dye uptake more reflective of $P2X_7$ pore activity, a "X"-fold stimulation was calculated using the ratio of the geometric mean of YO-PRO-1 fluorescence from 10,000 $CD14^+$ cells treated with Bz-ATP relative to the geometric mean fluorescence derived from 10,000 $CD14^+$ cells treated with the vehicle control.

The ratios of these means were entered in to one-way analysis of variance with three classes as determined by the A1513C genotype, followed by unpaired Student's t-tests with correction for unequal variance. In order to determine the lowest-fold stimulation of monocyte pore activity statistically different from the $P2X_7$ 1513 CC group, the standard deviation of pore activity in this group was multiplied by 2.41 (the t-statistic for six degrees of freedom), and this product was added to the group mean. By this method, high $P2X_7$ pore activity was defined as greater than 15-fold Bz-ATP-induced YO-PRO-1 uptake by $CD14^+$ cells, and low activity was established as less than or equal to 15-fold. Thus, any new subject with greater that 15-fold Bz-ATP-induced pore activity has a 95% chance of being statistically different than the group of subjects with the 1513 CC genotype.

For the cytokine portion of the study, subject assignment to the low or high pore activity group was verified by replication of the phase I monocyte pore assay on the day of phase II re-enrollment. Although one individual in the high pore group and three subjects with low activity crossed over the assignment threshold defined above, the cytokine data were analyzed by the intention to treat method such that the initial group designations from phase I were applied for all of the data. Regarding the cytokine comparisons between groups, unpaired Student's t-tests were again used with correction for unequal variance. All calculations were performed using Excel:Mac 2001, v. SR1 (Microsoft Corporation, Redmond, Wash.) with a p-value of 0.05 adopted as the threshold for significance.

Results

Figure 4:
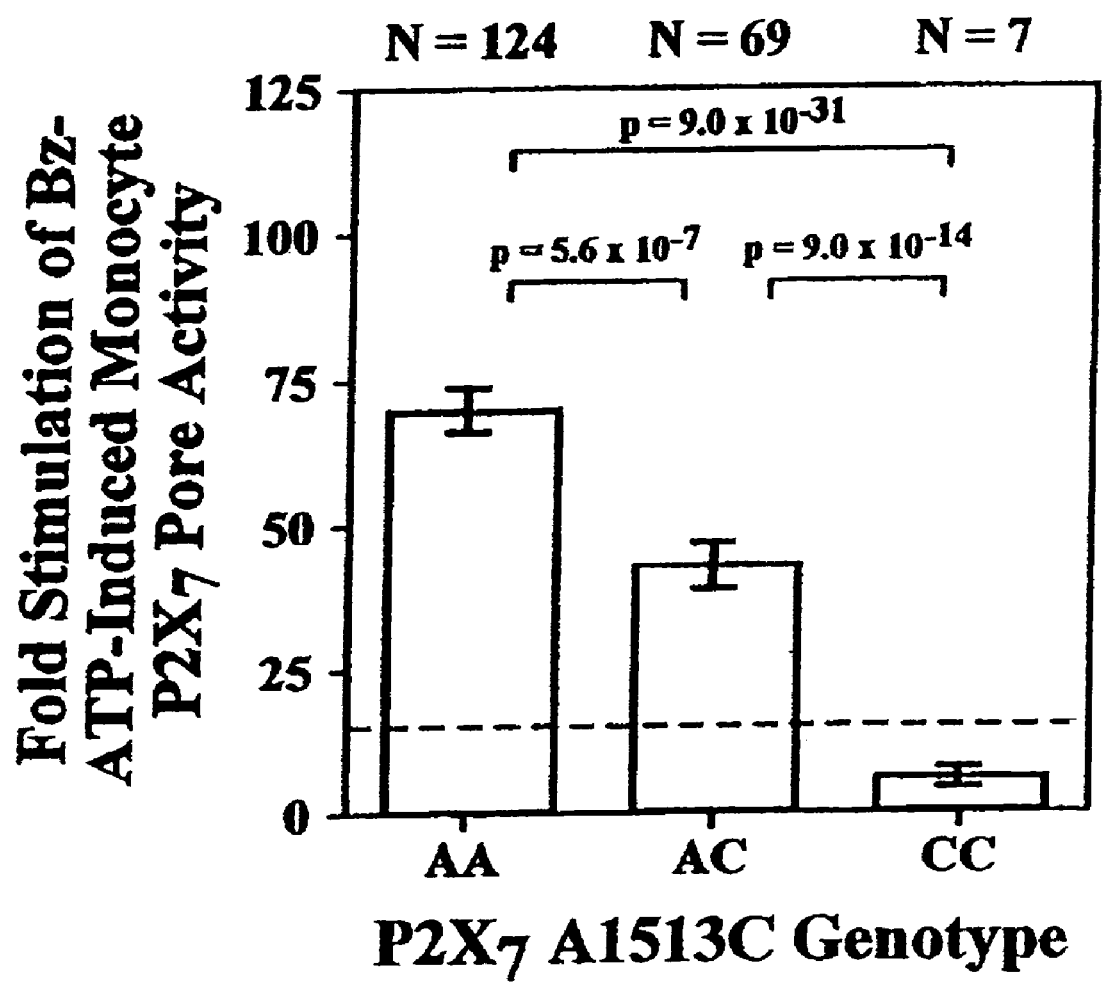
FIG. 4 illustrates P2X$_7$ pore activity in 200 healthy subjects separated according to the 1513 genotype. The ratios of Bz-ATP vs. control-stimulated YO-PRO-1 uptake in CD14$^+$ monocytes were calculated for 200 subjects on the day of Phase I enrollment as a selective measure of P2X$_7$ activity (see related Methods section). Data are separated according to the P2X$_7$ A1513C genotype, because this allele exhibits a predictable gene dosage effect when pore activity is measured by other methods (19). The group means and standard errors are shown along with the results of unpaired Student's t-tests with correction for unequal variance. The horizontal line depicts the statistically-defined separation between the high and low pore activity groups (see related Methods section).

Monocyte pore activity as a screen for individuals with $P2X_7$ genetic polymorphisms. In order to test the influence of various $P2X_7$ alleles on immune function, the inventors established a rapid screening assay sensitive to the presence of known polymorphisms. Although $P2X_7$ is expressed in most leukocytes, monocytes exhibit the greatest variability in pore activity (19). Previous methods used to study the $P2X_7$ pore activity in primary cells include the lysis of erythrocytes, the isolation of whole blood leukocytes by gradient centrifugation, or the purification of lymph node T cells (19,27). These techniques are too laborious for large phenotypic screens, and are confounded by the premature release of endogenous nucleotides as well as the potential for Percoll gradient-induced activation of monocytes by physical factors and/or contaminating LPS. By contrast, the labeling of whole blood with a CD14 specific antibody allowed for the use of a flow cytometry acquisition threshold technique to rapidly identify monocytes in these samples (FIG. 4), and dramatically reduced the potential for systematic variability associated with these isolation procedures. In order to maximize the differences in pore activity between the groups of subjects, the inventors implemented a long treatment time (20 min) at ambient temperature with a medium dose of a selective $P2X_7$ agonist (250 μM Bz-ATP) in the absence of sodium chloride, followed by pore closure at the end of the assay upon adjustment to 10 mM $MgCl_2$ before washing (18). These conditions selectively allowed for robust monocyte uptake of the fluorescent dye YO-PRO-1 in samples from 1513 AA subjects, with little to no $P2X_7$-stimulated activity associated with the CC genotype (FIG. 4).

For all subjects, the inventors measured the baseline fluorescence of CD14+ cells in whole blood samples mixed with YO-PRO-1, and compared them to readings obtained after stimulation with 250 μM Bz-ATP. The basal YO-PRO-1 fluorescence associated with untreated CD14+ cells in whole blood had a coefficient of variance of 0.40 over the course of the study, approximately half of which was due to day-to-day assay variability. The inventors chose the Bz-ATP-induced fold stimulation of YO-PRO-1 uptake as a measurement of $P2X_7$ pore activity in attempt to account for these systematic factors, as well as minimize the potential variability from $P2X_7$-independent sources of YO-PRO-1 uptake such as pinocytosis.

With this rapid whole blood assay, the inventors screened two hundred healthy adults and correlated the results with the $P2X_7$ A1513C genotype, because gene dosage is known to predict pore activity measured by other methods (19). Sixty-nine AC heterozygous and seven CC homozygous individuals were identified, yielding a $P2X_7$ 1513 C allele frequency of 0.21 with a distribution in accordance with the Hardy-Weinberg equilibrium ($\chi^2$=0.7, p>0.5) (29). Despite conditions that favor the identification of low responders, the rapid pore assay produced average "X"-fold stimulations of monocyte pore activity that were statistically distinct for each group according to the $P2X_7$ 1513 genotype (FIG. 4). Notably, all samples taken from subjects with the variant CC genotype had relatively low inducible $P2X_7$-pore activity (FIG. 4). An analysis of variance demonstrated that there was significantly more pore assay variability between the genotypes compared to the variances within each group (F=19.4, p=1×10$^{-8}$). The three t-test comparisons between the groups were significantly different (FIG. 4). Thus, the washed whole blood monocyte pore assay correctly identified all individuals with the $P2X_7$ 1513 CC genotype, and preserved the gene dosage effect previously described for the C allele (19).

Frequency of depressed monocyte pore activity in a healthy adult population, identification of individuals with other $P2X_7$ polymorphisms and performance of the whole blood pore assay. Given the results of the $P2X_7$ 1513 CC group, the inventors defined low monocyte pore activity statistically as less than or equal to fifteen-fold induction of Bz-ATP stimulated uptake of YO-PRO-1 (see the Statistical analysis section of the Methods). Using this threshold, twenty-three additional subjects had low pore activity despite their 1513 AA (n=11) or AC (n=12) genotypes, after confirmation of the latter results by sequence analysis of the PCR products from $P2X_7$ exon 13. This exon also contains a recently described single nucleotide polymorphism (T1729A) that confers an amino acid substitution (I568N) influencing the cell surface localization of the receptor (31).

Hence, eleven individuals in the low pore activity group were identified with the $P2X_7$ 1729 TA (but none with 1729 AA) genotype, nine of which were enrolled in the cytokine portion of the inventors' study (see below as well as Table 1). This was in keeping with its previously observed low allele frequency (0.02, (31)).

TABLE 1

| $P2X_7$ Pore Activity | $P2X_7$ A1513C genotype | $P2X_7$ T1729A genotype | # of subjects |
| --- | --- | --- | --- |
| high | AA | TT | 7 |
| high | AC | TT | 7 |
| low | AA | TT | 4 |
| low | AA | TA | 5 |
| low | AC | TT | 6 |
| low | AC | TA | 4 |
| low | CC | TT | 7 |

Referring to Table 1, $P2X_7$ genotype distribution for subjects enrolled in the LPS-induced cytokine study separated by pore activity are shown. Fourteen and twenty-six subjects were enrolled into Phase II of the study with high and low pore activity assignments and the genotypes were confirmed by sequence analysis of PCR products from exon 13. The latter group includes nineteen of the twenty-three Phase I subjects with low pore activity despite the presence of at least one 1513 A allele. The genotypes of the four subjects with low pore activity lost to follow up are AA/TT, AA/TA, AC/TT, and AC/TA; these four subjects are not included in the Table.

The 1513 C and the 1729 A $P2X_7$ polymorphisms segregated independently in the inventors' population; the 1729 A allele was equally present in individuals with the common 1513 AA and the heterozygote AC genotypes (n=6 and 5 respectively), and none of the 1513 CC subjects carried the 1729 A change. Interestingly, twelve individuals had low monocyte $P2X_7$ pore activity despite the presence of the common 1729 TT in conjunction with the absence of the variant 1513 CC genotypes. These data suggest the presence of yet to be disclosed-$P2X_7$ alleles and/or distinct genetic loci affecting nucleotide-stimulated monocyte pore activity.

Although the basal YO-PRO-1 fluorescence obviously affects the calculated Bz-ATP induced fold-stimulation of dye uptake, these values did not differ between the high and low pore activity groups (p=0.62). Evaluation of the distribution of baseline data and replacement of outlier baseline data (those greater than the mean±two standard deviations) with the group mean of unstimulated fluorescence showed that the calculation of fold-stimulation resulted in only one of two hundred subjects receiving an inappropriate pore activity group assignment. In sum, the whole blood pore assay accurately identified individuals with loss-of-function $P2X_7$ alleles.

Cytokine production by LPS-stimulated whole blood. The $P2X_7$ pore activity regulates the posttranslational activation of interleukin-1β via proteolytic cleavage (8, 32). Additionally, pharmacological studies have linked $P2X_7$ activity to the modulation of the levels of a variety of NF-κB-dependent inflammatory cytokines and mediators (5, 8, 10, 33). Hence, the inventors hypothesized that individuals with the 1513 CC genotype and/or low pore activity regardless of their $P2X_7$ genotype would produce less interleukin-1β or have an anti-inflammatory cytokine profile in response to lipopolysaccharide (LPS). To test this hypothesis, the inventors re-enrolled forty of the initial two hundred Phase I subjects; twenty-six from the low pore group and fourteen randomly selected controls with high activity and with equal representation of the 1513 AA and AC genotypes (Table 1). The pore assay group assignments from Phase I were reproducible for 36 of the 40 Phase II subjects staying below or above the 15-fold stimulation cut off and with collective intra-subject day-to-day coefficients of variance of 0.16 and 0.32 for the low and high groups respectively. Three subjects with low pore activity in Phase I had a 13, 45, and 57% increase in their Phase II pore assay results, whereas one subject with high Phase I pore activity had a 53% reduction on retesting such that the replicate result predicted the opposite group assignment in Phase II. In all cases, the Phase I group assignments were used for an intent-to-treat analysis of the cytokine data.

Figure 5:
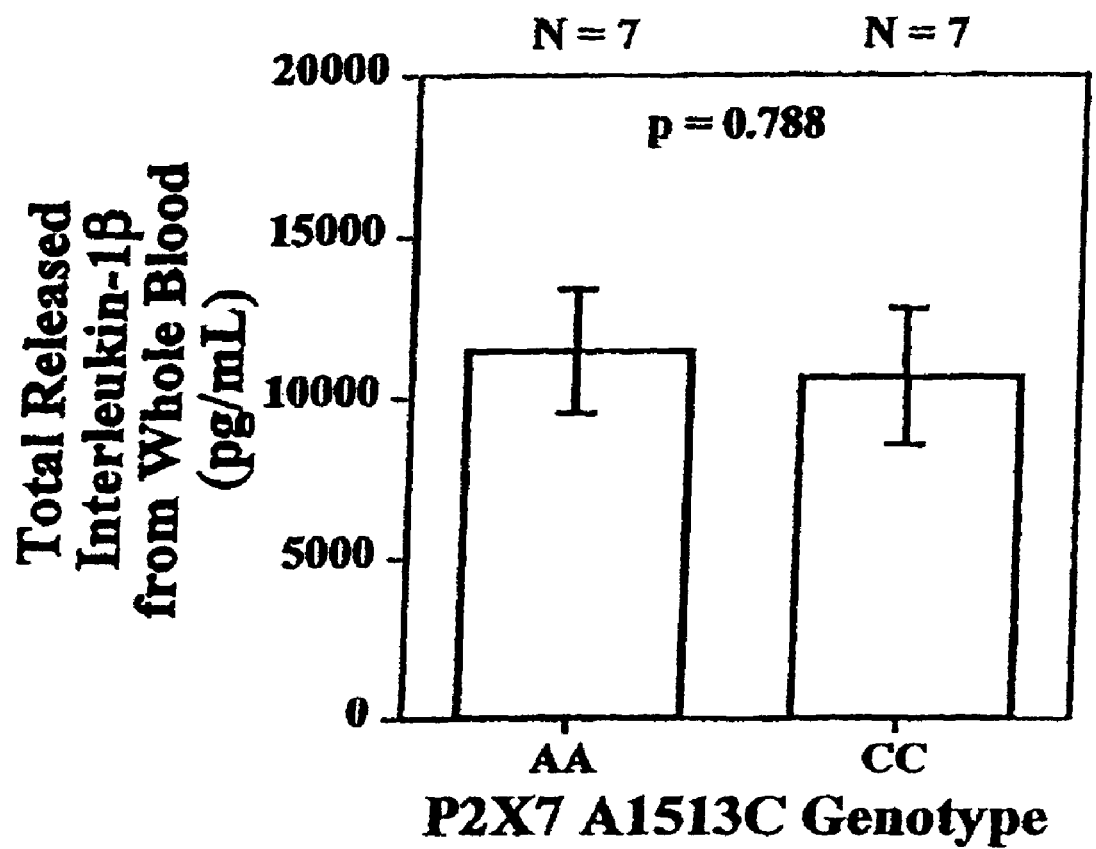
FIG. 5 depicts LPS-stimulated whole blood production of interleukin-1β. Whole blood samples from Phase II subjects were stimulated for 6 hr at 37° C. with 0 or 100 ng/mL of *Salmonella typhimurium* LPS followed by centrifugation to harvest plasma. The control samples contained undetectable levels of IL-1β. Subject samples were quantified by sandwich ELISA in duplicate, and the data shown are the group means and standard errors from seven subjects per group (P2X$_7$ 1513 AA/1729 TT vs. 1513 AA/1729 TT) combined from three experiments. Similar results were also seen using a cytokine array available from Pierce Biotechnology, Inc. under the trademark SEARCHLIGHT.

Whole blood samples were used to measure the cytokine responses in vitro after 6 hours of stimulation with zero or 100 ng/mL of *Salmonella typhimurium* LPS, as these conditions produce half-maximal responses in most donors (34-37). Additionally, LPS-stimulated platelets in whole blood are the source for abundant levels of endogenous adenine nucleotides (38) and the interaction between LPS-stimulated platelets and monocytes has been shown to augment the production of IL-1β (39). This method of LPS-stimulation of whole blood resulted in robust production of interleukin-1β plasma levels for all of the subjects regardless of genotype or $P2X_7$ pore activity, above an undetectable background in the saline-treated controls. There was no difference in the LPS-stimulated plasma IL-1β levels between subjects with the 1513 AA or CC genotype (FIG. 5). Combining data from the high and low pore activity subjects did not compress the variance sufficiently to reach statistical significance (9.9±1.4 and 8.4±0.7 ng/mL respectively, p=0.37).

However, because the plasma levels of tumor necrosis factor-α and interleukin-10 have been linked to the cytokine balance pertinent to a variety of inflammatory diseases (40-44), the inventors measured these two mediators as surrogates for the pro- vs. anti-inflammatory response profiles. Similar to the results with IL-1β, the saline-treated samples contained undetectable plasma levels of TNF-α and IL-10 for all but one of the subjects. By contrast, the samples from subjects with low $P2X_7$ monocyte pore activity had lower LPS-induced levels of TNF-α relative to the high pore activity group (FIG. 4). This coincided with higher levels of IL-10 in the low pore group (FIG. 6). When the TNF-α/IL-10 ratio was calculated on an individual subject basis, this measure for subjects with high pore activity was 264% greater on average than that of the low pore group (FIG. 6). Thus, the monocyte pore assay predicted the $P2X_7$ genotype, as well as the TNF-α/IL-10 ratio in response to whole blood treatment with LPS. With these mediators as surrogates, this suggests that individuals with low pore activity due to $P2X_7$ polymorphisms have an anti-inflammatory mediator profile in response to LPS.

The present investigation confirms the $P2X_7$ 1513 C allele frequency in a large sample, and extends these results to include individuals from North America. Previous studies have documented a 1513 C allele frequency of 0.09 in Gambians (45), 0.12 in Australians (19), and 0.14 in Swedes (46), in comparison to the inventors' findings of 0.21 in the Upper Midwest. The 1513 allele is more common than the $P2X_7$ 1729 polymorphism, with an estimated 1729 A allele frequency of 0.02 in Australians (31) and at least 0.03 in the inventors' sample. Coupled with the five other human $P2X_7$ promoter polymorphisms (47) and two murine structural variants, this genetic locus may be a region of greater variability than presently documented.

This is the largest study to date to evaluate the variability of $P2X_7$ function in monocytes. In particular, the inventors have developed a novel method for characterizing $P2X_7$ pore function with several distinct advantages. The antibody labeling and flow cytometric threshold techniques allow for the functional assessment of monocytes (or other cell types) using ≧1 mL of whole blood, an aspect that has tremendous significance regarding the potential for future use in an unstable, critically-ill patient population. With the existing method, results are available in less than three hours from the time of phlebotomy, making possible the design of immunomodulatory clinical trials with prospective stratification of patient subsets. Moreover, the technique is readily adaptable for use in a clinical lab of an average community hospital, broadening its applicability compared to previous methods.

In addition, the inventors demonstrated a subset of healthy subjects with discordance between their $P2X_7$ 1513 genotypes and monocyte pore activities. Twenty-three individuals in the inventors' sample had low pore activity despite the presence of at least one wild-type 1513 A allele (FIG. 4 and Table 1). Eleven of these twenty-three were 1729 TA heterozygotes, suggesting that at least twelve subjects in this study have yet to be disclosed polymorphisms affecting monocyte $P2X_7$ pore activity. In combination with the seven subjects with the 1513 CC genotype, these data demonstrate that 15% of individuals residing in the Upper Midwest of North America have low monocyte $P2X_7$-regulated pore function. With this frequency of reduced leukocyte activity among healthy individuals, it is unlikely that defects in the $P2X_7$ pore are associated with gross immunodeficiency, however, these alleles may contribute to the variability in the immune response when the system is under stress, such as during a major infection.

A potential trade off might be enhanced microbial clearance at the expense of a higher incidence of autoimmune disorders and visa versa. Most candidate genes for these types of questions have multiple alleles, each with variable influence on protein function, inconsistent allele frequencies among distinct substrata of a given population, and unequal associations with clinical disease. Thus, functional tests, like the rapid monocyte pore assay, that are able to account for the influence of multiple alleles in linked pathways and to screen for polymorphisms at novel loci, are needed to assess the biological relevance of genetic variation in the pathogenesis of a given disease process.

In sum, the inventors have developed a rapid, washed whole blood pore assay that has numerous advantages over previous methods for detecting $P2X_7$ allele variants influencing pore activity. The pore assay, in addition to providing a rapid and reliable assay of pore activity, facilitates rapid identification of subjects with novel $P2X_7$ mutations. Characterization of these mutations will lead to additional polymorphic markers useful in determining correlation between allelic variants and clinical outcomes. Such recognition of prognostic determinants is extremely valuable in refining immunomodulatory and anti-infectious therapy on a patient-by-patient basis.

The antibody labeling and flow cytometric threshold techniques allow for the functional assessment of monocytes (or other cell types) using ≧1 mL of whole blood, an aspect that has tremendous significance regarding the potential for future use in an unstable, critically-ill patient population. Moreover, the technique is readily adaptable for use in a clinical lab of an average community hospital, broadening its applicability compared to previous methods. Because the results are available in less than three hours from the time of phlebotomy, the design of immunomodulatory clinical trials with prospective stratification of patient subsets is now possible. An underlying hypothesis for these trials would be that septic patients with attenuated monocyte $P2X_7$ pore activity would be relatively protected from organ dysfunction and shock, potentially at the expense of a diminished ability to control the infection locally or at increased susceptibility to certain classes (e.g. intracellular) of microbial pathogens.

Example 3

Identification of SNPs in Human $P2X_7$

This example describes the identification of single nucleotide polymorphisms (SNPs) in human $P2X_7$ as facilitated by a functional assay according to the present invention. The frequency distribution of certain SNPs between low and high pore activity groups is supportive of the SNPs' utility as prognostic indicators of sepsis susceptibility.

As described in the previous example, two hundred healthy individuals were screened for $P2X_7$ phenotypes by a pore assay according to the invention. Based on the results, the population was classified into high and low pore activity groups. As discussed herein, persons with mutant $P2X_7$ genes resulting in low pore activity appear to have an elevated susceptibility to sepsis. Thus, a correlation of low pore activity with any given SNP is a marker for sepsis susceptibility. About 15% (30 people) of the two hundred healthy individuals displayed depressed pore activity. Of the thirty people, sixteen were identified as having previously known mutations; seven people had the A1513C mutation and nine people had the T1729 mutation, respectively. The remaining nineteen individuals with low pore activity did not correlate with any previously known mutations in the $P2X_7$ gene.

To characterize the molecular nature of these low pore activity cases, the inventors sequenced the $P2X_7$ gene from each of the relevant individuals to identify the presence of $P2X_7$ mutations. $P2X_7$ exons 1-13 were amplified by polymerase chain reaction (PCR) using exon-specific intronic primer pairs. Amplification reactions of individual exons 1-13 were generally-carried out under the following parameters: initial denaturation at 94° C. for 10 min followed by 35 cycles of denaturation at 94° C. for 1 min., annealing at 50-70° C. for 1 min., and extension at 72° C. for 10 min. Final reaction concentrations for exons 1-7 and 9-13 were: 1×PCR buffer II (supplied with enzyme), 1.5 mM $MgCl_2$, 200 uM each dNTPs, 0.4 uM Primer-Forward, 0.4 uM Primer-Reverse and 2.5 units/reaction Amplitaq Gold (Applied Biosystems). Final concentrations for reactions amplifying exon 8 were: 1×PCR buffer II (supplied with enzyme), 3.0 mM $MgCl_2$, 200 uM each dNTPs, 0.4 uM Primer-Forward, 0.4 uM Primer-Reverse and 2.5 units/reaction Amplitaq Gold (Applied Biosystems). Primers were generally 21-25mers designed by reference to human $P2X_7$ gene sequences which are publicly available (e.g., Accession nos. NM177427, NM002562, BC011913, Y12851, Y12852, Y12853, Y12854, Y12855, all sequences incorporated herein by reference).

Table 2 below illustrates SNPs identified by the present inventors during sequence analysis of $P2X_7$ genes of individuals from high pore and low pore activity groups, such groups being described in a previous example. Previously-known SNPs are indicated with a "+". SNPs identified in the present study which exhibit a frequency difference between individuals with high or low $P2X_7$ pore activity are indicated with an "*". The positions of SNPs in intronic sequences are indicated as either upstream of a bordering exon (position number is negative relative to exon's 5' end) or downstream of a bordering exon (position number is positive relative to exon's 3' end). Frequencies in low and high pore activity groups are indicated where they have been determined by the present inventors. Selected SNPs are further described in the following paragraph.

TABLE 2

| Exon | Base Change (position in cds or relative to exon)) | AA Change or relative intron position | Frequency among low pore activity individuals | Frequency among high pore activity individuals |
|---|---|---|---|---|
| 1 | G --> C (+42) | 3' intron | 18 WT (94.7%) 1 Het (5.3%) | |
| 4 | A --> G (-53) | 5' intron | 9 Het (47.4%) 10 Mut (52.6%) | |
| 5 | G474A | Gly150Arg | 16 WT (84.2%) 2 Het (10.5%) 1 Mut (5.3%) | 7 WT (87.5%) 1 Het (12.5%) |
| 5 | C489T | His155Tyr | 6 WT (31.6%) 10 Het (52.6%) 3 Mut (6.3%) | 2 WT (25%) 3 Het (37.5%) 3 Mut (37.5%) |
| 5 | C531T | Cys168Cys | 10 WT (52.6%) 9 Het (47.4%) | 8 WT (100%) |
| 5 | T --> C (-48) | 5' intron | 1 WT (5.3%) 12 Het (63.2%) 6 Mut (31.6%) | 8 Mut (100%) |
| 6 | A --> C (-107) | 5' intron | 9 Het (47.4%) 10 Mut (52.6%) | |
| 6 | C --> T (-42) | 5' intron | 9 Het (47.4%) 10 Mut (52.6%) | |
| 6 | C --> T (-38) | 5' intron | 9 Het (47.4%) 10 Mut (52.6%) | |
| 7 | Dup/Ins TTTG (-17) | 5' intron | 9 WT (47.4%) 10 Mut (52.6%) | |
| 7 | G --> C (-5) | 5' intron | 9 WT (47.4%) 10 Mut (52.6%) | |
| 8 | G835A | Arg270His | 14 WT (73.7%) 4 Het (21.1%) 1 Mut (5.3%) | 6 WT (75%) 1 Het (12.5) 1 Mut (12.5%) |
| 9 | G946A* | Arg307Gln | 16 WT (84.2%) 3 Het (15.8%) | 8 WT (100%) |
| 9 | GA --> AG (-2) | Glu-2Arg | 19 Mut (100%) | 8 Mut (100%) |
| 11 | A1068G* | Thr348Ala | 1 WT (5.3%) 0 Het (0%) 18 Mut (94.7%) | 3 Het (37.5%) 5 Mut (62.5%) |
| 11 | C1096G* | Thr357Ser | 10 WT (52.6%) 9 Het (47.4%) | 8 WT (100%) |
| 11 | C --> T (+34) | 3' intron | 1 WT (5.3%) 0 Het (0%) 18 Mut (94.7%) | |
| 12 | T1287C | Leu421Leu | 19 Mut (100%) | |
| 13 | T --> C (-85) | 5' intron | 1 WT (5.3%) 0 Het (0%) 18 Mut (94.7%) | 8 Het (38.1%), 13 Mut (61.9%) |
| 13 | G --> A (-84) | 5' intron | 15 WT (78.9%) 3 Het (15.8%) 1 Mut (5.3%) | 19 WT (90.5%) 2 Het (9.5%) |
| 13 | A1469C | Arg481Ser | 19 Mut (100%) | 21 Mut (100%) |
| 13 | A1772G | Pro582Pro | 1 WT (5.3%) 0 Het (0%) 18 Mut (94.7%) | 1 WT (4.8%) 7 Het (33.3%) 13 Mut (61.9%) |
| 13 | A1513C+ | Glu496Ala | 9 WT (47.4%) 10 Het (52.6%) | 9 WT (42.9%) 5 Het (23.8%) 7 Mut (33.3%) |
| 13 | A1405G* | Gln460Arg | 18 WT (94.7%) 1 Het (5.3%) | 16 WT (76.2%) 5 Het (23.8%) |
| 13 | G1628T | Leu534Leu | 9 WT (47.4%) 10 Het (52.6%) | 19 WT (90.5%) 2 Het (10.5%) |
| 13 | T1729A+ | Ile568Asn | 10 WT (52.6%) 9 Het (47.4%) | 21 WT (100%) |
| 13 | C1448T | Pro474Pro | 10 WT (52.6%) 9 Het (47.4%) | 20 WT (95.2%) 1 Het (4.8%) |

Several SNPs depicted in Table 2 above are further detailed below and are particularly useful as prognostic indicators, the use of such being described in a previous section.

Sequence analysis of PCR fragments corresponding to exon 9 revealed a previously-undescribed G to A transition at nucleotide position 946 resulting in an R307Q mutation in the $P2X_7$ amino acid sequence. This SNP was not present in eight high pore activity individuals sampled but was heterozygous in three of nineteen low pore activity individuals. Therefore, this SNP was present in low pore activity individuals sampled at a 15.8% frequency as compared to 0% frequency in high pore activity individuals.

A second, previously-undescribed SNP was located in exon 11 wherein an A to G transition at nucleotide position 1068 resulted in a T348A mutation in corresponding amino acid sequence. In eight high pore activity individuals sampled, this SNP was heterozygous in three individuals and homozygous in the remaining five. In nineteen low pore activity individuals, this SNP was absent in one individual, and homozygous in the remaining eighteen (94.7% frequency among low pore activity individuals).

A third SNP was identified in exon 11 wherein a C to G transversion at nucleotide position 1096 resulted in a T357S mutation in the corresponding polypeptide. In eight high pore activity individuals sampled, this SNP was not present. In contrast, of nineteen low pore activity individuals assayed, this SNP was heterozygous in nine individuals. Thus, the SNP was present at a 47.4% frequency sampled low pore activity individuals as compared to 0% of high pore activity individuals.

A fourth SNP was identified in exon 13 wherein an A to G transition at nucleotide position 1405 resulted in a Q460R mutation in the respective polypeptide. In twenty one high pore activity individuals sampled, the SNP was not present in sixteen of the individuals and heterozygous in five. In nineteen low pore activity individuals, the SNP was not present in eighteen individuals and heterozygous in the remaining individual. Therefore, the frequency of the SNP was different between groups with it being present in 23.8% of high pore activity individuals sampled but only 5.3% of low pore activity individuals sampled.

Example 4

Bead Standardization to Minimize Variability

This example describes a bead standardization approach to minimize variability in a functional genomic, flow cytometric assay being used in a multi-center clinical trial.

Flow cytometry analysis of $P2X_7$ receptor pore activity in human blood monocytes segregates variants from common $P2X_7$ receptor genotypes/phenotypes and may serve as a biomarker for infectious/inflammatory diseases and disorders. To facilitate association studies, the inventors provide herein a genomically validated functional assay capable of bridging disparate P2RX7 genetic, phenotypic and clinical results, minimizing intra-laboratory variability and increasing statistical power in the face of sample size constraints (10,14).

Because declining monocyte viability in aged samples influences assessment of $P2X_7$ pore function, the assay of the present invention excludes non-viable cells. Nonviable cells within the total monocyte population affect the measurement of true $P2X_7$ pore function due to unregulated YO-PRO-1 uptake associated with loss of plasma membrane integrity influencing the basal rate as well as attenuated responsiveness to BzATP stimulation. Closure of the $P2X_7$ pore by divalent cations (17) allows inclusion of a second vital dye in the assay to assess plasma membrane permeability.

In this regard, eliminating $PI_{pos}$ events facilitates accommodation of samples aged up to four days after phlebotomy. Therefore, exclusion of nonviable cells in the analysis of $P2X_7$ pore activity in monocytes is warranted for all future studies in order to measure true $P2X_7$ pore function. An additional feature of the present invention is that it facilitates comparisons between different types of cytometers. For instance, the bead adjusted set up method of the present invention produced median YO-PRO-1 fluorescence measurements in BzATP treated samples that differed by only 2.0±1.5 percent when processed simultaneously on FACScan and FACSCalibur cytometers. As a digital machine, the LSR II produced higher values than the analogue instruments but the results were visually comparable in terms of the decades relative to the scale for the individual machine. An assumption in establishing PMT targets by this method is that they fall within the dynamic range for the instrument used.

Although P2RX7 has not previously been referred to as an asthma gene, its chromosomal location is thought to contain numerous such candidates based on linkage in multiple populations to measurements of lung function (34-37). Additionally, P2RX7 is thought to control the immune response to infection with *Chlamydia* species (38,39), an intracellular pathogen thought to contribute to asthma pathogenesis which is also one of the therapeutic targets for the ACRN-MIA clinical trial (40). The presently described correction for sample age and the exclusion of nonviable cells will require refinement of the receiver/operator curve analysis using results obtained by our present method in order to accurately segregate variant from common $P2X_7$ receptor genotypes/phenotypes in future studies. In general, this approach of genomically validating results from the $P2X_7$ pore assay could serve as an additional control as other laboratories begin to adopt this method.

The present invention accordingly provides, in one embodiment, a standardized method for quantitative detection of $P2X_7$ pore function by monocytes in human whole blood examined within 4 days post-phlebotomy that will likely facilitate future cohort studies by minimizing intra- and inter-laboratory variation in sample acquisition. Because individuals with reduced capacity for $P2X_7$ pore formation are suggested to be predisposed to an anti-inflammatory cytokine profile in the setting of immune system perturbation (10), utilization of our novel standardized calibration method will facilitate the segregation of variant from common $P2X_7$ receptor genotypes/phenotypes and potentially identify variation in $P2X_7$ receptor pore function as a biomarker for infectious/inflammatory diseases and disorders.

Materials and Methods

Human Subject Participation and Sample Collection. Investigations were carried out with approval of the University of Wisconsin Institutional Review Board, and ancillary studies to two protocols (single center and multi-center) involving patients with asthma were performed after obtaining informed consent. For all experiments, five to ten mL of whole blood were obtained by routine phlebotomy, anticoagulated with citrate and stored at room temperature with or without overnight shipping until the time of processing. Eight participants were recruited for two additional phlebotomy visits within a three-month span. All samples were processed and analyzed at the Flow Cytometry Facility of the University of Wisconsin Paul P. Carbone Comprehensive Cancer Center.

PBMC Isolation. Six mLs of citrate-treated blood was underlayed with three mLs of Lymphoprep (Axis-Sheild, Oslo, Norway) and centrifuged at 800 g for 30 minutes at room temperature. The cellular interface was collected and washed twice with sterile phosphate-buffered saline (PBS). Cells were counted and assayed for pore activity as described below.

Sample Preparation. Although all leukocytes studied to date express $P2X_7$, monocytes were selected as the cell population to screen because of the greater sensitivity of pore function noted between individuals participating in a small study with forty-five healthy subjects (5, 34). Staining procedures were as previously described (10, 14, 34). Briefly, aliquots of citrated whole blood (500 L/aliquot) were washed twice in HEPES-buffered saline (HBS; 130 mM NaCl, 5 mM KCl, 20 mM HEPES pH 7.4, 0.1% bovine serum albumin, 10 mM glucose; components purchased at Sigma, St. Louis, Mo.) and resuspended in the original 500 L volume. A 10 µL aliquot of anti-human CD14 antibody conjugated to phycoerythrin (CD14-PE, 50 µg/mL; BD Biosciences, San Diego, Calif.) was added to each sample and incubated at room temperature for 20 min. The cells were washed twice in a potassium glutamate buffer (130 mM potassium glutamate, 5 mM KCl, 20 mM HEPES pH 7.4, 0.1% bovine serum albumin, 10 mM glucose; components from Sigma) to maximize the differences between high and low pore activities (17).

In the absence of NaCl, cells were stimulated for 20 min with 0 or 250 M2'-3'-O-(4-Benzoylbenzoyl)adenosine 5'-triphosphate (BzATP; Sigma) in the presence of 1 MYO-PRO-1 (Molecular Probes, Eugene, Oreg.). Samples were adjusted to 10 mM magnesium chloride, washed in HEPES-buffered saline and diluted to a volume of 2.5 mL in HBS. These latter steps have been previously shown to close the pore rapidly allowing for kinetic precision in a large clinical study (10, 34). For the methods described here, including all the samples from the MIA trial (Table 3), propidium iodide (PI; 5 μg/mL) was added to each sample and incubated for 15 min prior to sample acquisition using flow cytometry as described below.

Determination of Instrument Settings and Calculation of Spectral Overlap. All instruments in the facility are cleaned daily and assessed for laser alignment, photomultiplier tube (PMT) performance, linearity and noise. All fluorochromes were excited with a 488 nm laser and the following filter sets were used in all flow cytometers: a BP 530/30 for YO-PRO-1, a BP 585/42 for PE and a LP 670 for propidium iodide. Experiments were performed on FACScan, FACSCalibur, and LSR II flow cytometers (Becton Dickinson, San Jose, Calif.) in conjunction with the CellQuest, CellQuestPro, FACSDiva acquisition and analysis software programs (v. 3.3, v. 4.0, and v. 5.0.1, respectively; Becton Dickinson).

Figure 15:
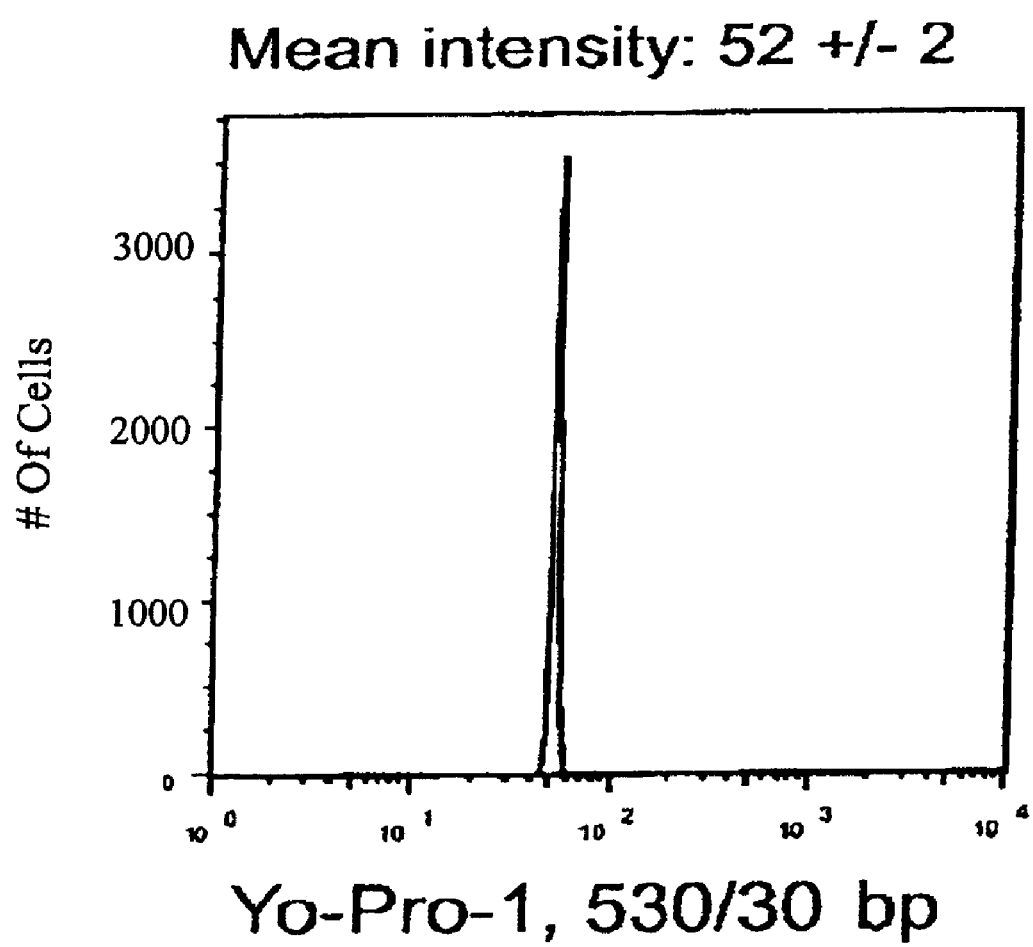
FIGS. 15A-15C are histograms of the fluorescence of Spherotech Rainbow Beads (mid-range) when set to the indicated target values in each of the PMTs used in the assay. These target values were used on the analog flow cytometers, FACScan, and FACSCalibur.
Figure 15:
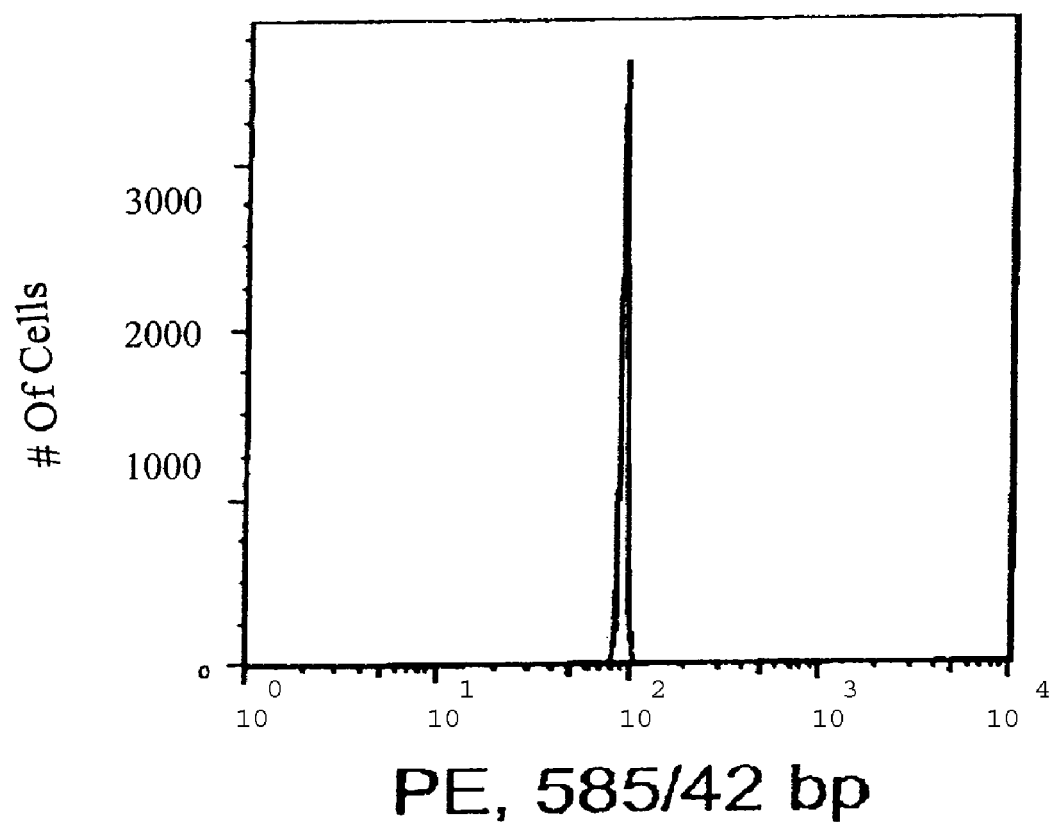
Figure 15:
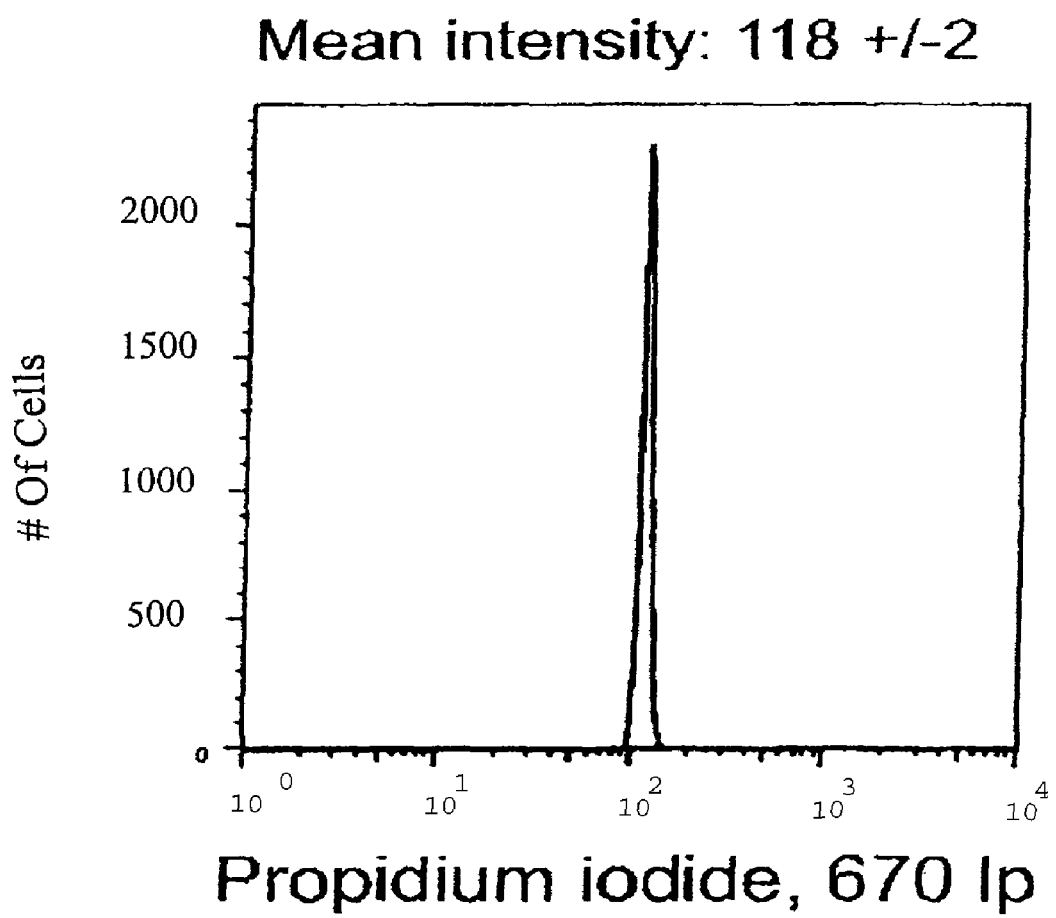

Previously, pore activity was measured on a FACScan flow cytometer (Becton Dickinson, San Jose, Calif.) using recalled instrument settings: YO-PRO-1 at 410 mV, PE at 412 mV, acquisition threshold for PE at 324 mV, and PE-32.6% YO-PRO-1 compensation (10). To facilitate comparisons across instrument platforms and among laboratories, we used these recalled settings as a template to adapt desired PMT voltages for SpheroTM Rainbow fluorescent particles (mid-range 3.0-3.4 μm; Sperotech, Lake Forest Ill.), corresponding data shown in FIG. 15. Rainbow particles have a very stable fluorescence and can be stored and used over a long period of time, allowing the intensities of these particles in each fluorescent detector to serve as target values for determining the voltages applied to each PMT for all of the cytometers used.

The same target values were used for the analog instruments, FACScan and FACSCalibur (BD Biosciences, San Jose, Calif.) because these instruments process fluorescence signals in the same way and the intensities determined were very close (data not shown). The LSR II (BD Biosciences, San Jose, Calif.) uses digital processing and fluorescence is collected and sampled differently so a second set of target values using these same samples was determined for each color detector on this cytometer. Specifically, the target value ranges of 558±20 (YO-PRO-1), 511±20 (PE) and 676±20 (PI) were used on the LSR II. To calculate spectral overlap, BD Calibrite™ fluorescent particles were used as a substitute for single stained control samples because detection of monocytes in the context of whole blood requires thresholding on a fluorescent tag (CD14-PE) making the former method impossible.

Figure 16:
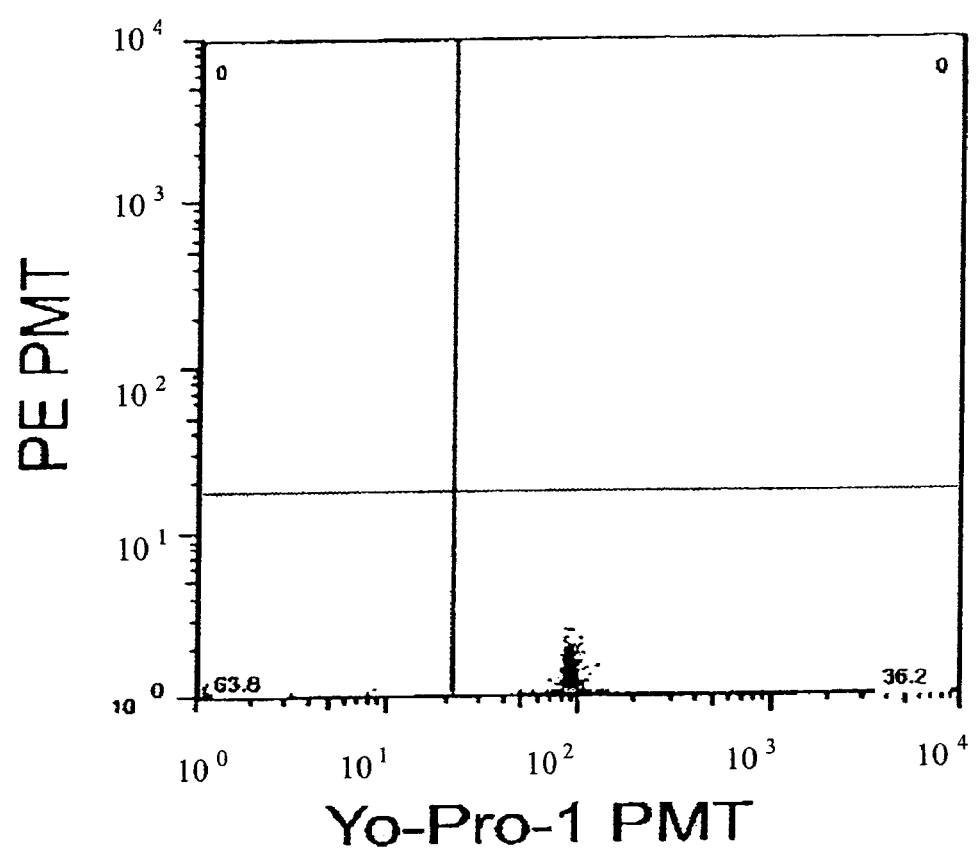
FIGS. 16A-16C are representative spectral overlap corrections performed using FITC or PE hard-dyed Calibrite Beads (Becton Dickinson) and the sensitivities determined for each PMT as illustrated in FIG. 7.
Figure 16:
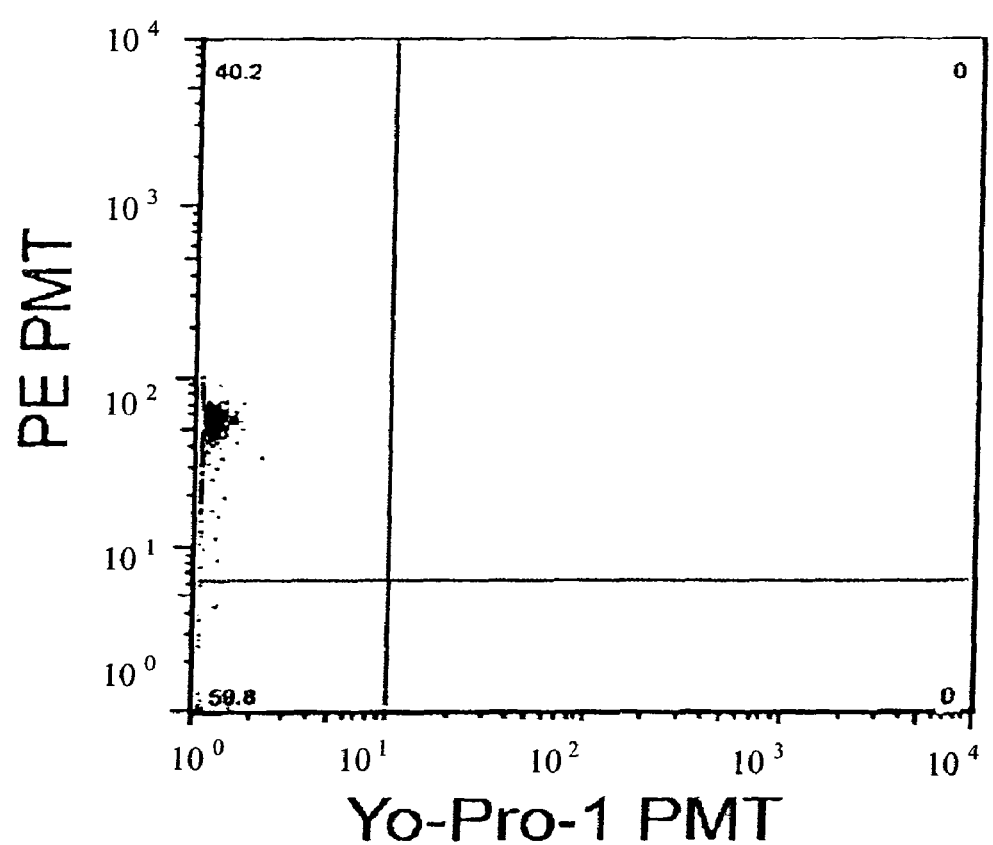
Figure 16:
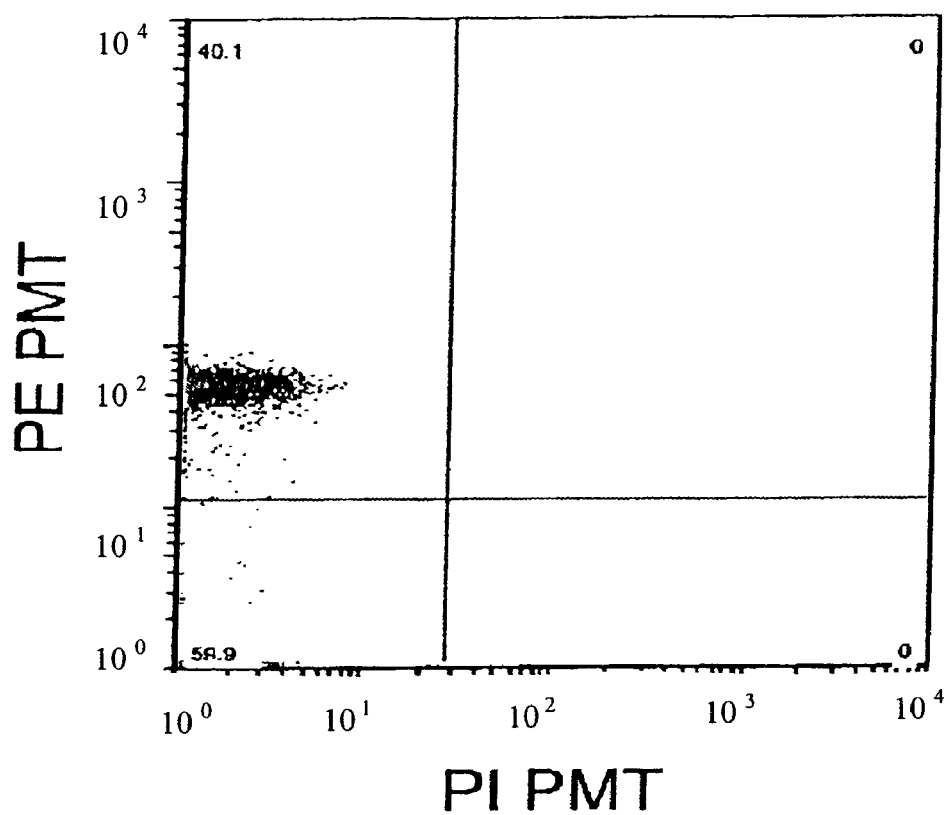

Samples of the FITC- and PE-labeled beads from the Calibrite bead kit (BD Biosciences, San Jose, Calif.) were prepared individually. The fluorescence contribution of YO-PRO-1 to the PE detector signal and that of PE to the YO-PRO-1 detector and the PI detector signals were calculated (FIG. 16). The contribution of positively stained beads was subtracted from detectors until the median fluorescence was equal to that of unstained beads in detectors in which they overlapped (FIG. 16).

Flow Cytometry Data and Statistical Analyses: For each sample, 10,000 CD14-$PE_{pos}$/$PI_{neg}$ events were acquired. Flow cytometry data was analyzed using FlowJo data analysis software (version 8.4. TreeStar, Inc., Ashland, Oreg.). The flow cytometry data files were uniformly gated in batch for CD14-PE positive events with or without PI negative selection. These events were then analyzed for the geometric mean fluorescence intensity of FL-1 YO-PRO-1 and comparisons were made between control- and BzATP-stimulated samples for each donor. Analysis was restricted to either $CD14_{pos}$ events or $CD14_{pos}$/$PI_{neg}$ events. The median fluorescence values for YO-PRO-1 are reported after saline- or BzATP-stimulation. In some cases, data are expressed as a BzATP-stimulated fold of YO-PRO-1 uptake, i.e. the ratio of these two measurements, to be consistent with our prior work (10,30). To reduce contributions from background uptake by non-$P2X_7$ mechanisms, data are expressed as a BzATP-stimulated fold of YO-PRO-1 uptake (10, 34). One-way ANOVA and students' t-tests were performed using the JMP 6.0 software package (SAS Institute, Cary N.C.).

Results.

Contribution of nonviable cells to analysis of pore activity. In preparation for a multi-center clinical trial with overnight shipping of samples, the methods of the present invention were adjusted to accommodate the effects of variable sample age. The primary result of processing samples hours to days following phlebotomy is the loss of viable cells. Accordingly, to facilitate the analysis of $P2X_7$ pore function as a continuous variable in larger epidemiological studies, the method of the present invention accommodates samples of varying age in a way that also maximizes platform flexibility and reduces potential for inter-laboratory variability.

FIG. 7A quantifies the decline in monocyte viability in whole blood samples stored at room temperature for up to four days post phlebotomy. Although the cell impermeant DNA intercalating cyanine dye YO-PRO-1 gains access to nuclear material after BzATP stimulation of the $P2X_7$ pore, it may also stain cells no longer possessing an intact plasma membrane. In aged samples, a second YO-PRO-1 positive population of BzATP-stimulated cells appears, which is minimally present in whole blood processed within a few hours of phlebotomy (FIG. 7B).

To assess viable monocyte activity in samples that contained a significant fraction of dead cells, it was necessary to include a second vital dye after $P2X_7$ pore closure to identify these cells. Therefore, flow cytometric analysis of YO-PRO-1 fluorescence detected in basal and BzATP-stimulated CD14-PEpos monocytes was conducted with or without propidium iodide (PI) addition at the end of the staining procedure (FIGS. 7A and 7B). Histogram analysis indicates similar basal YO-PRO-1 fluorescence detected in the cell populations selectively gated for viable (CD14-PEpos,PIneg) monocytes versus total (CD14-PEpos) monocytes (FIG. 7A; representative of twelve independent experiments). As expected, viable monocytes responded to BzATP challenge with an increase in $P2X_7$ pore function as indicated by a clear shift in detectable YO-PRO-1 fluorescence.

However, histogram analysis of YO-PRO-1 fluorescence detected in total monocytes following BzATP challenge indicates two distinct cell populations wherein the viable cells in the monocyte population exhibited a large shift in YO-PRO-1 fluorescence and the nonviable cells within the monocyte population presented little to no increase in YO-PRO-1 fluorescence compared to basal levels (FIG. 7A). FIG. 7B indicates the fold stimulation in BzATP-induced YO-PRO-1 fluorescence detected in live and total monocyte populations from twelve different donors. These data indicate a significant difference in the mean fold stimulation in BzATP-induced YO-PRO-1 fluorescence detected in live versus total monocyte populations (live=76.5±20.5 vs. total=32.5±6.2 expressed as mean±SEM; p=0.04). Thus to minimize the effects of variable sample age, exclusion of dead cells is required to measure true YO-PRO-1 fluorescence in monocytes following BzATP challenge as a measure of $P2X_7$ pore function.

To restrict the analysis to viable monocytes, the inclusion of a second vital dye after $P2X_7$ pore closure is thereby required. Flow cytometric analysis of YO-PRO-1 fluorescence detected in basal and BzATP-stimulated CD14-$PE_{pos}$ monocytes was conducted with or without propidium iodide (PI) addition at the end of the staining procedure. The results demonstrate that the exclusion of nonviable cells increases the apparent fold-uptake (viable=76.5±20.5 vs. total=32.5±6.2 expressed as mean±SEM, N=12; p=0.04). Thus, to minimize the effects of variable sample age, exclusion of non-viable cells is required to measure true YO-PRO-1 fluorescence in monocytes following BzATP challenge as a measure of $P2X_7$ pore function.

Effect of spectral overlap on measurements of $P2X_7$ pore function in live monocytes. The fluorochromes PE and PI exhibit spectral overlap, which requires fluorescence compensation in order to identify the live monocytes. To minimize operator- and platform-dependent differences in settings adjustment, the present study adapted methods of establishing fluorescent particle targeted PMT sensitivities and calculation of spectral overlap (29-33). The effect of calibrated versus fixed flow cytometer instrument settings on BzATP-induced YO-PRO-1 uptake by viable (CD14-PEpos/PIneg) monocytes was then examined.

After establishing appropriate compensation for PI (discussed below), Table 3 illustrates the effect of bead-adjusted versus recalled flow cytometer instrument settings on the day-to-day variability of control and BzATP stimulated YOPRO-1 fluorescence associated with viable (CD14-$PE_{pos}$/$PI_{neg}$) monocytes. Despite daily assessment of instrument performance and confirmation that our window of analysis is within the linear range for the machine (not shown), bead-adjusted PMT voltage settings reduced day-to-day variability of these measurements in comparison to those obtained with recalled settings (Table 3).

eliminate the confounding influence of an overwhelming number of RBCs that would influence the targets for appropriate compensation (30), and used to create a bead file in order to standardize compensation methods in whole blood using fluorescent particles as a surrogate for single color controls.

FIGS. 8A and 8B are representative CD14-PE versus PI dot plot analyses of monocytes acquired using fixed and calibrated instrument settings, respectively (representative dot plots of six independent experiments). The fixed instrument settings used previously have suboptimal delineation between viable (indicated with a gate) and nonviable monocyte populations, indicating insufficient compensation between PE and PI detectors (FIG. 8A). A clear separation between viable monocytes (CD14-PEpos/PIneg; indicated with a gate) and nonviable monocytes (CD14-PEpos/PIpos) is exhibited using standardized PMT setting and appropriate spectral overlap calculation for sample acquisition, thereby allowing for a uniform acquisition gate (FIG. 8B). As expected, the standardized method (fixed vs. calibrated) did not significantly alter the results (not shown). However, the use of optimized instrument settings facilitated post acquisition data analysis in identifying viable monocytes (CD14-PEpos/PIneg) for subsequent examination of $P2X_7$ receptor phenotypes in the context of a clinical study.

Figure 9:
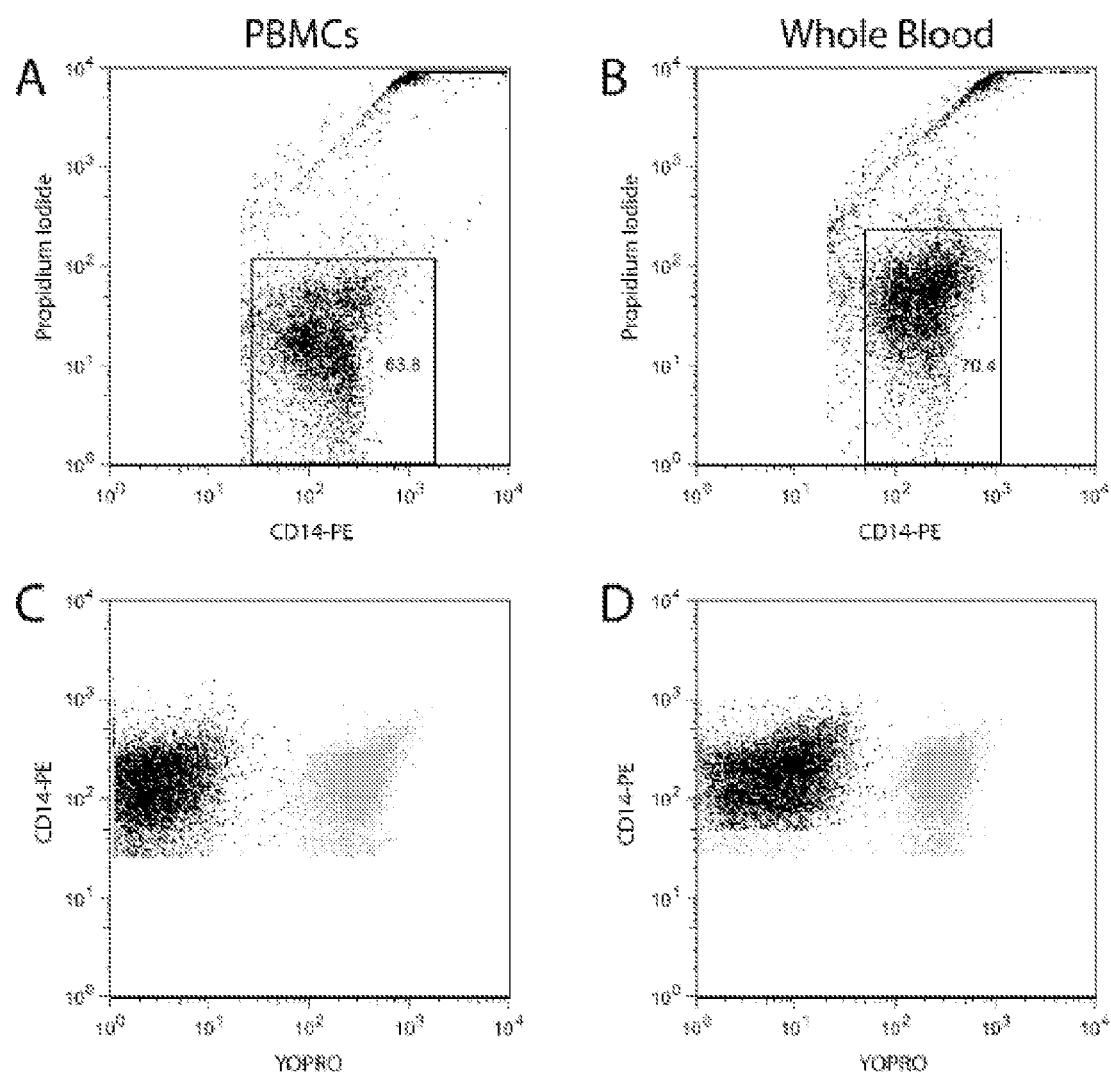
FIGS. 9A-9D show representative display of fluorescence of the pore assay reagents with the use of instrument sensitivities and compensation determined with beads as described in Materials and Methods.

FIGS. 9A and 9B show PI vs. PE dot plots of PBMCs and whole blood using this bead-adjusted compensation method. A viable PE-$CD14_{pos}$ population is readily identified in both samples, allowing for appropriate data restriction when collecting YO-PRO-1 fluorescence measurements in control and BzATP treated samples (FIGS. 9C and 9D). Additionally, Table 4 shows the influence on three different compensation methods on the stability of YO-PRO-1 measurements in PBMCs or whole blood. Specifically, we compared our bead adjusted compensation method to a fixed setting as well as to measurements derived from data that are compensated after acquisition. The unstimulated YO-PRO-1 fluorescence measurements, and thereby the fold-uptake, vary considerably depending on the compensation method used.

TABLE 3

| Donor | YO-PRO-1 Measurement | PMT Method | Mean | Standard Deviation | Coefficient Of Variance |
|---|---|---|---|---|---|
| Low Responder | Unstimulated | Recalled | 4.6 | 1.6 | 0.35 |
| | | Bead Adjusted | 4.0 | 0.8 | 0.20 |
| Normal Responder | Unstimulated | Recalled | 2.2 | 0.6 | 0.26 |
| | | Bead Adjusted | 2.8 | 0.3 | 0.12 |
| Low Responder | BzATP Stimulated | Recalled | 30.0 | 6.3 | 0.21 |
| | | Bead Adjusted | 30.1 | 2.5 | 0.08 |
| Normal Responder | BzATP Stimulated | Recalled | 983.0 | 154.9 | 0.16 |
| | | Bead Adjusted | 1019.0 | 118.7 | 0.12 |
| Low Responder | Fold Uptake | Recalled | 6.8 | 1.4 | 0.20 |
| | | Bead Adjusted | 7.7 | 2.0 | 0.26 |
| Normal Responder | Fold Uptake | Recalled | 469.7 | 170.9 | 0.36 |
| | | Bead Adjusted | 365.4 | 63.7 | 0.17 |

The fluorochromes PE and PI exhibit spectral overlap, which requires fluorescence compensation in order to identify the live monocytes. The requirement of a fluorescent tag to identify monocytes precludes single color compensation controls for whole blood samples. PBMCs were purified to

TABLE 4

| Preparation | Compensation | Unstimulated | BzATP Stimulated | Fold-Increase |
|---|---|---|---|---|
| Ficoll prep PBMC, A | Bead-Adjusted | 2.26 | 292 | 129.20 |
| Whole blood, A | Bead-Adjusted | 5.84 | 276 | 47.26 |
| Whole blood, B | Uncompensated | 8.27 | 30.7 | 3.71 |
| Whole blood, B | YO-PRO-PE Set at 2% | 4.59 | 27.4 | 5.97 |
| Whole blood, C | Uncompensated | 5.97 | 1071 | 179.40 |
| Whole blood, C | YO-PRO-PE Set at 2% | 2.61 | 1067 | 408.81 |

By contrast, the BzATP stimulated median YO-PRO-1 fluorescence appears reasonably independent of the compensation strategy (Table 4). Collectively, these data demonstrate that the bead-adjusted setup method for both PMT voltages and compensation calculation further reduce intra-laboratory variability when viable monocyte associated YO-PRO-1 fluorescence is measured in BzATP stimulated whole blood samples.

Figure 11:
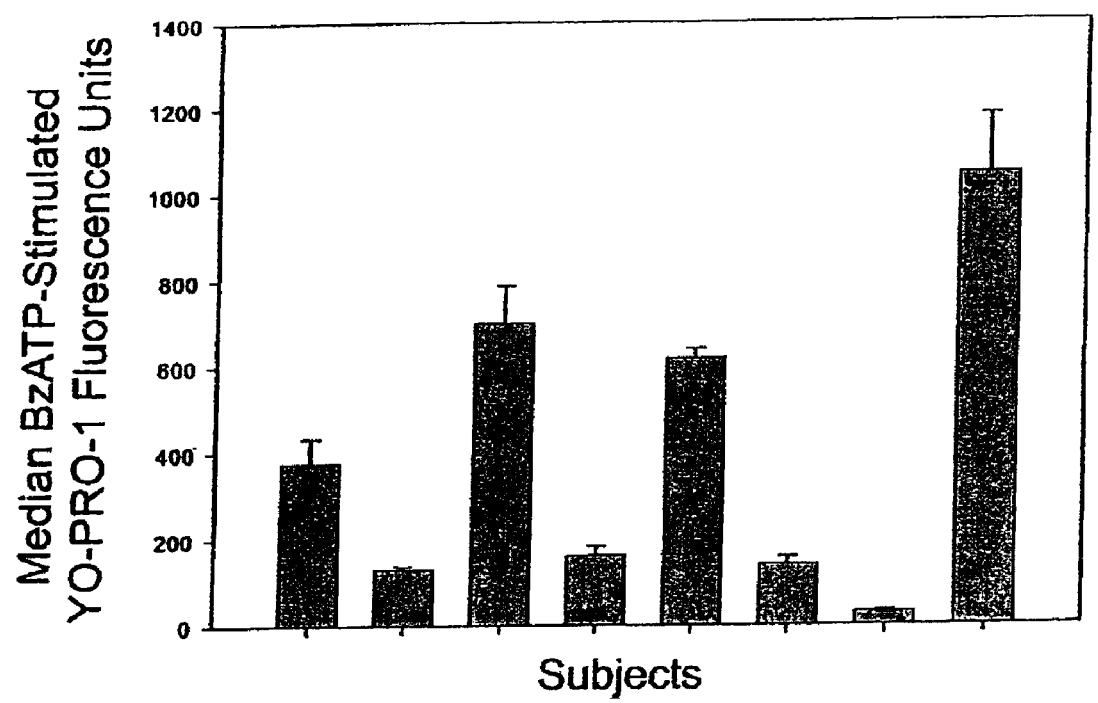
FIG. 11. Effect of day-to-day phlebotomy on measured P2X$_7$ pore function in live monocytes. Staining and standardized calibration of FACSCalibur settings was conducted (see Methods) and 10000 CD14-PE$_{pos}$/PI$_{neg}$ events were collected. Data indicate the fold stimulation in BzATP-induced YO-PRO-1 uptake by live (CD14-PE$_{pos}$/PI$_{neg}$) monocytes acquired on 3 different days within a three-month span from eight different donors.

Combined Estimates of Biological Systematic Variability. Because $P2X_7$ mRNA and protein expression is enhanced by inflammatory cytokines such as IFN-γ, subtle changes in systemic inflammation from any one donor could vary from day to day (31). Therefore, peripheral blood was obtained from eight different individuals without any apparent cold symptoms on three different days throughout a three-month period. FIG. 11 shows the means and standard deviations of the BzATP-induced YO-PRO-1 fluorescence in viable monocytes for these eight subjects measured on three independent days.

The average day-to-day coefficient of variance is 0.11±0.04. Of note, the BzATP-induced fold of dye uptake was more variable from day-to-day especially in normal responders (average CV 0.25±0.28), likely due in part to the compensation differences affecting the basal values in this ratio as discussed above. These data strongly suggest that measurements of $P2X_7$ pore activity by viable monocytes in blood obtained on different days is reliable, particularly when the raw BzATP-induced YO-PRO-1 fluorescence data are reported. These results provide a standardized method for quantitative flow cytometric analysis of $P2X_7$ receptor phenotypes in blood monocytes with minimal intra-laboratory variation.

Instrument- and operator-dependent differences have been shown to contribute to inter-laboratory variation in quantitative flow cytometry for clinical studies, particularly in the absence of a standardized set up protocol (32, 33). Standardization of PMT sensitivities and spectral overlap calculation minimizes both platform and day-to-day variation and permits intra- and inter-laboratory comparisons (32). Previously, the whole blood $P2X_7$ pore assay was performed exclusively a FACScan (10,34).

Figure 12:
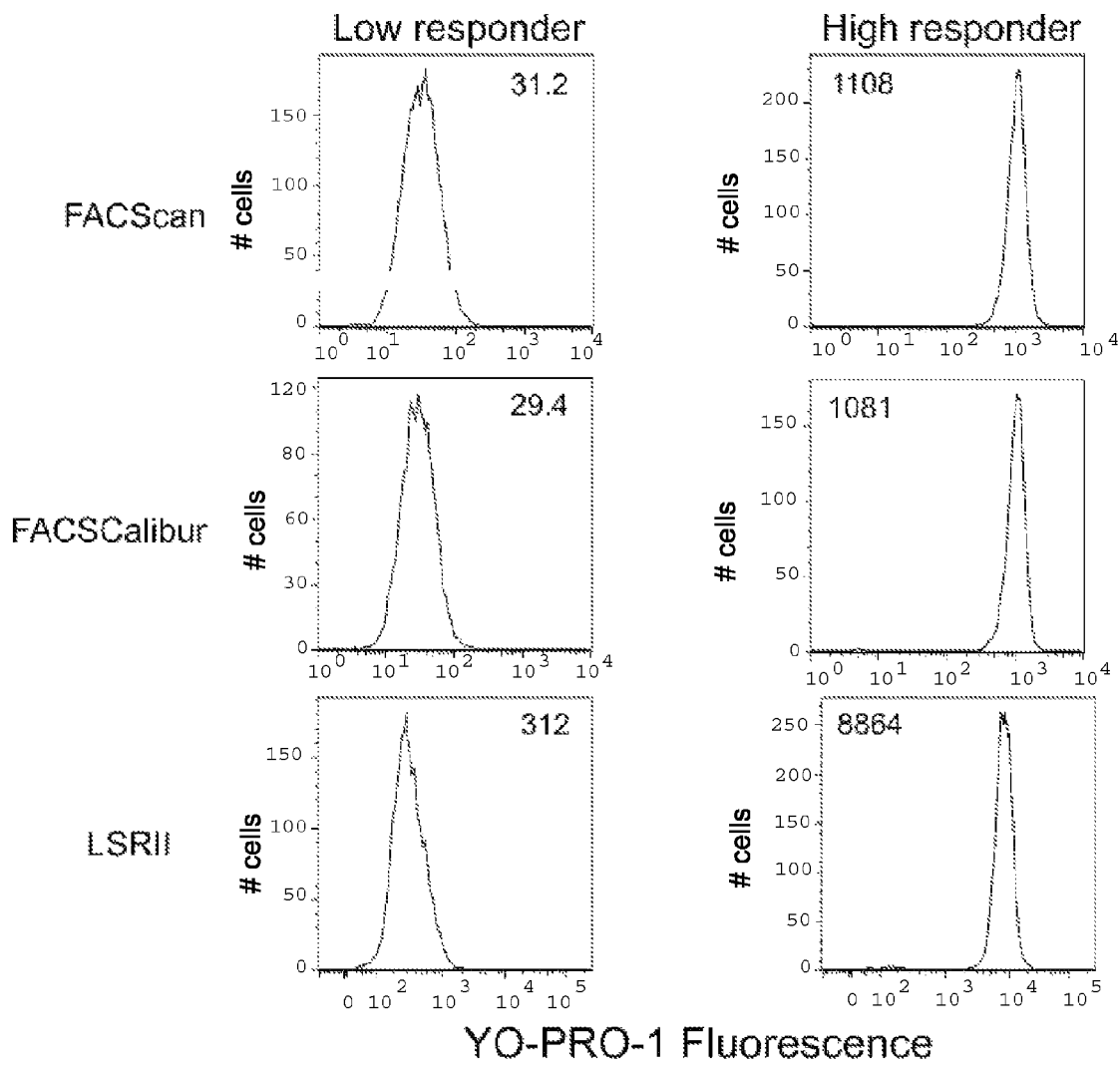
FIG. 12. Comparative histograms of the YO-PRO-1 fluorescence of monocytes stimulated with BzATP in two donors: one low responder and one high responder. Data was acquired on the same sample on three different flow cytometers: FACScan, FACSCalibur, and the LSRII. The instruments were set using two sets of target values as described. The FACScan and FACSCalibur used the same values while the LSRII used a different set of values. Median intensities of live monocytes are given for each instrument.

The inventors' next endeavored to increase platform independence and inter-laboratory reproducibility. To measure the differences between instruments, the same samples from eleven volunteers were analyzed on each cytometer in the facility that includes two analog instruments (FACScan and FACSCalibur) and a digital cytometer (LSR II). FIG. 12 shows representative histograms of the BzATP-stimulated YO-PRO-1 fluorescence for a low responder and a normal responder processed on the same day on three different flow cytometers (FACScan, FACSCalibur, and LSR II).

Figure 10:
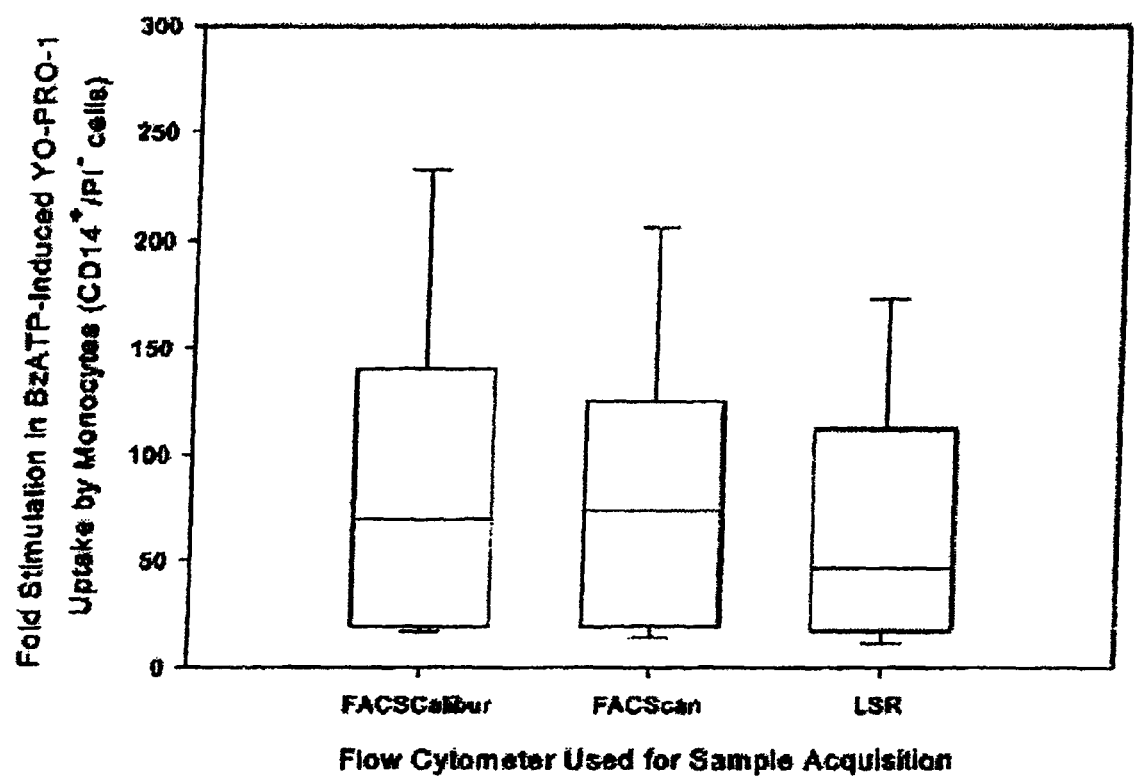
FIG. 10. Fold stimulation in BzATP-induced YO-PRO-1 uptake by live monocytes as detected by FACScan, FACSCalibur and LSR II using calibrated instrument settings. Cell staining was performed by one operator (see Methods) and the samples were subsequently aliquoted. Standardized calibration of FACScan, FACSCalibur, and LSR II settings was conducted independently by three operators (see Methods) and 10000 CD14-PE+/PI– events were collected using a different instrument simultaneously for aliquots of the same sample. Data are presented as the fold change in the geometric mean of YO-PRO-1 fluorescence detected in live monocytes following exposure to control vehicle or BzATP, as acquired by the FACScan, FACSCalibur, and LSR II instruments. Box and whisker plot analysis is shown with representation of median, interquartile range, and 95th percentile confidence interval values (n=10; ANOVA p=0.78).

In general, the cytometers that use logarithmic amplifiers have very comparable measurements, while the LSR II that processes signals digitally and does not use logarithmic amplifiers has different values. Specifically, when comparing data obtained from all eleven volunteers, the absolute difference between intra-subject measurements on the two analog instruments (FACScan and FACSCalibur) was 2.0±1.5 percent of the average BzATP-stimulated YO-PRO-1 fluorescence. FIG. 10 shows the effect of using different flow cytometers (FACScan, FACSCalibur, and LSR II) to evaluate pore activity. These data indicate that standardized calibration of instrument settings on the FACScan, FACSCalibur and LSRII resulted in comparable fold stimulation in BzATP-induced YO-PRO-1 uptake by live monocytes (ANOVA, p=0.78), indicating there is more variability within the group of subjects than there is between a collective assessment of the instruments and operators.

As shown in FIG. 12, data collected with the bead-adjusted method on the LSR II produces histogram results similar to those obtained on analogue machines, when these values are considered in proportion to the total window of analysis for each instrument. Although the fold stimulation in BzATP-induced YO-PRO-1 uptake by variable monocytes (vs. the saline control) was similar across all three platforms (ANOVA, p=0.78), the raw values for BzATP-induced YO-PRO 1 fluorescence obtained on the LSR II were 9.0±0.8 times higher than the average values measured on the FACScan and the FACSCalibur. Collectively, these data indicate that the bead-adjusted setup method reduces systematic variability associated with raw fluorescence measurements and can be used to obtain comparable results on different instruments and analysis platforms.

The inventors also evaluated the day-to-day variation in phlebotomy. Because $P2X_7$ expression is enhanced by inflammatory cytokines such as IFN-, subtle changes in systemic inflammation from any one donor could vary from day to day (37). Therefore, peripheral blood was obtained from six different individuals without any apparent cold symptoms on three different days throughout a three-month period. FIG. 11 demonstrates that day-to-day phlebotomy caused modest variability in BzATP-induced YO-PRO-1 uptake by viable monocytes from each donor (average coefficient of variance=0.12±0.02). These data strongly suggest that measurements of $P2X_7$ pore activity by viable monocytes in blood obtained on different days is reliable and that any significant variation in $P2X_7$ pore function acquired from an individual on different days may be attributed to a secondary effect. These results provide a standardized method for quantitative flow cytometry analysis of $P2X_7$ receptor phenotypes in blood monocytes with minimal intra-laboratory variation.

Assay Compatibility with Aged Samples in an Ongoing Multi-Center Asthma Clinical Trial. The evaluation of $P2X_7$ pore function as a predictor of symptoms and other clinical endpoints involves overnight shipping of room temperature blood samples to our facility. Accordingly, the median sample age is one day post-phlebotomy with the following interquartile range (1, 2.25; samples collected locally are processed on the same day recorded here as day zero).

Figure 13:
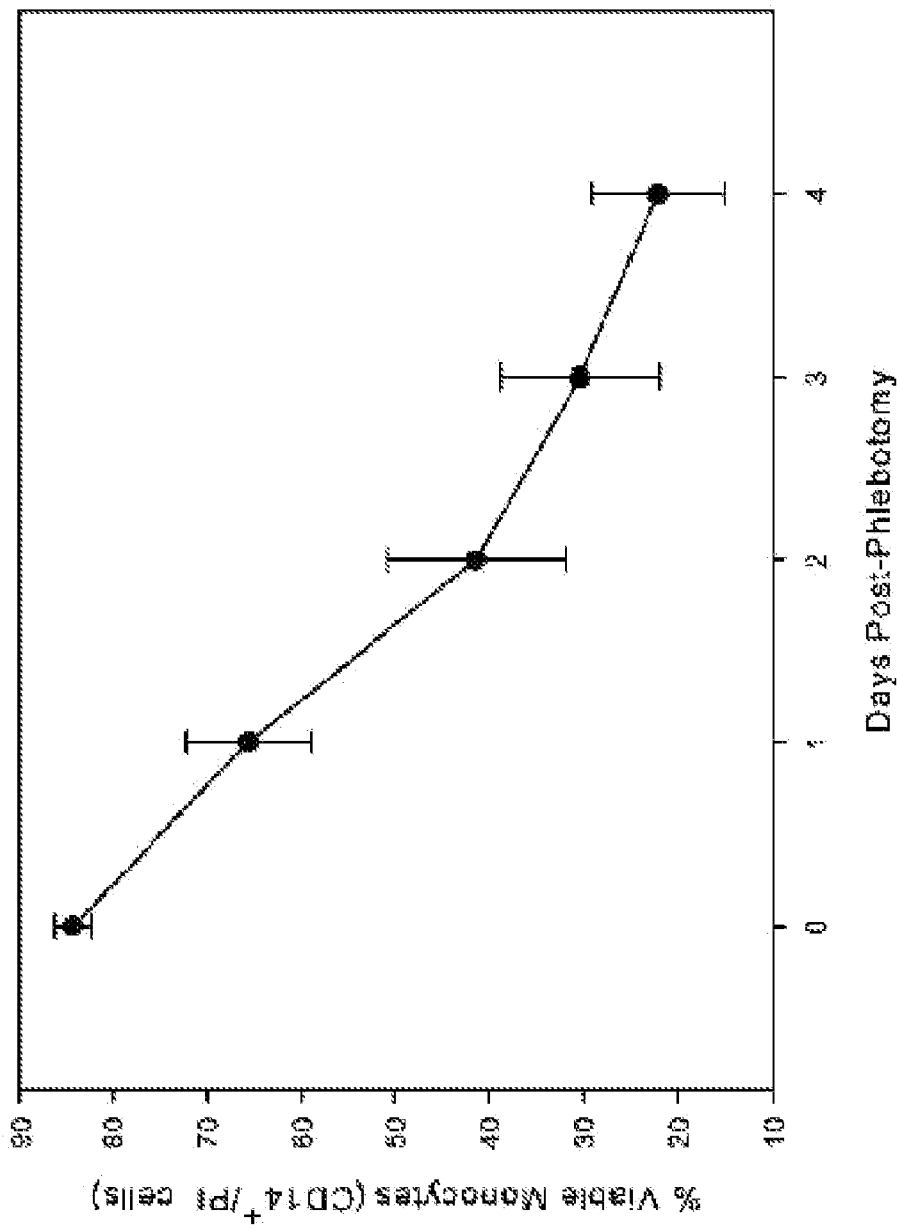
FIGS. 13A-C show the effect of peripheral blood age on viability and P2X$_7$ pore function in monocytes. To prepare for the multi-center ACRN-MIA clinical trial, peripheral blood was obtained from eight laboratory volunteers and processed immediately or stored at room temperature for up to four days to emulate the conditions of overnight shipping and five-day/week processing. On the day of processing, aliquots of the blood samples were stained and standardized calibration of FACSCalibur settings was performed as described in the Methods section with collection of 10000 (CD14-PEpos/PIneg) events.
Figure 13:
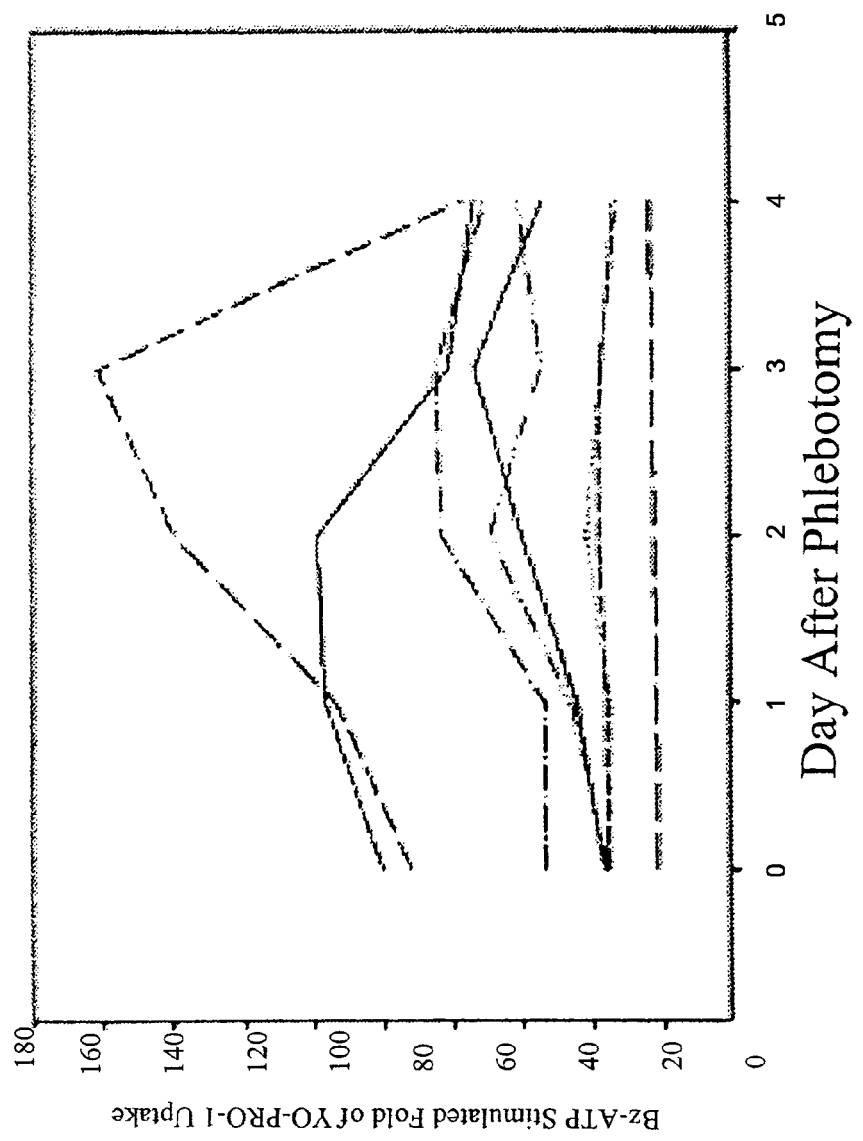
Figure 13:
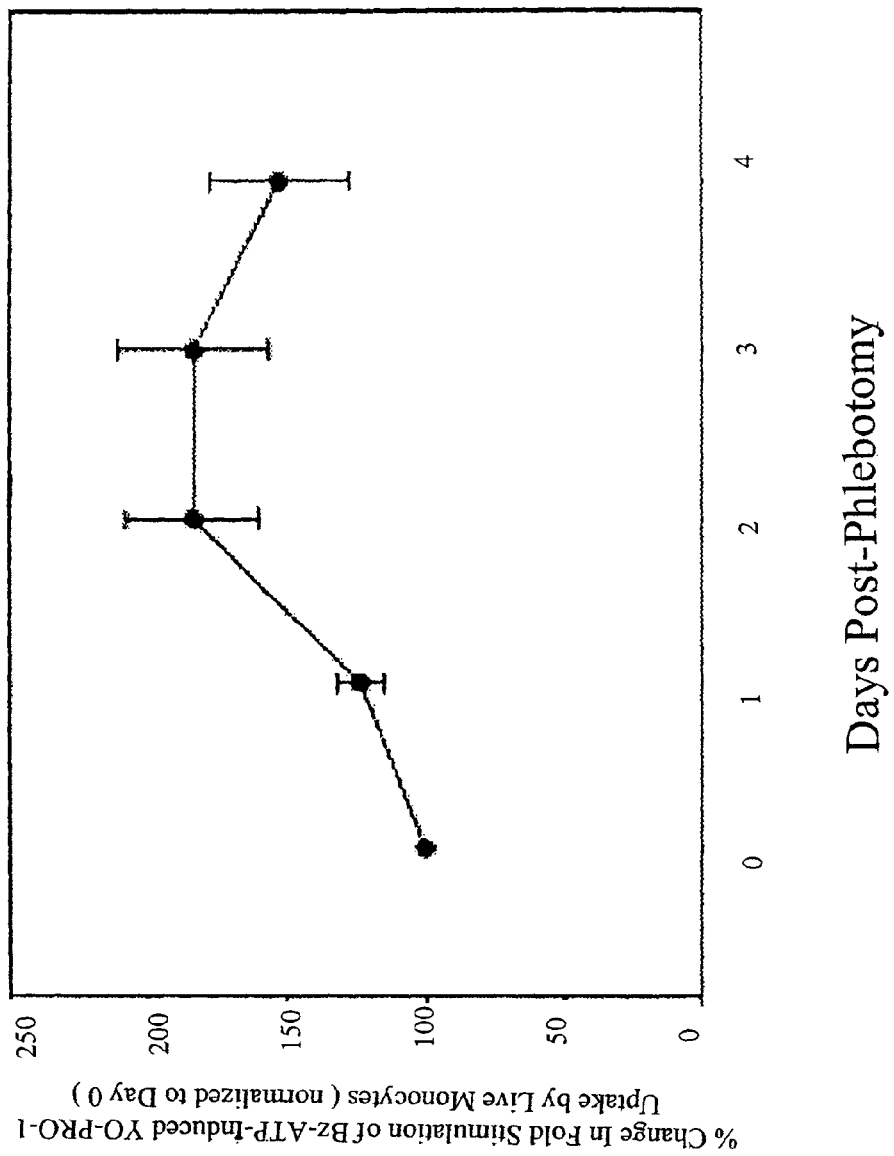

Because preliminary data suggested whole blood sample stability for at least 24 hr, the inventors chose an overnight shipping strategy with central, five day/week processing to minimize training costs and setup variability. FIG. 13A demonstrates that monocyte viability at room temperature in citrate anti-coagulated whole blood rapidly declines over a five-day period in samples from laboratory volunteers (n=8). Monocyte viability in the multi-center clinical trial samples is consistent with these data (data not shown; n=68), suggesting that the shipping process at room temperature does not accelerate sample decay. Time course experiments with the samples from laboratory volunteers show that sample age is associated with augmentation of $P2X_7$ pore function in monocytes compared to day zero baseline in all of the subjects tested (FIG. 13B).

Moreover, when these data are expressed as the percent change from the day zero baseline, the variance is small enough to permit use of correction factors for the effects of sample age (FIG. 13C). These correction factors are 1.23, 1.84, 1.84, and 1.53 for days one through four respectively post-phlebotomy.

Figure 14:
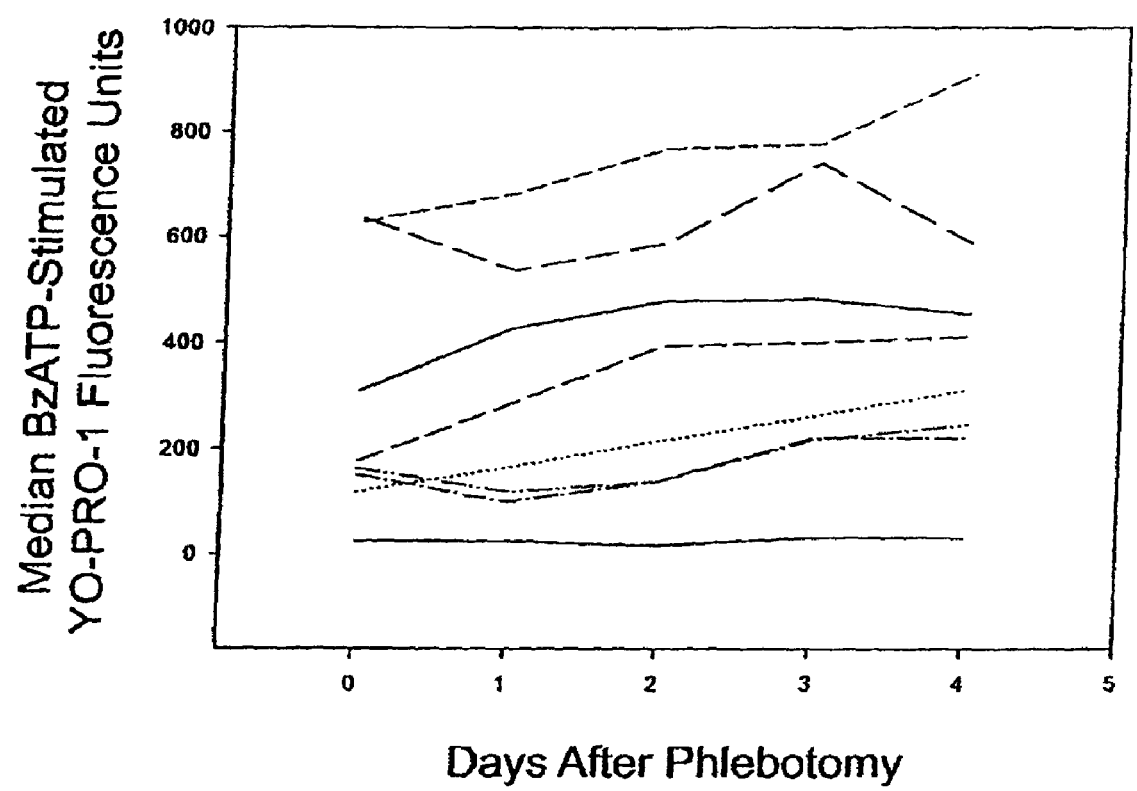
FIG. 14. Median fluorescence intensities of YO-PRO-1 in live monocytes stimulated with BzATP. Blood was drawn from eight different donors and aliquots of each blood was assayed daily for five days. All data was acquired on a FACSCalibur flow cytometer using bead-adjusted settings.

To assess the impact of declining monocyte viability on the performance of the present assay, time course experiments with samples from laboratory volunteers were performed with serial processing on multiple days after sample collection (FIG. 14). Samples from four of the eight subjects appear to have a progressive rise in BzATP stimulated YO-PRO-1 fluorescence, whereas the other four specimens do not have an appreciable change. Analysis of variance suggests there is more variability between subjects in this regard than there is with respect to time (p=0.814).

When the data are expressed as a percent of each subject's Day Zero measurement, there may be a trend towards rising values that could reach significance if more subjects were studied. Specifically, Day One is 108.2±34.4%, Day 2 is 126.5±55.1%, Day 3 is 156.6±43.3% and Day 4 is 162.4±56.5% of the values obtained on Day 0 (ANOVA p=0.104). Thus the exclusion of non-viable monocytes with our bead-adjusted setup method can accommodate samples of varying age.

Moreover, Table 5 shows descriptive statistics from clinical samples using our past (fixed settings, total $CD14_{pos}$ cells) and current (bead-adjusted, nonviable-excluded) methods from a local and multi-center asthma protocol, respectively. The distributions of these datasets from reasonably similar patient populations appear unchanged (Table 5, p=0.846), suggesting that the revised method has not influenced the data while improving intra-laboratory reproducibility. In sum, the use of these derived correction factors for sample age on BzATP-induced $P2X_7$ pore function by monocytes facilitates clinical trials with delayed flow cytometry processing without impact on $P2X_7$ receptor phenotypes.

TABLE 5

|  | Natural Cold Data (Recalled Settings) N = 31 | ACRN-MIA Data (Bead-adjusted settings) N = 99 |
| --- | --- | --- |
| Minimum | 13.8 | 2.3 |
| $1^{st}$ Quartile | 359 | 274 |
| Median | 669.5 | 598 |
| $3^{rd}$ Quartile | 992 | 893.5 |
| Maximum | 1676 | 1666 |

REFERENCES FOR EXAMPLE 4

1. Khakh, Nature 2006;442 (7102):527-32.
2. Rassendren, J Biol Chem 1997;272 (9):5482-6.
3. Buell, Receptors Channels 1998;5 (6):347-54.
4. Di Virgilio, Blood 2001;97 (3):587-600.
5. Gu, Am J Physiol Cell Physiol 2000;279 (4):C1189-97.
6. Mehta, J Biol Chem 2001;276 (6):3820-6.
7. Tonetti, Biochem Biophys Res Commun 1995;214 (1): 125-30.
8. Perregaux, J Immunol 2000;165 (8):4615-23.
9. Hu, J Biol Chem 1998;273 (42):27170-5.
10. Denlinger, J Immunol 2005;174 (7):4424-31.
11. Li, J Infect Dis 2002;186 (10):1458-62.
12. Fernando, Am. J. Resp. Critical Care Medicine 2006;175: 360-366.
13. Nino-Moreno, Clin. Exp Immunol 2007;148 (3):469-77.
14. Denlinger, Clin. Chem. 2006;52 (6):995-1004.
15. Gordon, J Clin. Invest 2005;115 (6):1408-18.
16. Rifai, Nat. Biotechnol. 2006;24 (8):971-83.
17. Gudipaty, Am J Physiol Cell Physiol 2001;280 (4):C943-53.
18. Akbari, N Engl J Med 2006; 354 (11):1117-29.
19. Vijayanand, N Engl J Med 2007; 356 (14):1410-22.
20. Bayer, Cytometry B Clin. Cytom. 2007;72 (1):8-13.
21. Roederer, Cytometry 2001;45 (3):194-205.
22. Schwartz, Cytometry 1996;26 (1):22-31.
23. Schwartz, Cytometry 1998;33 (2):106-14.
24. Waxdal, Cytometry 1998; 33 (2):213-8.
25. Brown, Am J Clin. Pathol. 1994;101 (5):630
26. Zhang, Cytometry 1998;33 (2):244-8.
27. Fluorescence Calibration and Quantitative Measurement of Fluorescence Intensity; Approved Guideline Clinical and Laboratory Standards Institute. Report nr I/LA24-A Vol. 24, No. 26.
28. Schwartz, Cytometry B Clin. Cytom. 2004;57 (1):1-6.
29. Davis, Lab Hematol. 1995;1:3-12.
30. Denlinger, J Endotoxin Res 2004;10 (2):137-42.
31. Humphreys, J Leukoc Biol 1998;64 (2):265-73.
32. Zenger, Cytometry 1998;33 (2):138-45.
33. Levering, Cytometry B Clin. Cytom. 2007;72 (3):178-88.
34. Xu, Am J Hum Genet. 2000;67 (5):1163-73.
35. Malerba, Am J Respir. Crit. Care Med 2000;162 (4 Pt 1):1587-90.
36. Raby, Hum Mol Genet. 2003;12 (16):1973-9.
37. Celedon, Hum Genet. 2007;120 (5):691-699.
38. Coutinho-Silva, Am J Physiol Cell Physiol 2001;280 (1):C81-9.
39. Coutinho-Silva, Immunity 2003;19 (3):403-12.
40. Johnston, Am J Respir. Crit. Care Med 2005;172 (9): 1078-89.

Example 5

A Rapid, High-Throughput, Genomically-Validated, Functional Screening Assay

This example describes a rapid, high-throughput, genomically-validated, functional screening assay in whole blood applied to correlating $P2X_7$ pore activity with neutrophilic airway response to an upper respiratory tract infection and loss of asthma control.

Methods and Materials

Human Subject Participation. All investigations were approved by the Human Subjects Committee of the University of Wisconsin's Health Sciences Institutional Review Board, with written, informed consent and in accordance with the guidelines established by the revised Declaration of Helsinki. Genetic analysis was approved as an ancillary protocol with an independent consent process and subject numbering system. Subjects with allergic asthma were recruited from an established database of over three thousand participants prior to expected Rhinovirus cold seasons (Spring and Fall) with instructions to call the study coordinators within 48 hr of a new upper respiratory tract infection. This recruitment was expanded via a mass email.

Inclusion criteria comprised the following: a) age of eighteen to forty-five years, b) physician diagnosis of asthma based on episodic symptoms of cough, wheeze and dyspnea established at least six months prior to enrollment, c) asthma medications consisting of as needed short acting $\beta_2$ agonists, low dose inhaled corticosteroids ($\leq$400 mcg beclomethasone/day or equivalent), or the combination product Advair® equivalent to low dose inhaled corticosteroids, d) database records of $FEV_1 \geq 70\%$ of predicted, e) prior history of $FEV_1$ reversibility with $\beta_2$ agonist $\leq$12% or methacholine $PC_{20}$<8 mg/ml, and f) skin test reactivity to at least one aeroallergen. Subjects were not eligible to participate if they had a history of severe asthma during upper respiratory tract infection including an increase of 6 puffs/day from baseline of short-acting bronchodilator use during an acute infection, were a current smoker or had a history of $\geq$five pack-yrs, were currently on immunotherapy, or had been enrolled in another clinical study within one month prior to the initial visit.

Figure 17:
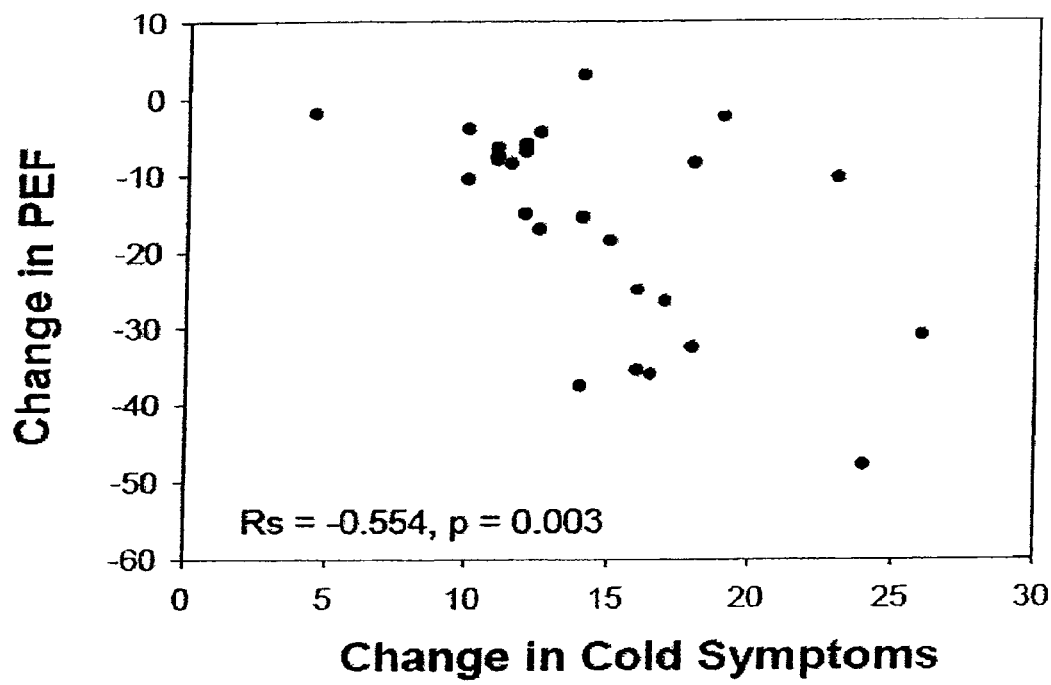
FIGS. 17A and 17B show correlations of the change in peak flow to changes in cold and asthma symptoms.
Figure 17:
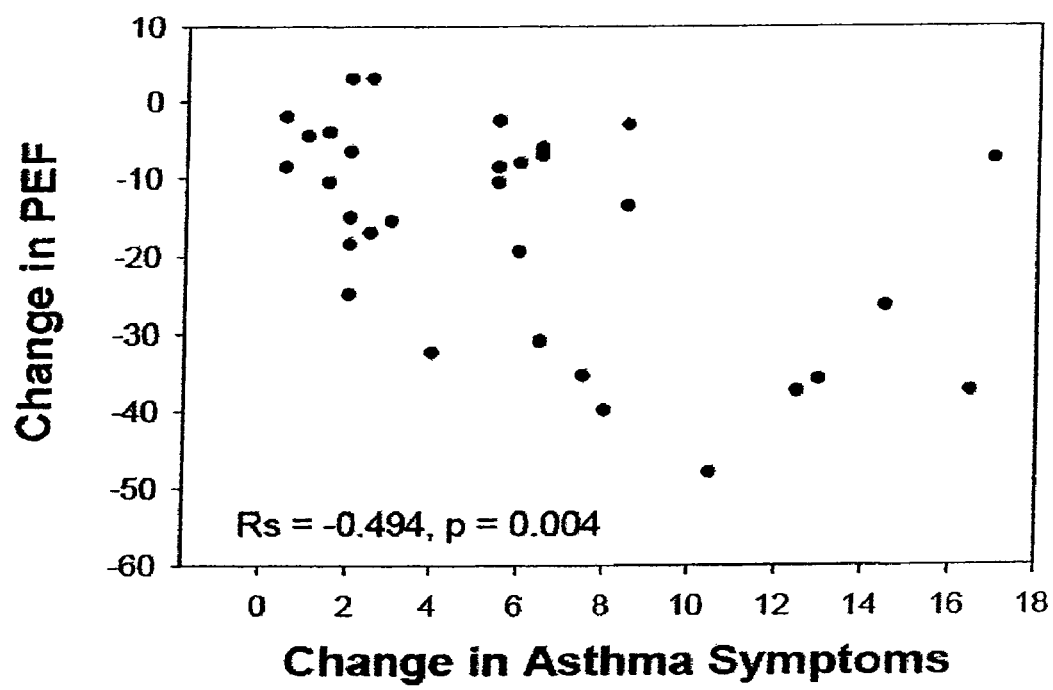

Asthma Phenotyping Protocol. Subjects were asked to complete four visits within the first week of cold symptoms, followed by two visits when their cold symptoms returned to baseline at least six weeks later (FIG. 17). Cold symptoms were assessed by the modified-Jackson survey instrument four time a day via subject diaries. Similarly, asthma symptoms and peak flow diaries were completed twice a day. Nasal lavage was performed at each visit for a cell count and differential as well as for a multicode PCR method of detecting over one hundred respiratory viruses. Induced sputa were collected twice during the acute phase and once at baseline for a cell count and differential. Serum samples for *Chlamydia* pneumoniae and Mycoplasma pneumoniae IgM, IgG and IgA detection from were collected at one acute and one baseline, stored at −80° C., and performed at the end of the study using a ELISA kits according to manufacturers instructions (Savion). Spirometry was performed at each visit and a methacholine challenge was done on the visits corresponding to sputum induction; both of which were performed according to ATS guidelines.

$P2X_7$ Pore Assay and Genotyping. Citrate- and EDTA-anticoagulated whole blood samples were collected for the pore assay and genotyping respectively during at least one acute and/or baseline visit. Methods for these assays have been previously described. Briefly, monocytes were detected in the context of whole blood by a CD14+ threshold flow cytometric technique and the amount of fluorescent-dye uptake (YO-PRO-1) was quantified after a 20 min stimulation with saline with and without 250 μM Bz-ATP, a $P2X_7$ agonist. Dead cells were excluded from the analysis by gating around the YO-PRO positive population that appeared in both the agonist and the saline stimulated samples, distinct from the agonist-inducible population that also had higher CD14 staining.

Data are reported as the agonist-induced fold of YO-PRO-1 uptake by these cells, as previously validated. When pore assay data from an acute and baseline visit were available from samples processed within 24 hrs, the average of these values was reported. Finally, genomic DNA was harvested using the PureGene kit and genotyping was performed by restriction fragment length polymorphism analysis of polymerase chain reaction products, as previously described.

Recombinant Expression and Functional Characterization of Variant P2RX7 Alleles. A pcDNA3 expression vector containing a cloned human P2RX7 cDNA associated with normal pore activity was subjected to point mutagenesis using the Quick Change Kit (Stratagene Inc., city, state) to create the variants $P2X_7$-G150R, $P2X_7$-Q460R, and $P2X_7$-E496A. HEK 293 cells were transfected by the Superfect liposomal method and stable populations were selected by G418 resistance. Expression of $P2X_7$ mRNA and protein in unstimulated transfected HEK cell cultures was verified by RT-PCR and immunoblotting as previously described.

Transfected HEK cells were washed in HEPES-buffered saline (HBS; 130 mM NaCl, 5 mM KCl, 20 mM HEPES-pH 7.4, 0.1% BSA, and 10 mM glucose, components from Sigma-Aldrich, St. Louis Mo.), stimulated for 20 min at room temperature with various concentrations of 2'-3'-O-(4-benzoylbenzoyl)adenosine 5'-triphosphate (BzATP, 0 or 1 to 300 μM) in the presence of 1 μM YO-PRO-1 (Molecular Probes, city, state), equilibrated to 10 mM $MgCl_2$, and washed again in HBS. YO-PRO-1 fluorescence was measured by a Synergy-HT fluorescent plate reader (Biotek, city, state) using X±Y nm excitation and A±B emission filters.

Statistical Analysis: Calculations and data transformations where necessary were performed with Excel (Office 2004, v 11.3.6, Microsoft, Redding Wash.). Statistical analysis was done in JMP (v 6.0, SAS Institute, city, state). A receiver-operator curve was constructed as described previously using three validated loss of function P2RX7 alleles (E496A, I568N, and R307Q). The recently described compound heterologous loss-of-function genotype was added in to the model (E496A-T348A), as were heterozygotes for the G150R locus. The optimal performance characteristics were defined at a threshold of pore activity associated with the greatest Jaeger statistic (ref).

Pore activity was treated as a continuous variable and the ranked Spearman correlation coefficient was calculated for associations with clinical and biomarker data. Normal distributions of the raw or transformed datasets were confirmed with the goodness of fit test. Univariate regression analysis by the least squares method was used to model factors associated with the change in asthma symptoms during a naturally occurring cold, followed by a multivariate-stepwise model. For all tests, the significance level was set a 0.05.

Results.

Subject Characteristics. Table 6 documents the clinical characteristics for the mild-to-moderate allergic asthmatics in this study both during the acute phase of their upper respiratory tract infection and after recovery. All subjects had an elevated modified Jackson cold survey symptom score upon enrollment that decreased significantly at the recovery visits (17.8±5.9 vs. 2.6±3.6). Twenty-two of thirty-four subjects (64.7%) had a respiratory virus detected in nasal lavage fluid, the majority of which was rhinovirus. Thirty of thirty-four subjects (88.2%) had serology documentation of prior exposure (positive IgG or IgA) to either *Chlamydia pneumoniae* or *Mycoplasma pneumoniae*.

Despite this, none had a convincing pattern of acute infection (positive IgM, rising IgG titer) by these atypical bacteria. All subjects has higher peak asthma symptom scores during the cold than at recovery (7.7±5.3 vs. 0.5±1.4). As expected, the changes in either the cold or the asthma symptoms scores (acute minus recovery) inversely correlate with the change in daily peak flow recordings (FIG. 17). Using the Asthma Clinical Research Network definition of exacerbation evaluating symptom severity, treatment modification changes in lung function, eleven subjects experienced a mild decline in asthma control whereas 4 subjects had a severe exacerbation.

Table 6 illustrates asthma severity and symptom scores at the acute and baseline visits. Thirty-five subjects were enrolled and thirty-three completed. The median and interquartile range of the age distribution was 20 (18, 23). Seventeen of thirty-five subjects were male.

TABLE 6

| | ACUTE COLD | COLD RESOLUTION BASELINE |
|---|---|---|
| PEAK COLD SYMPTOM SCORE | 17.8 ± 5.9 | 2.6 ± 3.6 |
| PEAK ASTHMA SYMPTOM SCORE | 7.7 ± 5.3 | 0.5 ± 1.4 |
| FEV1 % predicted | 89.2 ± 13.3 | 95.9 ± 12.1 |
| METHACHOLINE $PC_{20}$ (mg/ml; median, IQR) | 1.5 (0.6, 3.6) | 1.3 (0.5, 4.2) |
| VIRUS DETECTION | 22 of 34 subjects | |
| C. pneumoniae/M. pneumoniae serology | 0 of 34 with acute profile | 30 of 34 with prior exposure |

Figure 18:
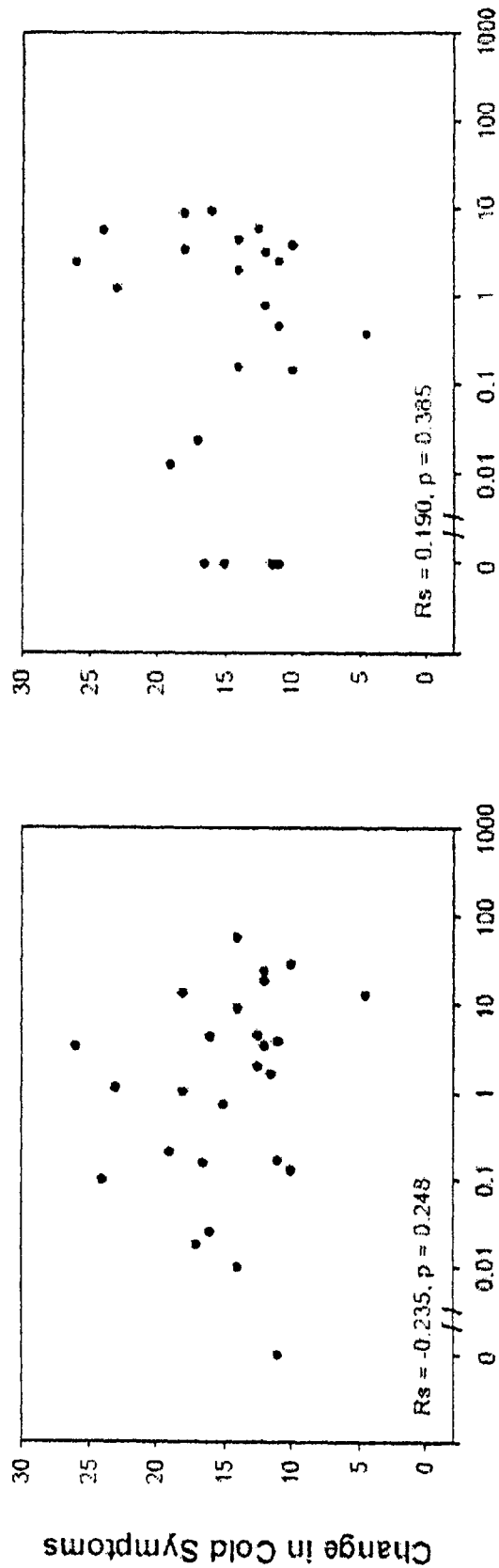
FIG. 18A-18F show airway neutrophilia correlations to changes in symptoms or lung function.
Figure 18:
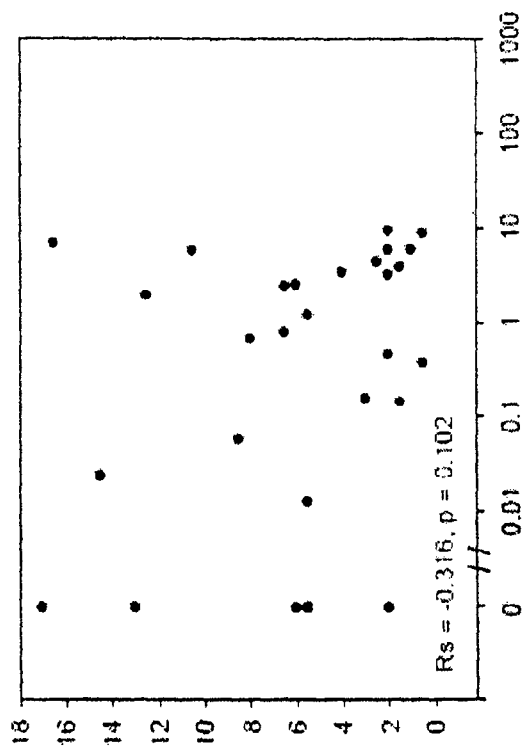
Figure 18:
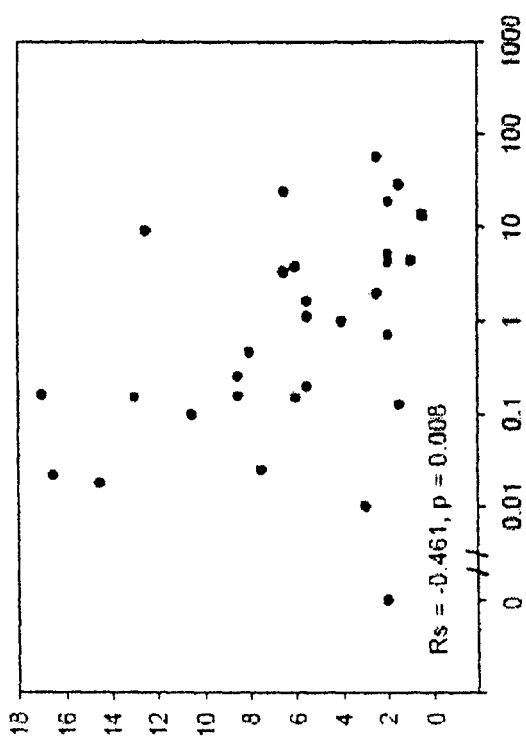
Figure 18:
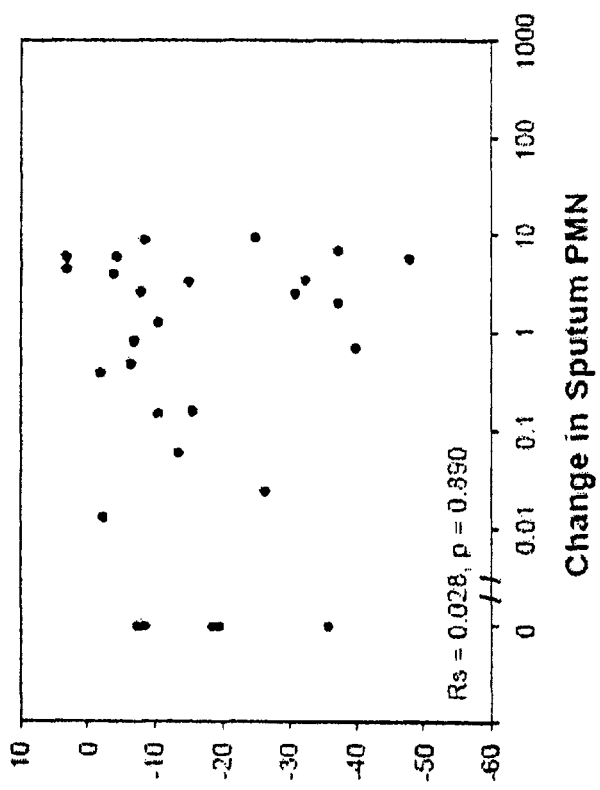
Figure 18:
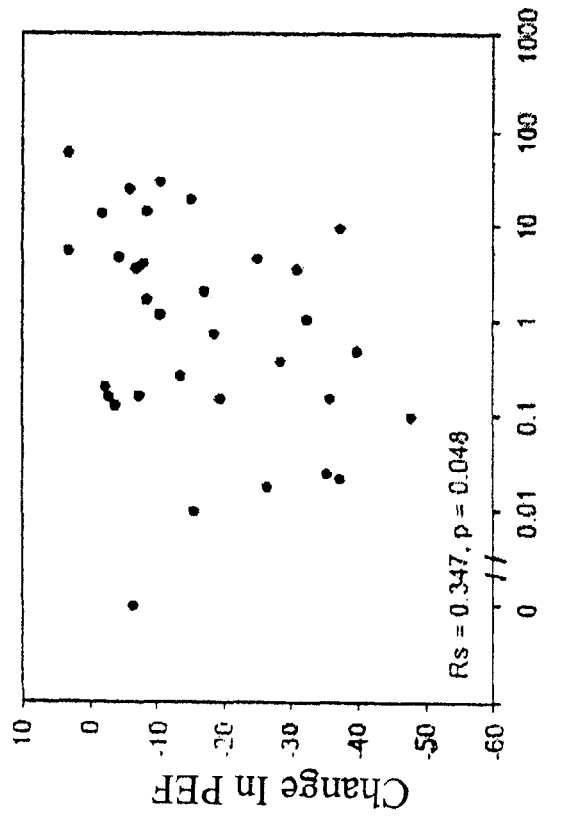

Associations of Nasal Lavage Neutrophilic Inflammation During the Cold with Asthma Symptoms and Lung Function. Nasal rhinoviral infection stimulates influx of neutrophils to both the upper and lower airways, that this process peaks by day five under experimental conditions with RV16 inoculation, and that increased neutrophils are associated with the risk of asthma exacerbations (FIG. 18). Consistent with an unknown time of exposure, the visits associated with peak neutrophil counts in the upper and lower airways were highly variable in this naturally acquired cold protocol. To compensate for the uncertain timing of viral exposure, FIG. 18 shows the peak minus convalescent change in airway neutrophil counts as a function of the change in symptoms or peak flow recordings. Neither nasal nor sputum neutrophils were associated with the change in total cold symptoms (FIGS. 18A-B), although the nasal neutrophil counts are associated with the nasal index of the modified Jackson symptom score (nasal discharge plus nasal congestion components divided by the total score; $R_s$=0.421, p=0.023).

There is an inverse relationship between the change in nasal lavage neutrophils and both the change in asthma symptoms and the difference in peak expiratory flow recordings (FIGS. 18C and 18E). Neither the maximum nor the change in sputum neutrophils correlate with differences in asthma symptoms or peak flow (FIGS. 18D and 18F), even after excluding data from four subjects with peak nasal neutrophils occurring several days after the peak in sputum PMN count suggestive of a new cold at the convalescent visit (not shown). By contrast, excluding these four subjects potentially with new colds strengthens the associations between nasal lavage neutrophils with both the change in asthma symptoms and peak flow measurements ($R_s$=−0.675 and 0.494 respectively).

Genomic Validation of the $P2X_7$ Pore Assay in Subjects with Asthma: Monocyte $P2X_7$ pore function is highly variable among healthy subjects and the whole blood agonist-stimulated dye uptake assay reliably identifies subjects with either characterized or novel loss-of-function polymorphisms with an area under the receiver-operator curve (AUC) of 0.94. Because the P2RX7 allele frequencies are not known in subjects with asthma, FIG. 19A redefines the performance characteristics of the functional pore assay in the present population, with initial estimates of the allele frequencies in this population shown in Table 7. When the three originally validated loss-of-function alleles (A1513C, T1729A, and G946A) are entered into the model together, the AUC is 0.688 without sufficient power for statistical significance (p=0.167). Adding the loss-of-function compound heterozygous genotype 1513 AC-1096 CG (ref) to the model increases the diagnostic power of the pore assay (AUC=0.788, p=0.014).

Based on prior predictions in healthy subjects, the inventors also added the G474A allele to the model resulting in the best performance (AUC=0.864, p<0.001). In this combined model, the optimal threshold for discriminating low from normal pore function is a 22-fold of BzATP-stimulated monocyte dye uptake with the following performance characteristics; sensitivity=0.75, specificity=0.96, positive predictive value=0.86, and negative predictive value=0.92.

TABLE 7

| P2RX7 Alleles | Healthy (N = 200) | Asthma (N = 31) |
|---|---|---|
| | Minor Allele Frequency | |
| Loss of Function | | |
| A1513C | 0.208 | 0.226 |
| T1729A | 0.038 | 0.065 |
| G946A | 0.012 | 0.016 |
| G474A | 0.022 | 0.032 |
| 1513C/1096G | 0.030 | 0.065 |
| Gain of Function | | |
| A1405C | 0.160 | 0.133 |

Figure 19:
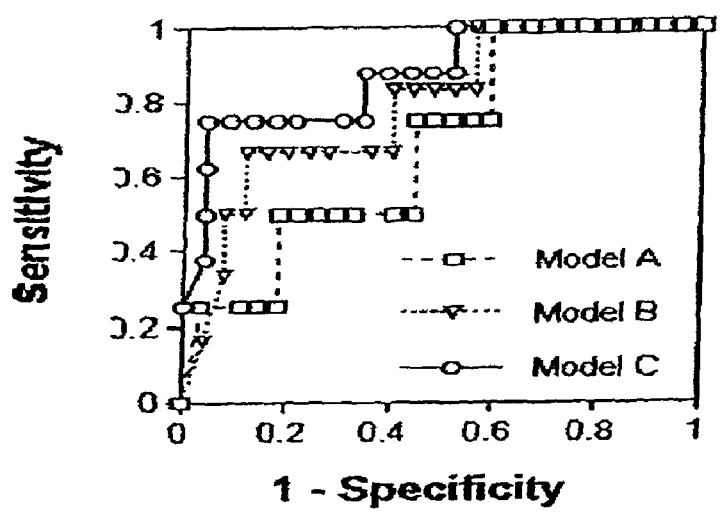
FIG. 19. Determination of the Optimal Threshold and Performance Characteristics of a Functional Screening Assay Detecting Variant P2RX7 Alleles. A) Using previously published methods (Denlinger 2006 Clinical Chemistry), a receiver-operator curve analysis was performed using validated loss of function genotypes as the standard to compare thresholds of low pore activity from those associated with normal genotypes. A recently published compound heterozygous state (Shemon 2006 J. Biol. Chem.) and a novel allele conferring loss of function were added to the model (A1513C-C1096G and G474A respectively). The area under the curves are 0.688, 0.788, and 0.864 with p-values of 0.167, 0.014 and <0.001 respectively. B) Despite adequate mRNA and protein expression of the G474A variant (also G150R) in transfected HEK 293 cells (not shown), this substitution confers a loss of pore function as determined by Bz-ATP stimulated uptake of YO-PRO-1 by a plate assay, even when the buffer conditions are more permissive than the WT control. The threshold for optimal screening assay performance was identified as 22-fold of Bz-ATP induced dye uptake. This threshold is associated with a sensitivity of 75%, specificity of 96%, positive predictive value of 86% and a negative predictive value of 92% respectively for identifying samples with these genotypes.
Figure 19:
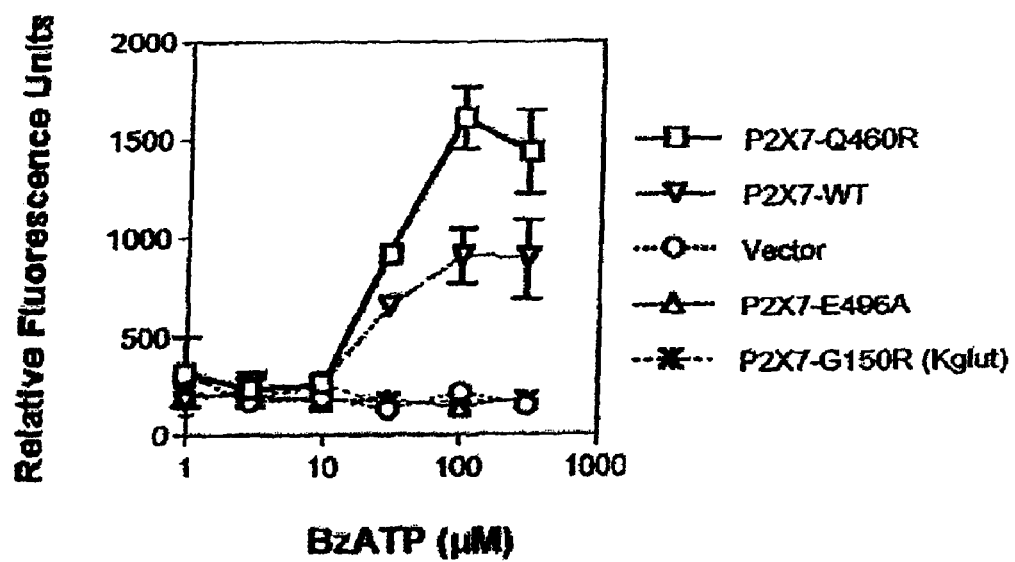

For comparison, the minor allele frequencies are presented for the subjects in this study relative to previously published data from healthy volunteers. To test whether the P2RX7 474 A allele (confers a glycine to arginine substitution at amino acid 150) is associated with attenuated function, the inventors next created a point mutant for recombinant expression in HEK293 cells. After confirming similar levels of mRNA and protein expression relative to the wild-type control (not shown), the function of these recombinant cells was assessed for $P2X_7$ pore function by the agonist-induced uptake of YO-PRO-1 in a fluorimetric plate assay (FIG. 19B).

In this assay system using a HEPES-buffered saline solution, the YO-PRO-1 fluorescence is increased roughly four fold by Bz-ATP stimulation of HEK cells expressing the $P2X_7$ wild type control with an $EC_{50}$ of 30 µM. As a loss-of-function control, the inventors also created the E496A variant lacking agonist-inducible pore activity in saline-containing buffers (FIG. 19B). Similarly, the G150R mutant exhibits no agonist stimulated increase in fluorescence even in a more permissive buffer system lacking NaCl (FIG. 19B). By contrast, the E496A variant has an approximately half-maximal increase in YO-PRO-1 fluorescence with an EC50 similar to wild type when stimulated by BzATP in this potassium glutamate buffer system (not shown). Moreover, previous results in our whole blood pore assay suggested the Q460R variant was a gain-of-function allele.

This notion is supported by the 8-fold increase in YO-PRO-1 fluorescence over baseline induced by BzATP treatment of the HEK-$P2X_7$ Q460R cells, again with an $EC_{50}$ of approximately 30 µM. Thus, the $P2X_7$ pore assay in whole blood has very good predictive power for identifying samples with known and novel variant alleles, and can be used as a continuous variable to begin to investigate relationships between this receptor system and disease biomarkers or endpoints.

Figure 20:
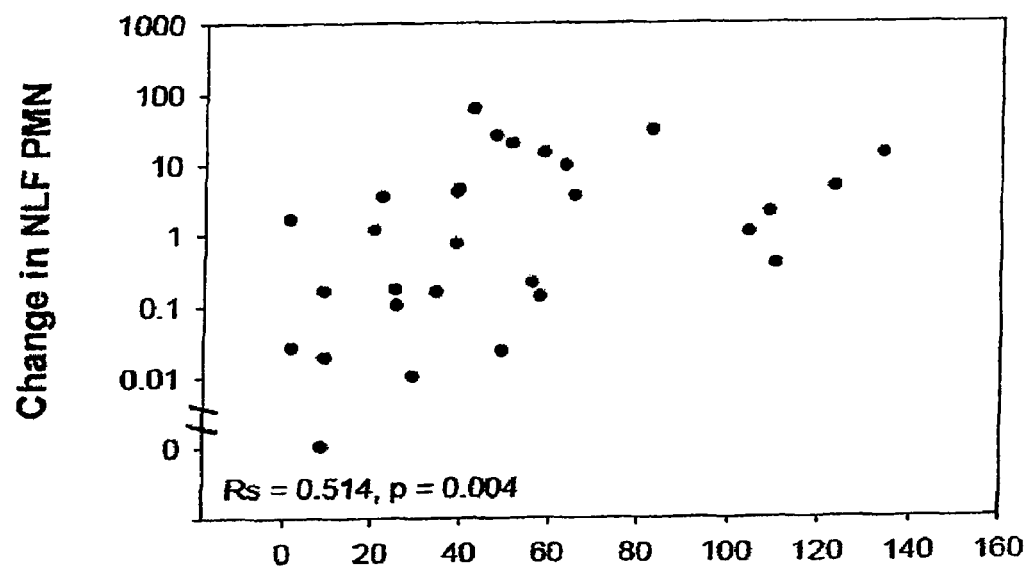
FIG. 20. Change in Airway Neutrophil Count During a Cold by $P2X_7$ Pore Function. Baseline neutrophil counts were subtracted from the peak levels of nasal lavage (A) and sputum neutrophils (B) to reflect the corresponding changes in cold symptoms. Data are plotted against $P2X_7$ pore function assessed in whole blood samples by the fold of agonist induced dye uptake. Spearman correlation coefficients are shown.
Figure 20:
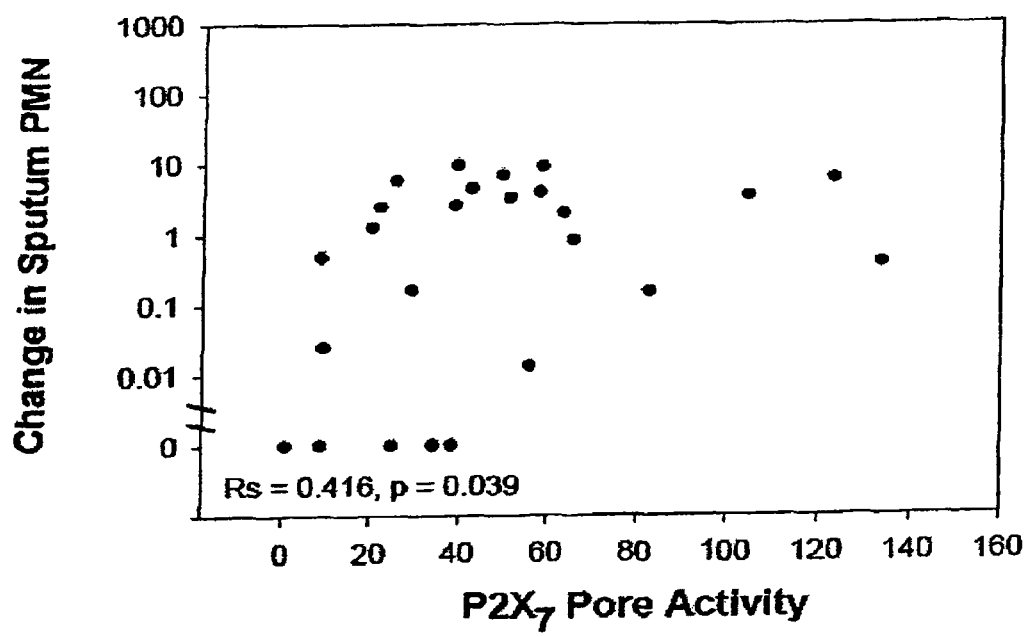

Correlates to Asthmatic Airway Neutrophilia During a Naturally Occurring Upper Respiratory Tract Infection. Given that attenuation of $P2X_7$ function alters neutrophil accumulation to compartmentalized areas of inflammation in animal models, the inventors were interested to evaluate this relationship during the upper and lower airway inflammatory response to naturally occurring viral infection. FIG. 20 shows that the range of $P2X_7$ pore activity in whole blood spans two orders of magnitude, similar to previous results with healthy subjects. To account for the variable timing of a naturally occurring infection, the peak minus convalescent airway neutrophil counts are shown as a function of $P2X_7$ pore activity. Both nasal lavage (FIG. 20A) and sputum (FIG. 20B) neutrophil changes correlate with pore function, such that greater degrees of pore activity are associated with larger acute changes in neutrophil accumulation. Five subjects had a delayed neutrophil response in the lower airway that occurred after the convalescence of cold and asthma symptoms. If these subjects are excluded from the analysis, the correlation with sputum neutrophils loses statistical power (Rs,p), whereas the correlation between pore activity and the change in nasal lavage neutrophils is strengthened in this case (Rs, p)

Figure 21:
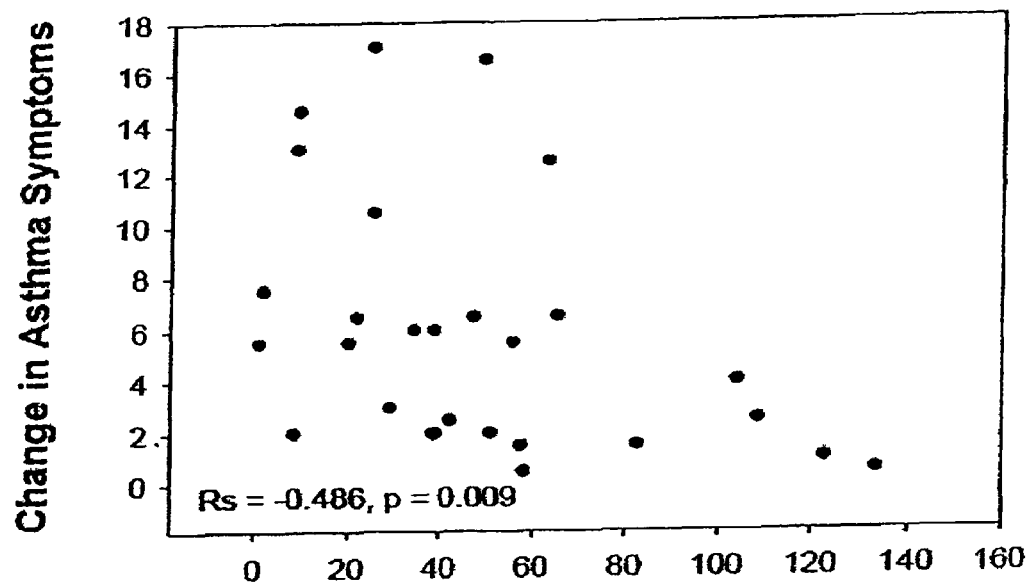
FIG. 21. Change in Asthma Symptom Score by $P2X_7$ Pore Activity. The change in asthma symptoms (A) and peak flow (B) during the course of the cold is plotted against $P2X_7$ Pore Activity in whole blood. Spearman correlation coefficients are shown.
Figure 21:
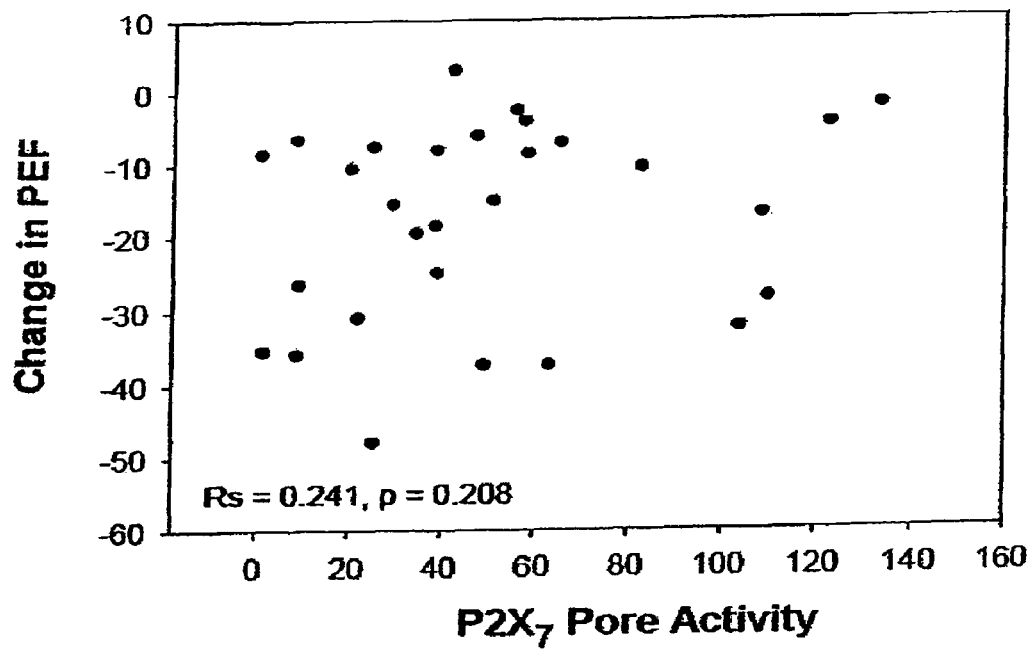

Asthma Symptoms, Lung Function and Exacerbations: Four subjects enrolled in this protocol experienced a severe asthma exacerbation and twelve subjects met criteria for a mild exacerbation. The percent predicted $FEV_1$, the change in sputum neutrophils, and the detection of respiratory viruses have been shown by others to associate with exacerbation risk, however univariate logistic regression analysis for exacerbation status was not significant for these factors in our dataset. To begin to delineate predictors of the components of asthma exacerbations, FIG. 21 shows the changes in asthma symptoms or peak flow recordings during the acute cold as a function of $P2X_7$ pore activity. In this regard, $P2X_7$ function inversely correlates with the development of asthma symptoms during the cold (FIG. 21A) but no relationship was found with peak flow recordings (FIG. 21B). Multivariate stepwise regression analysis of factors related to asthma symptoms is shown in Table 8. The change in peak flow rates and $P2X_7$ pore activity are the most predictive factors in this model.

TABLE 8

| Factor | Univariate | | Stepwise Multivariate | |
|---|---|---|---|---|
| | F | p | $R^2$ | p |
| Baseline FEV1 | 0.1 | 0.782 | | |
| Baseline Methacholine $PC_{20}$ | 0.1 | 0.764 | | |
| Nasal Index | 0.3 | 0.274 | | |
| Change in Nasal PMN | 6.2 | 0.019 | | |
| Change in PEF | 11.9 | 0.002 | 0.316 | 0.002 |
| $P2X_7$ Pore Activity | 7.1 | 0.013 | 0.421 | 0.044 |

Factors were entered into the univariate model based on the correlations observed previously and expectations from the literature. Preliminary modeling suggested that the Nasal Index was a better predictor of asthma symptoms than the total cold score. This index is defined as the sum of the scores for the nasal discharge and nasal congestion components of the Modified Jackson cold symptom instrument, divided by the total score. Factors were entered into the stepwise model based on the highest F ratios at the time of sequential factor selection. The $R^2$ value increases sequentially upon factor addition until none of the remaining factors help the model.

$P2X_7$ Pore Function Correlations with Nasal Inflammation and Asthma Symptoms. Given that attenuation of $P2X_7$ function alters neutrophil accumulation to compartmentalized areas of inflammation in animal models, the inventors evaluated this relationship during the upper and lower airway inflammatory response to naturally occurring viral infection. In this regard, the inventors found a correlation between $P2X_7$ pore activity and the change or the peak in nasal lavage neutrophil counts and an inverse relationship with the change in asthma symptoms. No association was apparent between $P2X_7$ function and the change in peak flow recordings (p>0.1). Univariate predictors of the change in asthma symptoms during the cold included the change in PEF, the peak of cold symptoms, the peak on nasal lavage neutrophils and the $P2X_7$ pore activity. Multivariate regression analysis of these factors demonstrated that the change in PEF and $P2X_7$ pore activity were the best predictors of asthma symptoms in this study.

Figure 22:
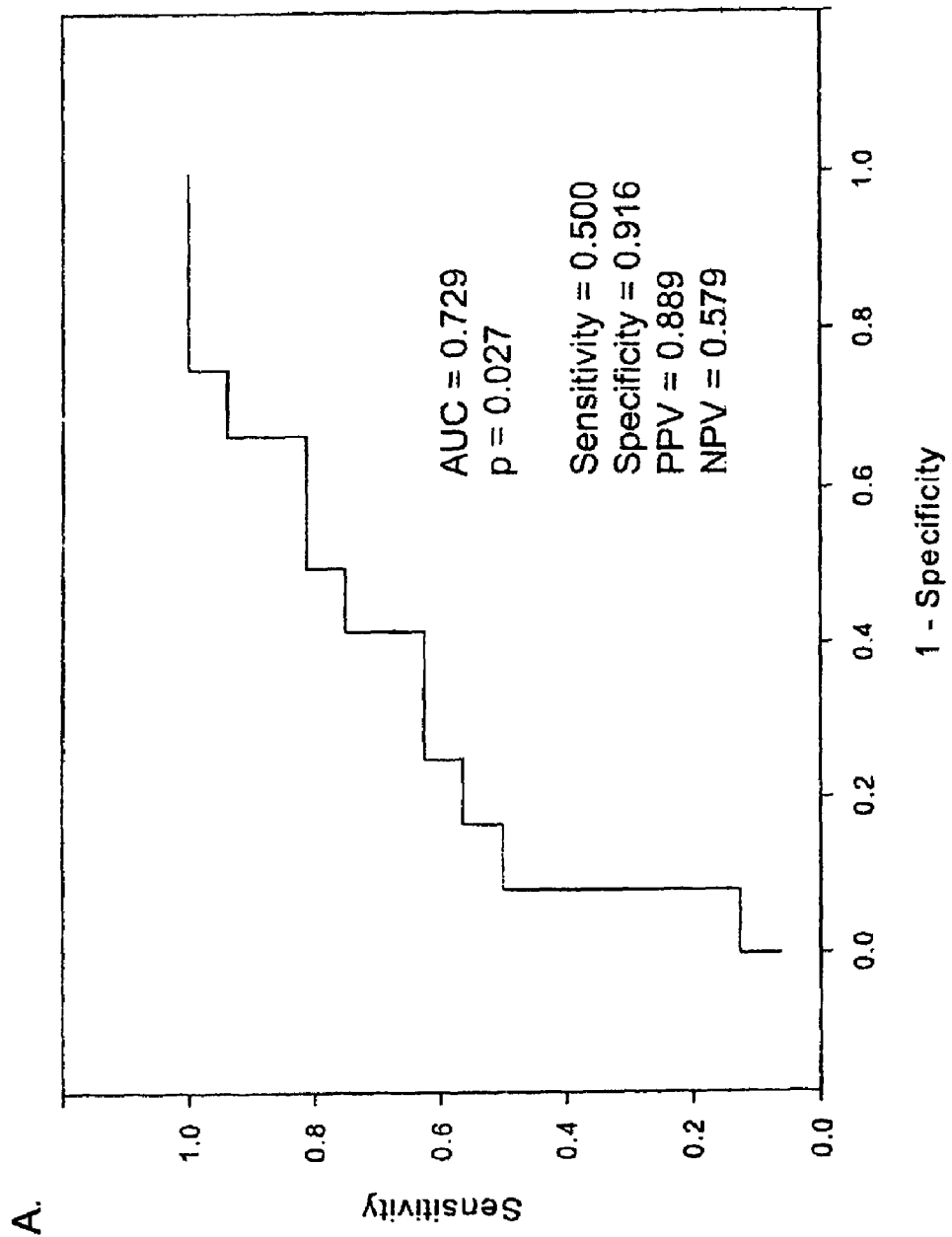
FIG. 22. Use of the $P2X_7$ Pore Assay to Predict Loss of Asthma Control during the Cold. Loss of asthma control was scored binomially based on changes in medication usage, symptom scores, and changes in lung function as defined in Methods. (A) shows a receiver-operator curve where $P2X_7$ pore function was used in logistic regression analysis to predict the likelihood of the loss of asthma control. The optimal threshold for identifying subjects with loss of control is less than 26-fold of BzATP induced YO-PRO-1 uptake. (B) separates subjects by their $P2X_7$ Pore Activity using this threshold while plotting the change in asthma symptoms. A p-value from a students' t-test with equal variance is shown.
Figure 22:
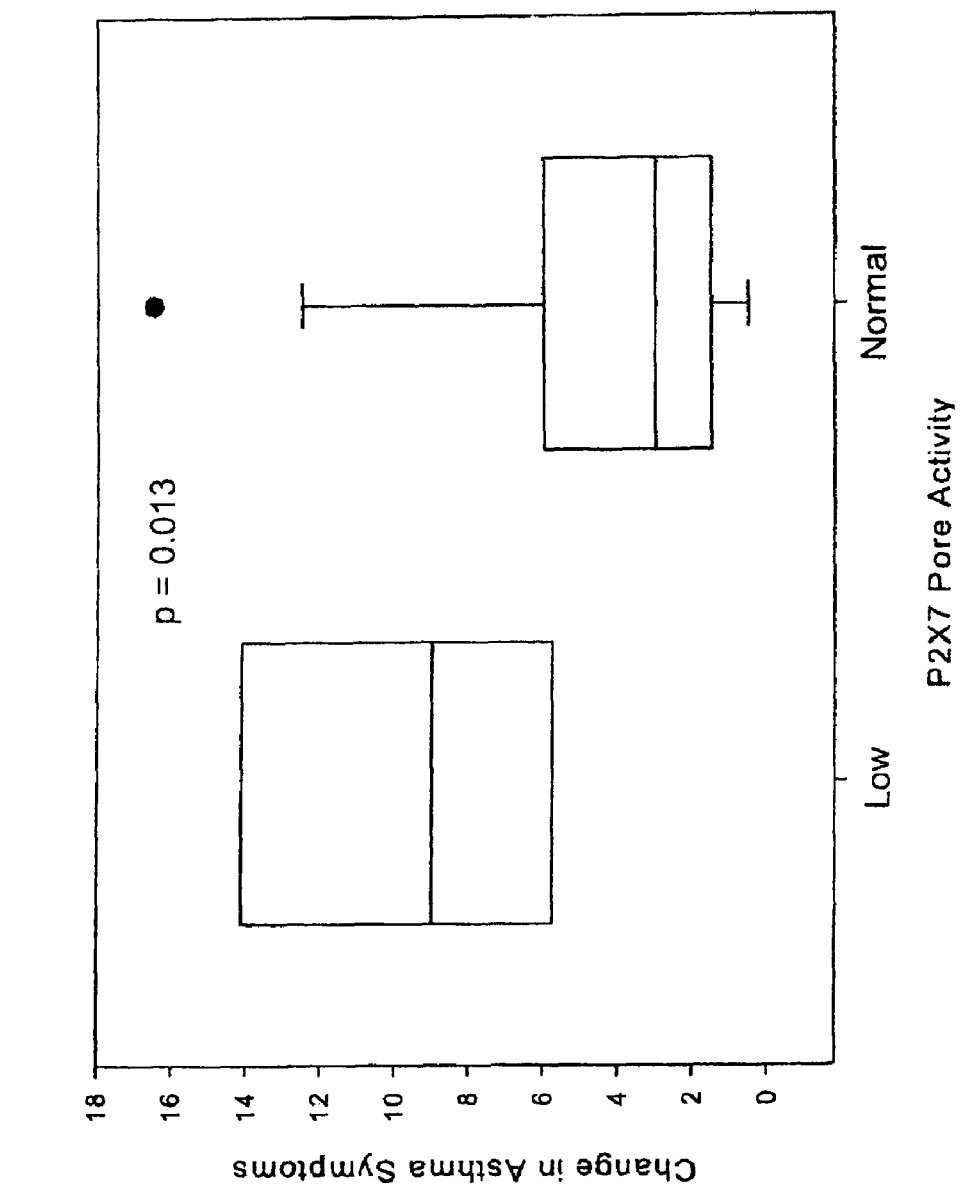

To assess whether $P2X_7$ pore function relates to the risk of virus induced loss of asthma control, the inventors performed logistic regression with receiver-operator analysis shown in FIG. 22A. This model exhibited an AUC of 0.729 (p=0.027) with the best threshold performance at a pore activity below 26-fold stimulation of BzATP-induced YOPRO-1 uptake. At this threshold, the likelihood ratios for predicting the risk of asthma were 5.95 and 0.55 for LR+ and LR− respectively.

Additionally with this cut point, subjects with low pore activity had significantly higher asthma symptoms during the cold (FIG. 22B). Moreover, the odds ratio associating low pore activity with the risk of developing an asthma exacerbation during the cold was 11, representing a 95% confidence interval: 1.1, 106.4. Thus, the whole blood pore assay of the present invention may represent a novel biomarker to predict the severity of asthma symptoms and P2RX7 may be a candidate asthma gene, particularly with respect to the risk domain for maintaining asthma control.

Example 6

Plate Assay Methods

This example describes plate assay methods used by the inventors. The plate assay methods are suitable for pharmacogenomic comparisons among results from the whole blood assay to compartmentalized cellular responses. Primary human alveolar macrophages may also be used for these purposes. In this fashion the whole blood assay may be used to predict drug responses in compartmentalized disease states including, for example, pain and/or airway inflammation.

Cells are plated to achieve 50-75% confluency in a black 96-well microtiter plate. The solutions are the same as described in the flow cytometry method with the exception of variable concentrations of agonists and antagonists (not shown). After 20 min. of agonist stimulation in the presence of YO-PRO-1, the excess extracellular dye is washed away and fluorescence is detected in a fluorimetric plate reader with appropriate YO-PRO-appropriate filters for excitation and emission. Cells are plated to achieve 50-75% confluency in a black 96-well microtiter plate. The solutions used are the same as described in the flow cytometry method with the exception of variable concentrations of agonists and antagonists (not shown). After twenty of agonist stimulation in the presence of YO-PRO-1, the excess extracellular dye is washed away and fluorescence is detected in a fluorimetric plate reader with appropriate YO-PRO-appropriate filters for excitation and emission.

The plate assay allows for pharmacogenomic comparisons among results from the whole blood assay to compartmentalized cellular responses. The data shown in Tables 9-11 are representative attempts to determine the 50% effective concentration of $P2X_7$ agonists with an astrocytoma cell line.

The inventors have also used primary human alveolar macrophages for these purposes. In general, this data shows that the whole blood assay may be able to predict drug responses in compartmentalized disease states including pain and/or airway inflammation.

TABLE 9

| | $5 \times 10^4$ 1321N1 cells | | | | | | |
|---|---|---|---|---|---|---|---|
| | 1 | 2 | 3 | 4 | 5 | 6 | 7 |
| A: No agonist controls | K Glut Buffer | K Glut Buffer | K Glut Buffer | K Glut Buffer | K Glut Buffer | K Glut Buffer | 10 μM YOPRO only |
| B: BzATPdose + YOPRO | 1 μM | 1 μM | 3 μM | 3 μM | 10 μM | 10 μM | 30 μM |
| C: ATPdose + YOPRO | 10 μM | 10 μM | 30 μM | 30 μM | 100 μM | 100 μM | 300 μM |
| D: 2MeSATPdose + YOPRO | 3 μM | 3 μM | 10 μM | 10 μM | 30 μM | 30 μM | 100 μM |
| E: ab-CH2-ATP + YOPRO | 1 μM | 1 μM | 3 μM | 3 μM | 10 μM | 10 μM | 30 μM |

TABLE 9-continued

| | | | | | | | |
|---|---|---|---|---|---|---|---|
| F: 1 mM ATP + KN62dose + YOPRO | 1 µM | 1 µM | 3 µM | 3 µM | 10 µM | 10 µM | 30 µM |
| G: Single dose agents + YOPRO | 300 µM UTP | 300 µM UTP | 300 µM ATP-g-S | 300 µM ATP-g-S | 300 µM AMPPNP | 300 µM AMPPNP | |
| H: No Cells | 10 µM YOPRO | 10 µM YOPRO | 300 µM ab-CH2-ATP | 300 µM UTP | 300 µM ATP-g-S | 300 µM AMPPNP | 300 µM KN62 |

| | 5 × 10⁴ 1321N1 cells | | | | |
|---|---|---|---|---|---|
| | 8 | 9 | 10 | 11 | 12 |
| A: No agonist controls | 10 µM YOPRO only | 10 µM YOPRO only | 10 µM YOPRO only | 10 µM YOPRO only | 10 µM YOPRO only |
| B: BzATPdose + YOPRO | 30 µM | 100 µM | 100 µM | 300 µM | 300 µM |
| C: ATPdose + YOPRO | 300 µM | 1 mM | 1 mM | 3 mM | 3 mM |
| D: 2MeSATPdose + YOPRO | 100 µM | 300 µM | 300 µM | 1 mM | 1 mM |
| E: ab-CH2-ATP + YOPRO | 30 µM | 100 µM | 100 µM | 300 µM | 300 µM |
| F: 1 mM ATP + KN62dose + YOPRO | 30 µM | 100 µM | 100 µM | 300 µM | 300 µM |
| G: Single dose agents + YOPRO | | | | | |
| H: No Cells | 1 mM 2MeSATP | 3 mM ATP | 300 µM BzATP | | |

TABLE 10

| | 1 | 2 | 3 | 4 | 5 | 6 | 7 | 8 | 9 | 10 | 11 | 12 |
|---|---|---|---|---|---|---|---|---|---|---|---|---|
| A | 9 | 9 | 10 | 9 | 9 | 10 | 66 | 73 | 73 | 70 | 86 | 85 | 485/20, 528/20 |
| B | 98 | 89 | 188 | 188 | 213 | 206 | 217 | 218 | 214 | 223 | 220 | 232 | 485/20, 528/20 |
| C | 207 | 189 | 203 | 208 | 204 | 212 | 218 | 209 | 201 | 212 | 165 | 182 | 485/20, 528/20 |
| D | 109 | 102 | 144 | 144 | 157 | 154 | 155 | 170 | 162 | 168 | 161 | 164 | 485/20, 528/20 |
| E | 68 | 67 | 68 | 69 | 74 | 74 | 74 | 78 | 83 | 89 | 101 | 116 | 485/20, 528/20 |
| F | 185 | 177 | 181 | 176 | 159 | 159 | 155 | 153 | 148 | 148 | 152 | 165 | 485/20, 528/20 |
| G | 72 | 73 | 131 | 130 | 75 | 86 | | | | | | | 485/20, 528/20 |
| H | 25 | 26 | 23 | 11 | 11 | 10 | 11 | 10 | 10 | 10 | | | 485/20, 528/20 |

TABLE 11

| | K-Glu | YOPRO only | 1 uM | 3 uM |
|---|---|---|---|---|
| BzATPdose + YOPRO | 9 | 75.5 | 93.5 | 188 |
| ATPdose + YOPRO | 9 | 75.5 | 198 | 205.5 |
| 2MeSATPdose + YOPRO | 9 | 75.5 | 105.5 | 144 |
| ab-CH2-ATP + YOPRO | 9 | 75.5 | 67.5 | 68.5 |
| 1 mM ATP + KN62dose + YOPRO | 9 | 75.5 | 181 | 178.5 |

The invention has been herein shown and described in what is perceived to be preferred embodiments, it is to be understood that the invention is not intended to be limited to the specific embodiments set forth above. Rather, it is recognized that certain modifications, substitutions, alterations, omissions may be made by one of skill in the art of the invention without departing from the spirit or intent of the invention. Accordingly, the invention is to be taken as including all reasonable equivalents to the subject matter of the appended claims and the foregoing description is meant to be exemplary only and should not limit the scope of the invention set forth in the following claims.

What is claimed is:

1. A method of assaying nucleotide receptor $P2X_7$ pore activity in white blood cells contained within a mixed cell sample, comprising the steps of:
   (a) labeling white blood cells contained within the mixed cell sample with a white blood cell-specific label;
   (b) depolarizing the labeled white blood cells with an isotonic depolarizing solution;
   (c) contacting the labeled white blood cells with a dye and a $P2X_7$ agonist in an amount sufficient to activate nucleotide receptor $P2X_7$ pore activity;
   (d) contacting the labeled white blood cells of step (c) with a divalent cation in an amount sufficient to deactivate nucleotide receptor $P2X_7$ pore activity; and
   (e) analyzing dye uptake in the labeled white blood cells of step (d) whereby nucleotide receptor $P2X_7$ pore activity is quantified by the amount of dye taken up in labeled white blood cells treated with the $P2X_7$ agonist relative to labeled white blood cells in the absence of said $P2X_7$ agonist, and wherein said nucleotide receptor $P2X_7$ pore activity is corrected for sample age by subtracting nucleotide receptor P2X$_7$ pore activity contributed by nonviable white blood cells.

2. A method according to claim 1 wherein the white blood cell-specific label is a phycoerythrin-conjugated anti-CD14 antibody.

3. A method according to claim 1 wherein the isotonic depolarizing solution comprises glutamate ion with the proviso that sodium and chloride ions and divalent cations are absent from said isotonic depolarizing solution in amounts effective to inhibit P2X$_7$ pore activity.

4. A method according to claim 1 wherein the dye is a DNA-binding dye having a mass of less than approximately 900 Daltons.

5. A method according to claim 4 wherein said DNA-binding dye is YO-PRO-1.

6. A method according to claim 1 wherein the P2X$_7$ agonist is selected from the group consisting of 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5' (beta,gamma-imido)triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof.

7. A method according to claim 1 wherein the divalent cation is magnesium ion.

8. A method according to claim 1 wherein dye uptake in step (e) is measured by flow cytometry.

9. A method according to claim 8 wherein said flow cytometry detects labeled white blood cells apart from non-labeled cells and measures intensity of the dye taken up by the labeled white blood cells whereby nucleotide receptor P2X$_7$ pore activity is quantified by the amount of dye taken up in labeled white blood cells in the absence of said P2X$_7$ agonist.

10. The method according to claim 1, wherein the step of subtracting from nucleotide receptor P2X$_7$ pore activity the nucleotide receptor P2X$_7$ pore activity contributed by nonviable white blood cells comprises excluding nonviable cells from the analysis.

11. The method according to claim 10, wherein excluding nonviable cells from the analysis comprises contacting the white blood cells of step (d) with a second dye to identify nonviable cells.

12. The method according to claim 11, wherein the second dye is propidium iodide.

13. The method according to claim 10, wherein excluding nonviable cells from the analysis comprises (a) calibrating a flow cytometer such that the standardized calibration settings optimize selection of viable white blood cells for further analysis and the exclusion of nonviable cells from further analysis, and (b) using the flow cytometer to exclude the nonviable cells from further analysis.

14. A kit for measuring a nucleotide receptor P2X$_7$ pore activity in white blood cells contained within a mixed cell sample of a subject, the kit comprising:
(a) a white blood cell-specific label for labeling white blood cells contained within the subject's sample;
(b) a dye capable of uptake by nucleotide receptor P2X$_7$ pores;
(c) a P2X$_7$ agonist in an amount sufficient to activate nucleotide receptor P2X$_7$ pore activity in the white blood cells contained within the subject's blood sample;
(d) an isotonic depolarizing solution for depolarizing the labeled white blood cells;
(e) a second dye that identifies and excludes nonviable cells; and,
(f) instructional material describing labeling white blood cells contained within the subject's sample with the white blood cell-specific label; depolarizing the labeled white blood cells with the isotonic depolarizing solution; contacting the labeled white blood cells with the dye capable of uptake by nucleotide receptor P2X$_7$ pores and the P2X$_7$ agonist in an amount sufficient to activate nucleotide receptor P2X$_7$ pore activity; deactivating nucleotide receptor P2X$_7$ pore activity; and analyzing dye uptake in the labeled white blood cells whereby nucleotide receptor P2X$_7$ pore activity is quantified by the amount of dye taken up in labeled white blood cells treated with the P2X$_7$ agonist relative to labeled white blood cells in the absence of said P2X$_7$ agonist, said nucleotide receptor P2X$_7$ pore activity being corrected for sample age by subtraction of nucleotide receptor P2X$_7$ pore activity contributed by nonviable white blood cells using the second dye that identifies and excludes the nonviable cells.

15. The kit according to claim 14 wherein the white blood cell-specific label is a phycoerythrin-conjugated anti-CD14 antibody.

16. The kit according to claim 14 wherein the isotonic depolarizing solution comprises glutamate ion with the proviso that sodium and chloride ions and divalent cations are absent from said isotonic depolarizing solution in amounts effective to inhibit P2X$_7$ pore activity.

17. The kit according to claim 14 wherein the dye is a DNA-binding dye having a mass of less than approximately 900 Daltons.

18. The kit according to claim 17 wherein said DNA-binding dye is YO-PRO-1.

19. The kit according to claim 14 wherein the P2X$_7$ agonist is selected from 2'-3'-O-(4-benzoyl)-adenosine 5'-triphosphate (Bz-ATP), adenosine 5'-triphosphate (ATP), 2-methylthio-adenosine 5'-triphosphate (2-MeS-ATP), adenosine 5'-(3-thiotriphosphate) (ATP-gamma-S), 2-chloro-adenosine 5'-triphosphate (2-Cl-ATP), adenosine 5' (beta,gamma-imido) triphosphate (AMPPNP), adenosine 5'-diphosphate (ADP), 2-methylthio-adenosine 5'-diphosphate (2-MeS-ADP), 2-chloro-adenosine 5'-diphosphate (2-Cl-ADP) and mixtures thereof.

20. The kit according to claim 14 further comprising a divalent cation in an amount sufficient to deactivate nucleotide receptor P2X$_7$ pore activity in the white blood cells contained within the subject's blood sample.

21. The kit according to claim 20 wherein the divalent cation is magnesium ion.

22. The kit according to claim 14 wherein said instructional material further comprises a decision tree which, based on at least the nucleotide receptor P2X$_7$ pore activity measured by said kit, directs a user to a subject-specific clinical pathway of medical intervention for said subject.

23. The kit according to claim 14 wherein said instructional material describes the analysis of dye uptake by flow cytometry, wherein said flow cytometry detects labeled white blood cells apart from non-labeled cells and measures intensity of the dye taken up by the labeled white blood cells whereby nucleotide receptor P2X$_7$ pore activity is quantified by the amount of dye taken up in labeled white blood cells in the absence of said P2X$_7$ agonist.

* * * * *